(12) United States Patent
Zhou et al.

(10) Patent No.: US 7,425,552 B2
(45) Date of Patent: Sep. 16, 2008

(54) PYRIDAZINONE COMPOUNDS

(75) Inventors: Yuefen Zhou, San Diego, CA (US);
Liansheng Li, San Diego, CA (US);
Stephen E. Webber, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 328 days.

(21) Appl. No.: 11/304,902

(22) Filed: Dec. 16, 2005

(65) Prior Publication Data

US 2006/0189602 A1 Aug. 24, 2006

Related U.S. Application Data

(60) Provisional application No. 60/636,616, filed on Dec. 17, 2004.

(51) Int. Cl.
C07D 513/04 (2006.01)
C07D 417/04 (2006.01)
A61K 31/549 (2006.01)

(52) U.S. Cl. .................. 514/222.8; 544/10; 544/12; 514/223.2

(58) Field of Classification Search .......... 544/10, 544/12; 514/222.8, 223.2
See application file for complete search history.

(56) References Cited

U.S. PATENT DOCUMENTS

| 2005/0153877 A1 | 7/2005 | Miao et al. |
| 2006/0003346 A1 | 1/2006 | Amin et al. |
| 2006/0040927 A1 | 2/2006 | Blake et al. |
| 2006/0189602 A1 | 8/2006 | Zhou et al. |
| 2006/0211695 A1 | 9/2006 | Borzilleri et al. |
| 2006/0252785 A1 | 11/2006 | Blake et al. |
| 2008/0031852 A1 | 2/2008 | Webber et al. |

FOREIGN PATENT DOCUMENTS

| WO | WO 01/85172 A1 | 11/2001 |
| WO | WO 2002/098424 A1 | 12/2002 |
| WO | WO 03/059356 A2 | 7/2003 |
| WO | WO-2006/115221 | 11/2006 |

OTHER PUBLICATIONS

Int'l Search Report and Written Opinion of Int'l Appl. No. PCT/US05/45588.
U.S. Appl. No. 11/766,668, Ellis et al.
U.S. Appl. No. 11/898,334, Zhou et al.
U.S. Appl. No. 11/861,678, Dragovich et al.
U.S. Appl. No. 11/955,193, Ruebsam et al.
U.S. Appl. No. 11/955,144, Tran et al.
U.S. Appl. No. 12/048,933, Ruebsam et al.
U.S. Appl. No. 12/061,499, Ellis et al.
U.S. Appl. No. 11/845,515, Tran et al.
Tedesco et al., 3-(1,2,4)-benzothiadiazin-3-yl)-4-hydroxy-2(1H)-quinolinones, Potent Inhibitors of Hepatitis C Virus RNA-Dependent RNA Polymerase, J. Med. Chem. 49:971-983 (2006).
Fisyuk et al., Synthesis of 5,6-Dihydropyridin-2(1H)-ones, 1,5,6,8,8a-Hexahydrosoquinolin-3(2H)-ones and 4a,5,6,7,8,8a-hexahydroquinolin-2(1H)-ones by Intramolecular Wittig Reaction. Molecules, Feb. 28, 2002, vol. 7, pp. 124-128.
Int'l Search Report and Written Opinion of Int'l Appl. No. PCT/US07/87272.
Intl'l Search Report and Written Opinion of Int'l Appl. No. PCT/US07/87288.

*Primary Examiner*—Kahsay T Habte
(74) *Attorney, Agent, or Firm*—Connolly Bove Lodge & Hutz LLP

(57) ABSTRACT

The invention is directed to pyridazinone compounds of Formula I and pharmaceutical compositions containing compounds of Formula I

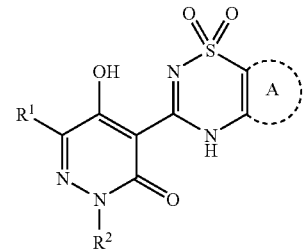

wherein $R^1$ and $R^2$ are independently H, alkyl, cycloalkyl, aryl, or heterocyclyl; and Ring A is 5 or 6-membered aryl or heterocyclyl. The invention also encompasses methods of using a compound of Formula I in the treatment of hepatitis C virus infections.

14 Claims, No Drawings

PYRIDAZINONE COMPOUNDS

This application claims the benefit of U.S. Provisional Application No. 60/636,616, filed on Dec. 17, 2004.

FIELD OF THE INVENTION

The invention is directed to pyridazinone compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately $31,000/year. These drugs have difficult dosing problems and side-effects that preclude their use in almost half of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; approximately one third of patients do not respond. Of those who do respond, a large fraction relapses within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects. While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel pyridazinone compounds, pharmaceutically acceptable prodrugs, pharmaceutically active metabolites, pharmaceutically acceptable salts, and pharmaceutically acceptable solvates thereof, which are useful in treating or preventing a hepatitis C virus infection in a patient in need thereof comprising administering to the patient a therapeutically or prophylactically effective amount of a pyridazinone compound.

In a general aspect, the invention relates to compounds of Formula I wherein
$R^1$ and $R^2$ are independently H, alkyl, cycloalkyl, aryl, or heterocyclyl, and Ring A is 5 or 6-membered aryl or heterocyclyl,
wherein the above alkyl, aryl, cycloalkyl, or heterocyclyl moieties are optionally substituted by 1-3 substituents selected from
alkanoyl,
alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
—N=N—NH2,
—C(O)$_2$—($C_1$-$C_6$ alkyl), —C(O)$_2$-(aryl), —C(O)$_2$-(cycloalkyl), —C(O)$_2$-(heterocyclyl), —O—($C_1$-$C_6$ haloalkyl), —O—($C_1$-$C_6$ alkyl)aryl, —O—($C_1$-$C_6$ alkyl)cycloalkyl, —O—($C_1$-$C_6$ alkyl)heterocyclyl, —O—($C_1$-$C_6$ alkyl)amino, —O—($C_1$-$C_6$ alkyl)alkylamino, —O—($C_1$-$C_6$ alkyl)dialkylamino, —O—($C_1$-$C_6$ alkyl)-C(O)OH, —O—($C_1$-$C_6$ alkyl)-C(O)—O—($C_1$-$C_6$ alkyl), —O—($C_1$-$C_6$ alkyl)-C(O)NH$_2$, —O—($C_1$-$C_6$ alkyl)-C(O)NH—($C_1$-$C_6$ alkyl), —O—($C_1$-$C_6$ alkyl)-C(O)N—($C_1$-$C_6$ alkyl)dialkyl, —O—($C_1$-$C_6$ alkyl)-C(O)-heterocyclyl, —O-aryl, —O-heterocyclyl, —NHC(O)($C_1$-$C_6$ alkyl), —NHC(O)($C_1$-$C_6$ alkylene), —NHC(O-aryl), —NHC(O)(cycloalkyl), —NHC(O)$_2$-(heterocyclyl), —NHC(OH$C_1$-$C_6$ alkyl)aryl, —NHC(O)$_2$—$C_1$-$C_6$ alkyl)cycloalkyl, —NHC(O)—($C_1$-$C_6$ alkyl)heterocyclyl, —NHC(O)—($C_1$-$C_6$ alkyl)amino, —NHC(O)—($C_1$-$C_6$ alkyl)alkylamine, —NHC(O)—($C_1$-$C_6$ alkyl)dialkylamine, —NHC(O)—($C_1$-$C_6$ alkyl)C(O)amino, —NHC(O)—($C_1$-$C_6$ alkyl)C(O)alkylamine, —NHC(O)—($C_1$-$C_6$ alkyl)C(O)dialkylamine, —NHC(O)—($C_1$-$C_6$ alkyl)N(H)—($C_1$-$C_6$ alkyl)C(O)$_2$—($C_1$-$C_6$ alkyl), —NHC(O)—($C_1$-$C_6$ alkyl)S(O)$_2$ ($C_1$-$C_6$ alkyl), —NHC(O)—($C_1$-$C_6$ alkyl)-S-(heterocyclyl), —NHS(O)$_2$-($C_1$-$C_6$ alkyl), —NHS(O)$_2$-aryl), —NHS(O)$_2$-cycloalkyl), —NHS(O)$_2$-(heterocyclyl), —NHS(O)($C_1$-$C_6$ alkyl), —NHS(O)(aryl), —NHS(O)(cycloalkyl), —NHS(O)(heterocyclyl), —NHS($C_1$-$C_6$ alkyl), —NHS(aryl), —NHS(cycloalkyl), —NH—S-(heterocyclyl), wherein each of the above substituents can be further optionally substituted by 1-5 substituents selected from
amino,
cyano,
halo,
nitro,
$C_1$-$C_6$ alkylamine, $C_1$-$C_6$ dialkylamine, and
$C_1$-$C_6$ alkyl, $C_1$-$C_6$ alkoxy, $C_1$-$C_6$ alkenyl, $C_1$-$C_6$ hydroxyl, and $C_1$-$C_6$ hydroxyalkyl, each optionally substituted by halo, or a pharmaceutically acceptable salt, hydrate, tautomer or stereoisomer thereof.

In one aspect, the compound of the invention relates to compounds of Formula I wherein $R^1$ is selected from the group consisting of $C_1$-$C_6$ alkyl, aryl, and heterocyclyl having 1 to 3 N, O, or S atoms.

In another embodiment, the invention relates to compounds of Formula I, wherein $R^1$ is selected from the group consisting of:

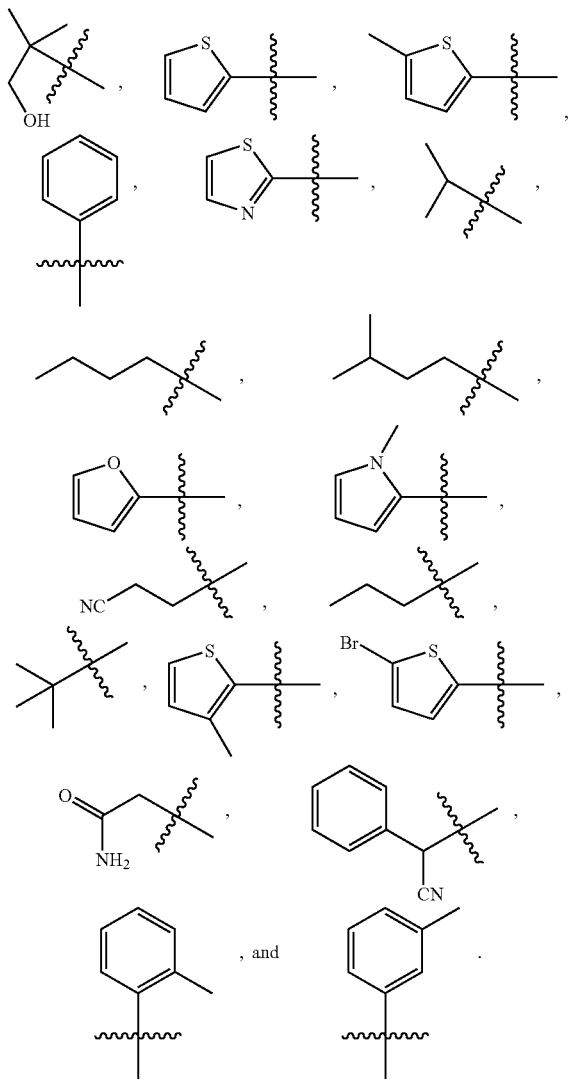

In another embodiment, the invention relates to compounds of the Formula I, wherein $R^2$ is selected from the group consisting of $C_1$-$C_6$ alkyl optionally substituted with $C_6$-$C_{10}$ aryl or $C_3$-$C_8$ cycloalkyl, and $C_3$-$C_9$ heterocyclyl having 1 to 3 N, O, or S atoms and $C_6$-$C_{10}$ aryl. The aryl, cycloalkyl and heterocyclyl are optionally further substituted with $C_1$-$C_6$ alkyl or halo. In a particular embodiment, $R^2$ is selected from the group consisting of:

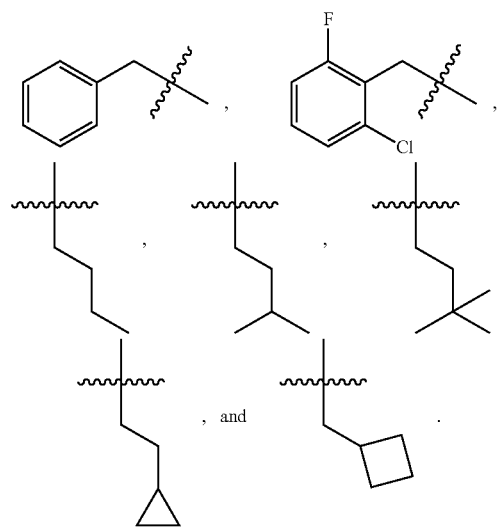

In one aspect of the invention Ring A of Formula I is a 5- or 6-membered aryl or heterocyclyl, optionally substituted with alkyl, -halo, —OH, —O-alkyl, —OCHR$^3$C(O)O-alkyl, —OCHR$^3$C(O)NR$^4$R$^5$, —NHR$^4$, —NR$^4$C(O)-aryl, or —NO$_2$, wherein $R^3$, $R^4$, and $R^5$ are independently —H or $C_1$-$C_6$ alkyl, or $R^4$ and $R^5$ combine with the N atom to which they are attached to form a 5- or 6-membered heterocyclyl ring optionally substituted with —NH$_2$. In a particular embodiment, ring A, together with the ring to which it is fused, is selected from the group consisting of:

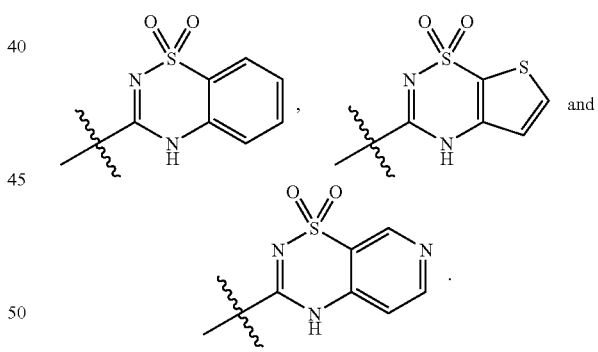

In another embodiment, the invention relates to compounds of the Formula I selected from the group consisting of

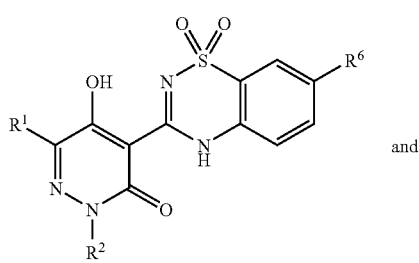

and

-continued

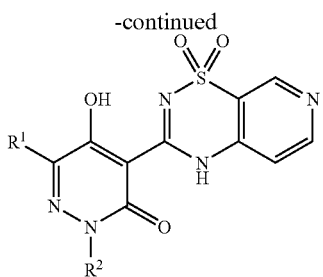

where $R^1$ and $R^2$ are the same as defined immediately above, and $R^6$ is selected from the group consisting of:

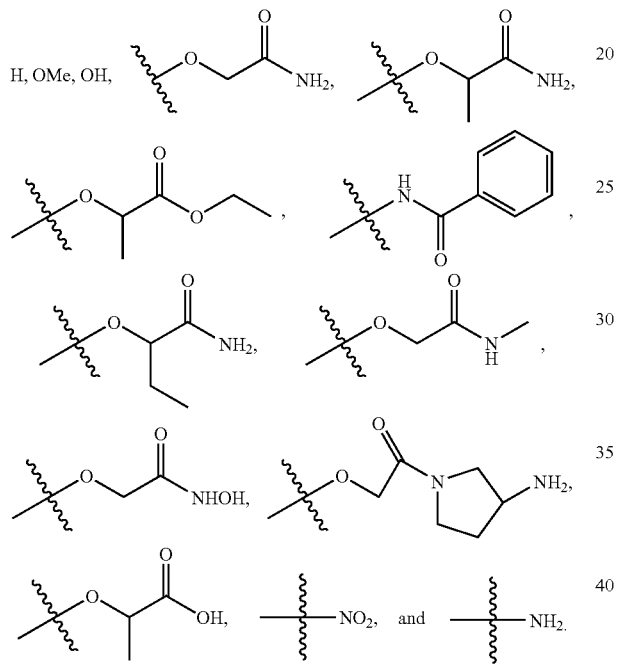

In a preferred embodiment, the invention relates to compounds of Formula I, where $R^1$ is selected from the group consisting of:

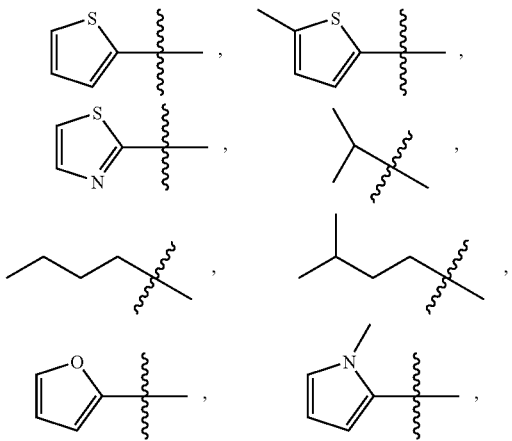

-continued

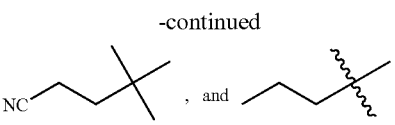

In another preferred embodiment, the invention relates to compounds of Formula I, where $R^2$ is selected from the group consisting of:

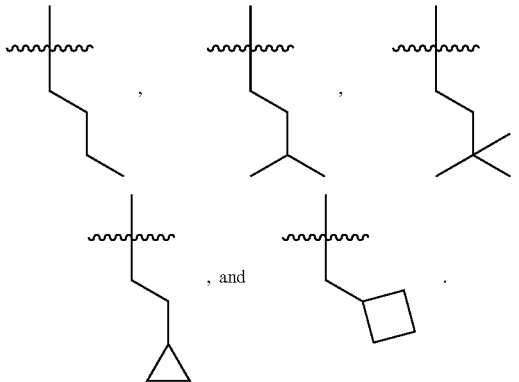

In another preferred embodiment, the invention relates to compounds of Formula I selected from the group consisting of:

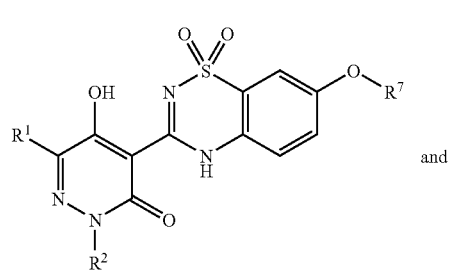

II

III

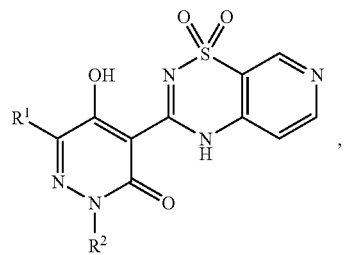

where $R^1$ and $R^2$ are the same as defined immediately above, and $R^7$ is selected from the group consisting of:

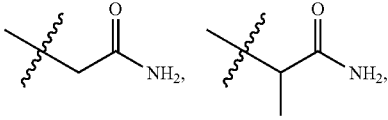

-continued
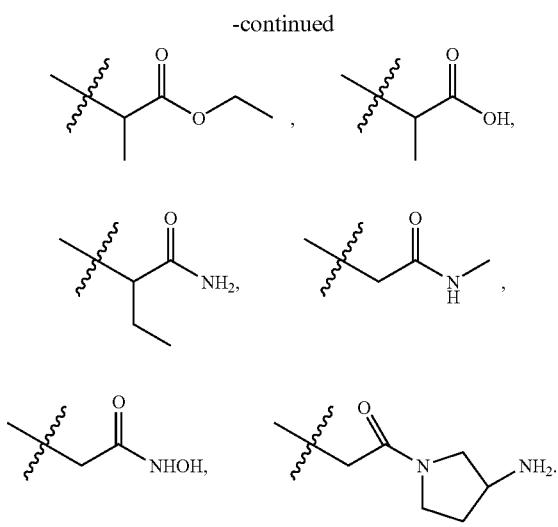
In a particular embodiment, the compound of the invention is selected from the group consisting of:
-continued
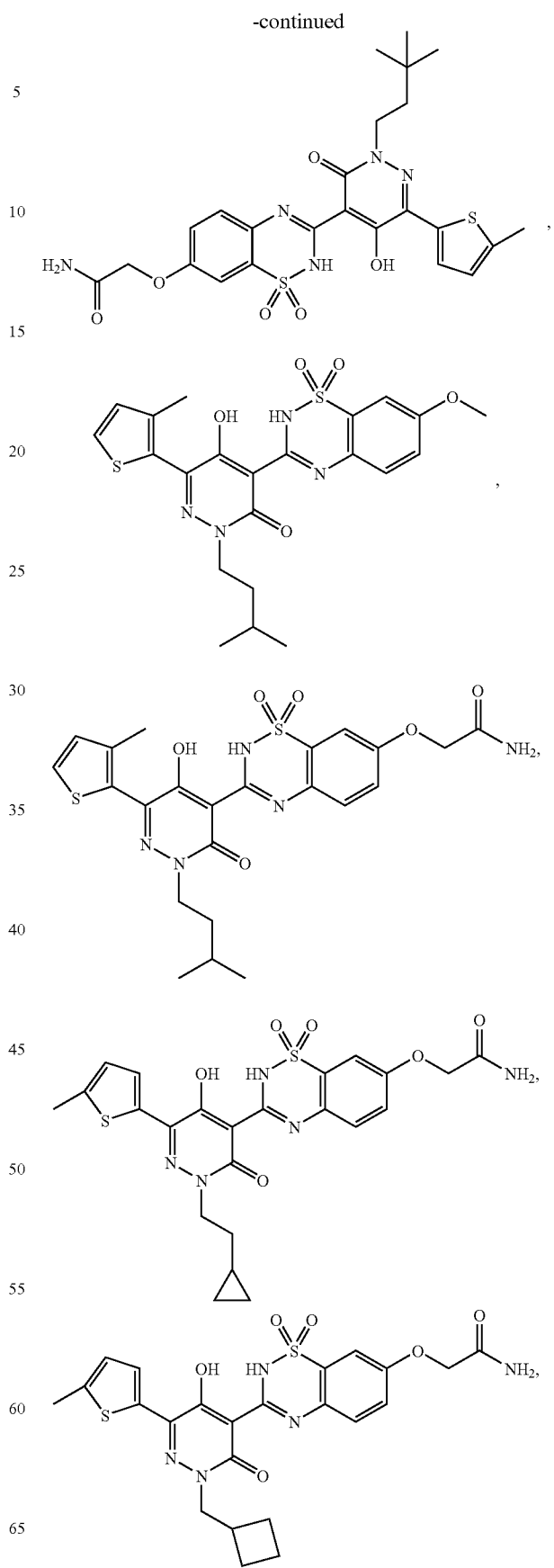

-continued
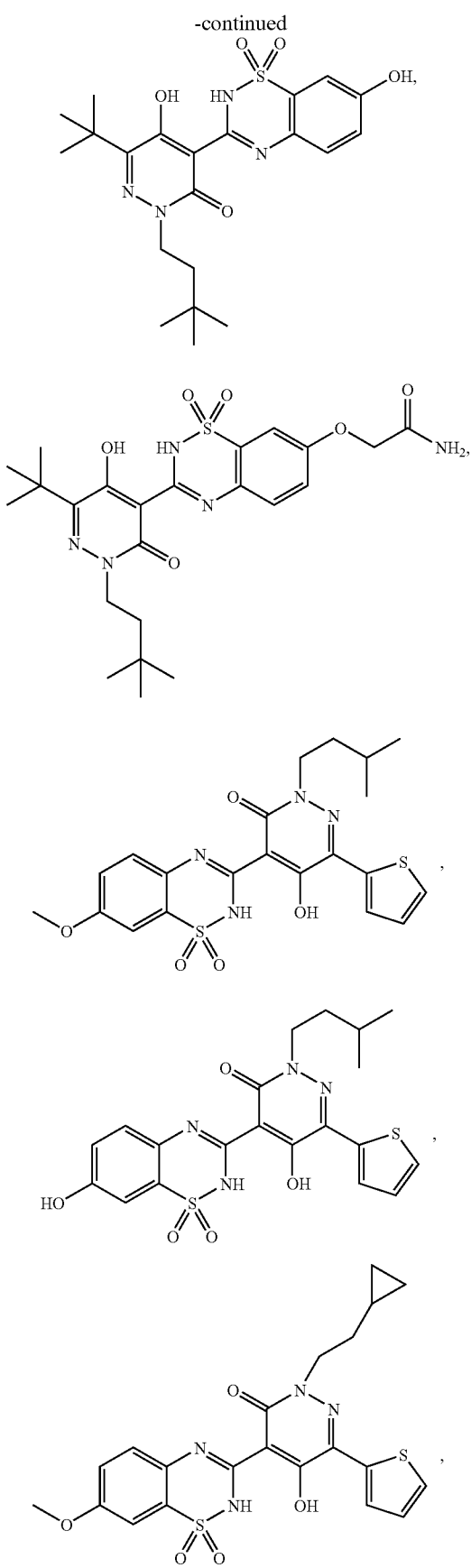
-continued
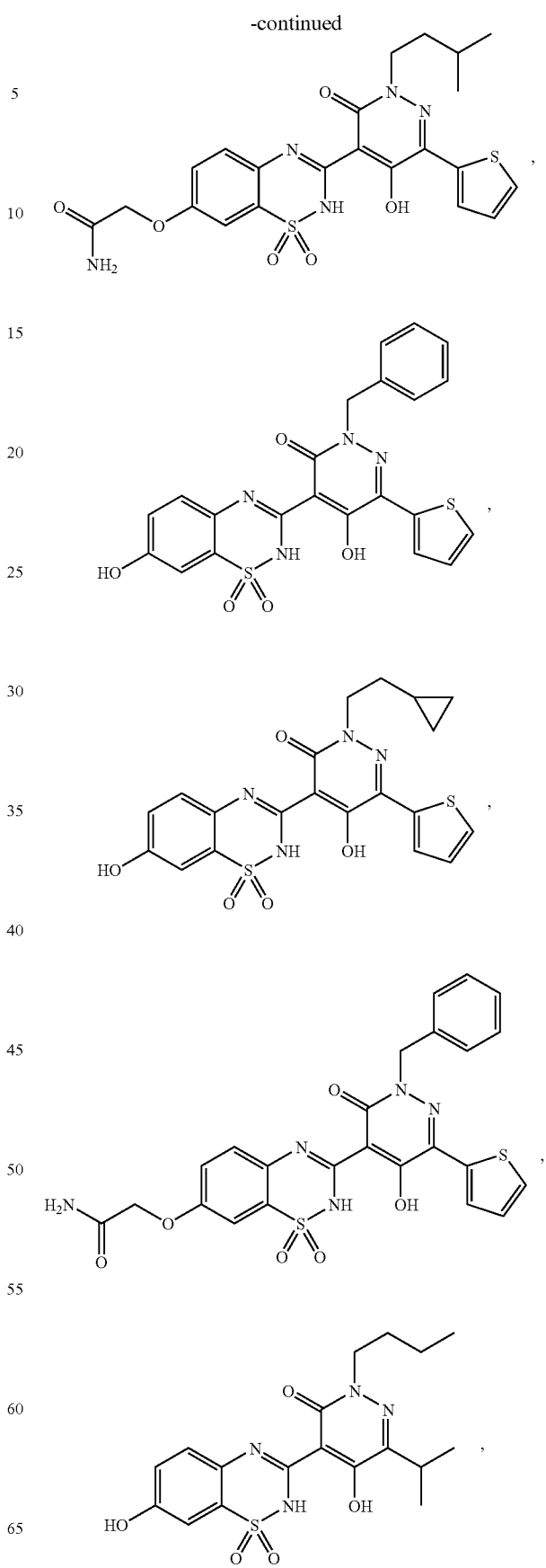

-continued
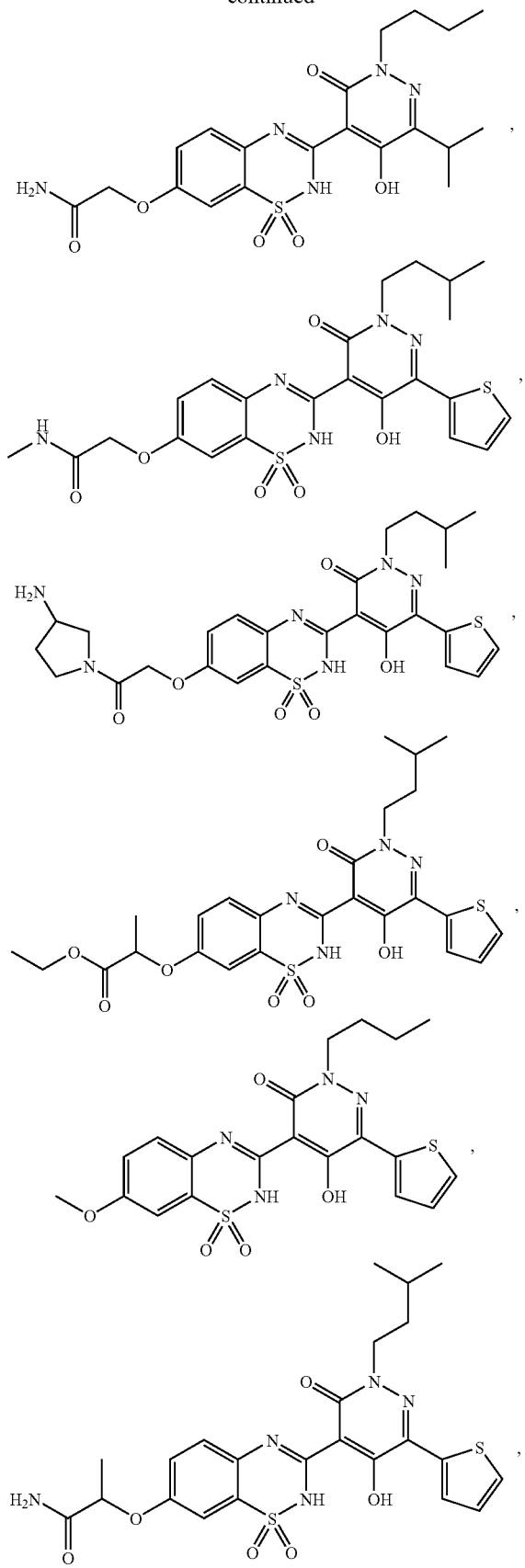
-continued
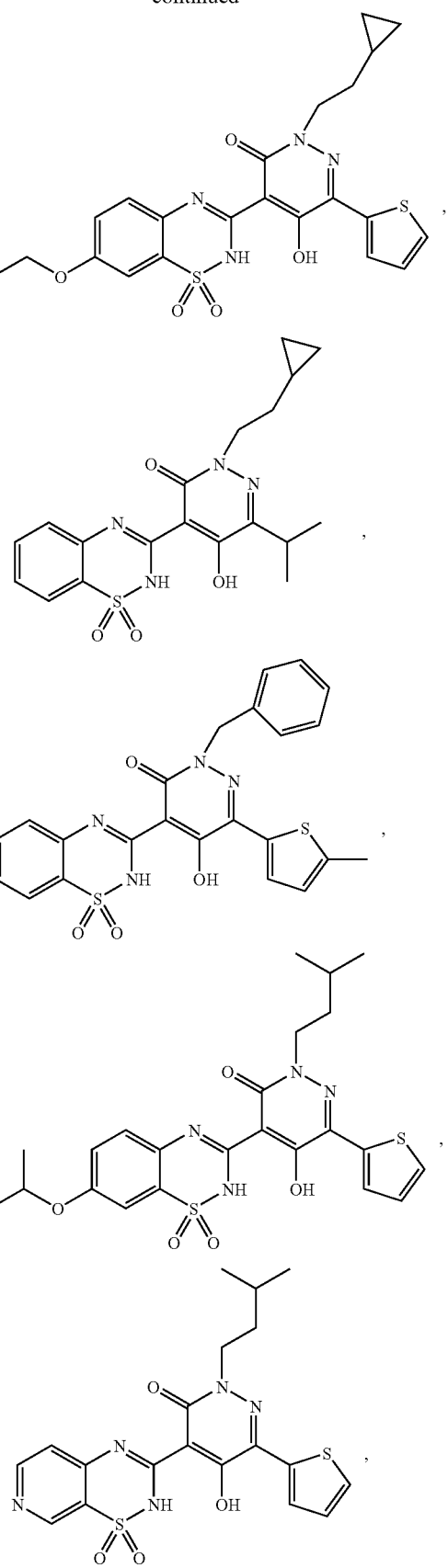

-continued
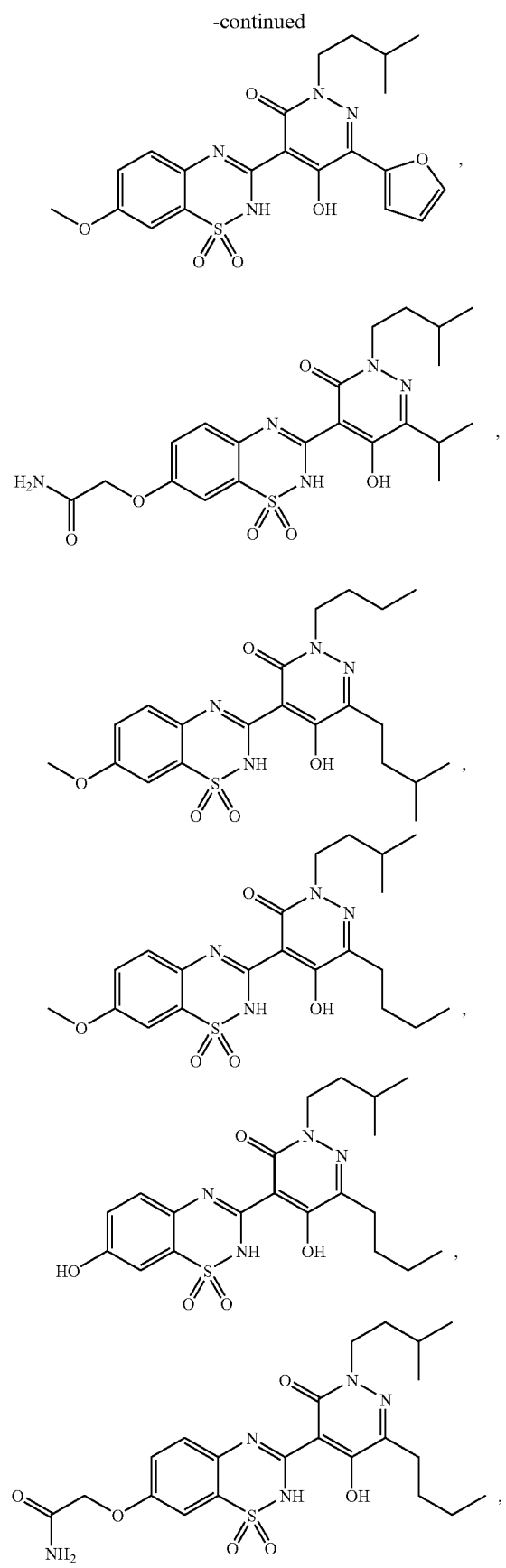
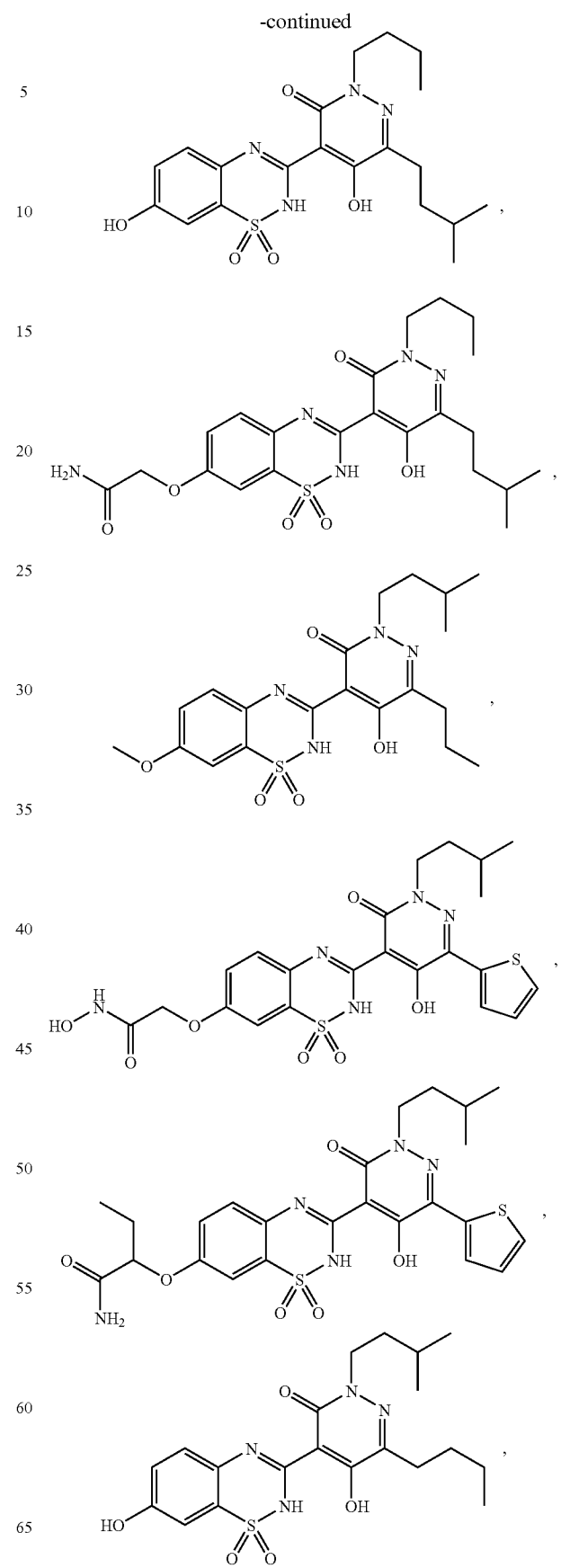

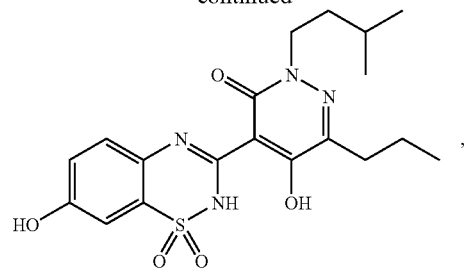
,
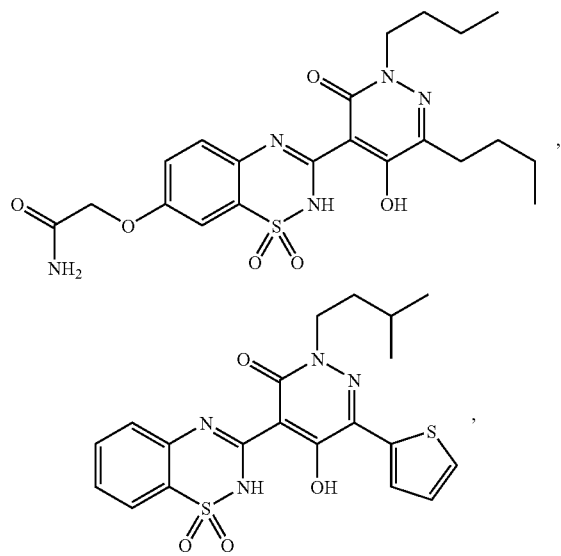
,
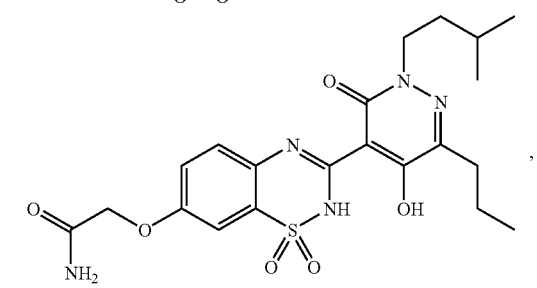
,
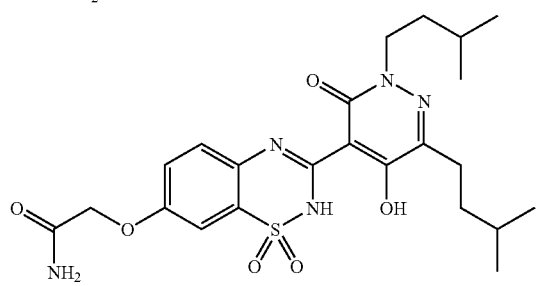
,
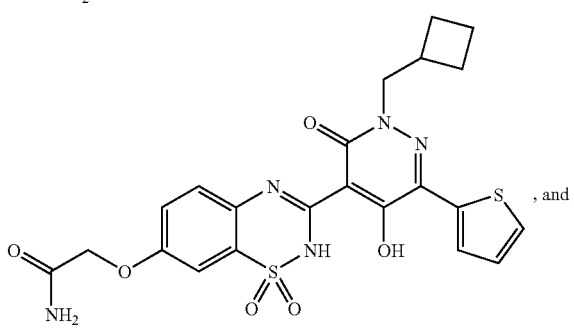
, and
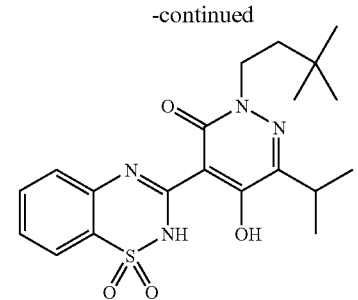
.
In a more preferred embodiment, the invention relates to compounds of Formula I, where $R^2$ is selected from the group consisting of:
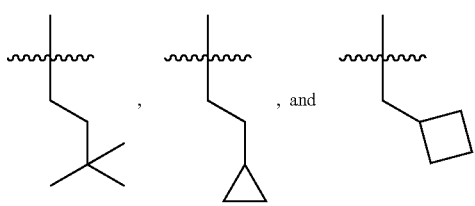
, and .
In another more preferred embodiment, the invention relates to compounds of Formula II:
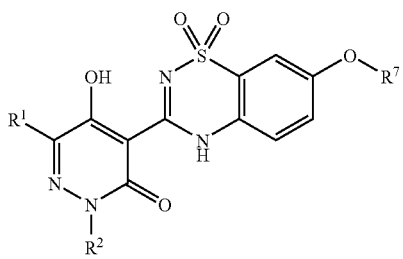
II
where $R^1$ and $R^2$ are the same as defined immediately above, and $R^7$ is selected from the group consisting of:
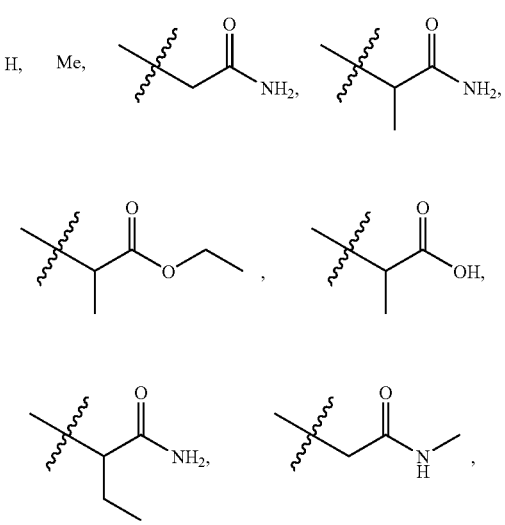

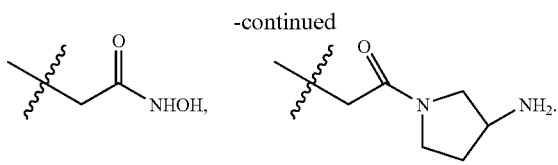

The invention is also directed to pharmaceutically acceptable prodrugs, pharmaceutically active metabolites, pharmaceutically acceptable salts, and pharmaceutically acceptable solvates of the compounds, prodrugs, or metabolites of Formula I. Advantageous methods of making the compounds of Formula I are also described.

In one aspect, the invention encompasses a method for treating or preventing hepatitis C virus infection in a mammal in need thereof, preferably in a human in need thereof, comprising administering to the patient a therapeutically or prophylactically effective amount of a Formula I compound. In one embodiment, the invention encompasses a method for treating or preventing hepatitis C virus infection by administering to a patient in need thereof a therapeutically or prophylactically effective amount of a Formula I compound that is an inhibitor of HCV NS5B polymerase.

In another aspect, the invention encompasses a method for treating or preventing hepatitis C virus infection in a patient in need thereof, comprising administering to the patient a therapeutically or prophylactically effective amount of a compound of Formula I and a pharmaceutically acceptable excipient, carrier, or vehicle.

In another aspect, the invention encompasses a method for treating or preventing hepatitis C virus infection in a patient in need thereof, comprising administering to the patient a therapeutically or prophylactically effective amount of a compound of Formula I and an additional therapeutic agent, preferably an additional antiviral agent or an immunomodulatory agent.

DETAILED DESCRIPTION OF THE INVENTION AND PREFERRED EMBODIMENTS

Where the following terms are used in this specification, they are used as defined below:

The terms "comprising," "having" and "including" are used herein in their open, non-limiting sense.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

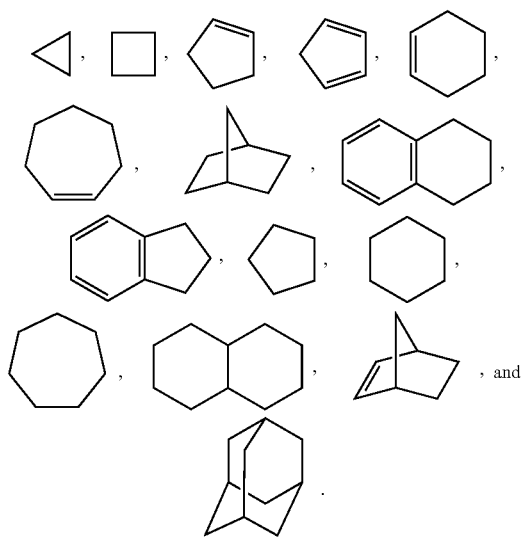

The term "aryl", as used herein, unless otherwise indicated, includes an organic radical derived from an aromatic hydrocarbon by removal of one hydrogen, such as phenyl or naphthyl.

The term "heterocyclic" or "heterocyclyl", as used herein, unless otherwise indicated, includes aromatic (e.g., heteroaryls) and non-aromatic heterocyclic groups containing one to four heteroatoms each selected from O, S and N, wherein each heterocyclic group has from 4-10 atoms in its ring system, and with the proviso that the ring of said group does not contain two adjacent O atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

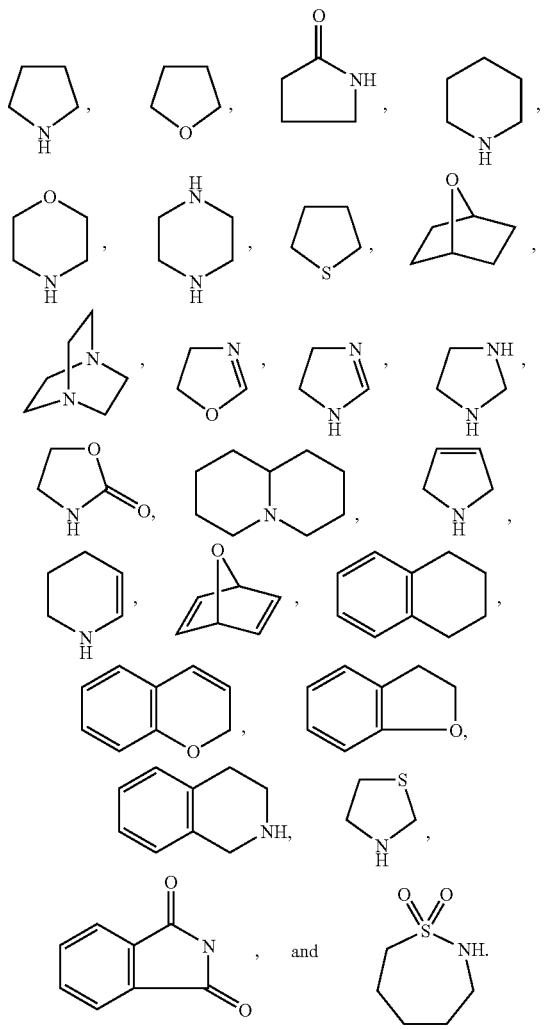

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The terms "α" and "β" indicate the specific stereochemical configuration of a substituent at an asymmetric carbon atom in a chemical structure as drawn.

The compounds of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings. For illustration, and in no way limiting the range of tautomers, the compounds of Formula I may exist as the following:

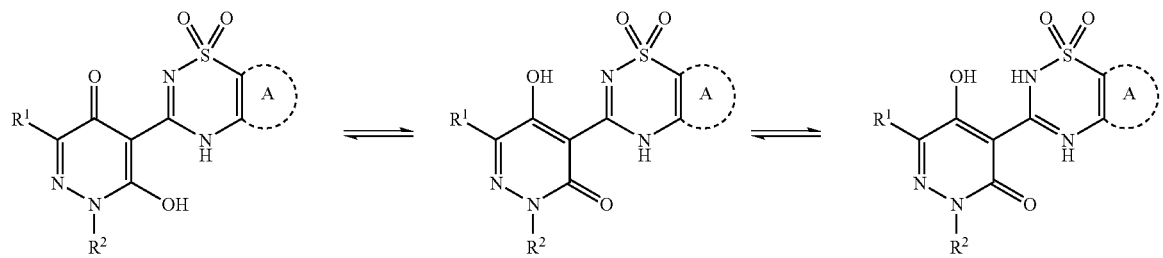

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll receptor-like modulators. In one embodiment the invention encompasses the administration of an additional therapeutic agent that is HCV specific or demonstrates anti-HCV activity.

The Formula I compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®), a clarithromycin (e.g., clarithromycin (Biaxin®)), an erythromycin (e.g., erythromycin (EMycin®)), a penicillin (e.g., penicillin V (V-Cillin K® or PenVee K®)) or a quinolone (e.g., ofloxacin (Floxin®), ciprofloxacin (Cipro®) or norfloxacin (Noroxin®)),aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I compounds of the invention can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, pheneizine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I compounds of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The Formula I compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the α-interferons; β-interferons; adefovir, clevadine, entecavir, pleconaril.

The Formula I compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll receptor-like (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I compounds of the invention can be administered or formulated in combination with an agent which inhibits viral enzymes, including but not limited to inhibitors of HCV protease, such as BILN 2061 and inhibitors of NS5b polymerase such as NM107 and its prodrug NM283 (Idenix Pharmaceuticals, Inc., Cambridge, Mass.).

The Formula I compounds of the invention can be administered or formulated in combination with an agent which inhibits HCV polymerase such as those described in Wu, *Curr Drug Targets Infect Disord.* 2003;3(3):207-19 or in combination with compounds that inhibit the helicase function of the virus such as those described in Bretner M, et al *Nucleosides Nucleotides Nucleic Acids.* 2003;22(5-8):1531, or with inhibitors of other HCV specific targets such as those described in Zhang X., *IDrugs,* 5(2), 154-8 (2002).

The Formula I compounds of the invention can be administered or formulated in combination with an agent which inhibits viral replication. The Formula I compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-$\alpha$, and IFN-$\gamma$).

The Formula I compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I compounds of the invention can be administered or formulated in combination with $\beta$-interferons which include, but are not limited to, interferon $\beta$-1a, interferon $\beta$-1b.

The Formula I compounds of the invention can be administered or formulated in combination with $\alpha$-interferons which include, but are not limited to, interferon $\alpha$-1, interferon $\alpha$-2a (roferon), interferon $\alpha$-2b, intron, Peg-Intron, Pegasys, consensus interferon (infergen) and albuferon.

The Formula I compounds of the invention can be administered or formulated in combination with an absorption enhancer, particularly those which target the lymphatic system, including, but not limited to sodium glycocholate; sodium caprate; N-lauryl-$\beta$-D-maltopyranoside; EDTA; mixed micelle; and those reported in Muranishi *Crit. Rev. Ther. Drug Carrier Syst.*, 7-1-33, which is hereby incorporated by reference in its entirety. Other known absorption enhancers can also be used. Thus, the invention also encompasses a pharmaceutical composition comprising one or more Formula I compounds of the invention and one or more absorption enhancers.

The Formula I compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I compounds of the invention without an additional therapeutic agent.

Pharmaceutical Compositions and Dosage Forms

Pharmaceutical compositions and single unit dosage forms comprising a Formula I compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The Formula I compounds of the invention may also be administered directly to the lung by inhalation. For administration by inhalation, a Formula I compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula I compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a Formula I compound to the lung (see, e.g., Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula I compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a Formula I compound to the lung. Nebulizers create aerosols from liquid drug formulations by using, for example, ultrasonic energy to form fine particles that can be readily inhaled (See e.g., Verschoyle et al., *British J. Cancer*, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver Formula I compounds to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the Formula I compounds formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of Formula I compounds will be known to the skilled artisan and are within the scope of the invention.

Liquid drug formulations suitable for use with nebulizers and liquid spray devices and EHD aerosol devices will typically include a Formula I compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the Formula I compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference) A Formula I compound can also be formulated in rectal or vaginal compositions such as suppositories or retention enemas, e.g., containing conventional suppository bases such as cocoa butter or other glycerides.

In addition to the formulations described previously, a Formula I compound can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver Formula I compounds. Certain organic solvents such as dimethylsulfoxide can also be employed, although usually at the cost of greater toxicity. A Formula I compound can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.,* 1989, 321, 574). In another embodiment, polymeric materials can be used (see *Medical Applications of Controlled Release,* Langer and Wise (eds.), CRC Pres., Boca Raton, Fla. (1974); *Controlled Drug Bioavailability, Drug Product Design and Performance,* Smolen and Ball (eds.), Wiley, New York (1984); Ranger and Peppas, *J. Macromol. Sci. Rev. Macromol. Chem.,* 1983, 23, 61; see also Levy et al., *Science,* 1985, 228, 190; During et al., *Ann. Neurol.,* 1989, 25,351; Howard et al., *J. Neurosurg.,* 71, 105 (1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release, supra,* vol. 2, pp. 115 (1984)). Other controlled-release system can be used (see, e.g. Langer, *Science,* 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I compound useful for the treatment or prevention of a Hepatitis C virus infection. In other embodiments, the invention provides a pharmaceutical pack or kit comprising one or more containers comprising a Formula I compound useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight. Reagents and solvents were purchased from commercial suppliers such as Aldrich Chemical Company and were used without further purification unless otherwise indicated. Tetrahydrofuran (THF) and N,N-dimethylforamide (DMF) were purchased from Aldrich in Sure Seal bottles and used as received.

The reactions set forth below were done generally under a positive pressure of argon or nitrogen at an ambient temperature (unless otherwise stated) in anhydrous solvents. Glassware was oven dried and/or heat dried. The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EM Science), and visualized with UV light (254 nm) and/or heating with commercial ethanolic phosphomolybdic acid. Preparative thin layer chromatography (TLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230-400 mesh silica gel.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed.

When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Mass spectra reported are (+)-ES or APCI (+) LC/MS conducted by the Analytical Chemistry Department of Anadys Pharmaceuticals, Inc.

The described synthetic pathways and experimental procedures utilize many common chemical abbreviations, THF (tetrahydrofuran), DMF (N,N-dimethylformamide), EtOAc (ethyl acetate), DMSO (di-methyl sulfoxide), ACN (acetonitrile), EtOH (ethanol), EDC (1-(3-dimethylaminopropyl)-3-ethylcarbodiimide hydrochloride), HATU (O-(7-azabenzotriazol-1-yl)-1,1,3,3-tetramethyluronium hexafluorophosphate), TFA (trifluoroacetic acid), DIEA (diisopropylethylamine), BOC (tert-butoxycarbonyl), LDA (lithium diisopropyl amine), KO$^t$Bu (potassium tert-butoxide), NaOAc (sodium acetate), NaOEt (sodium ethoxide), Py (pyridine), DBU (1,8-diazabicyclo[5,4,0]undec-7-ene, HBTU (O-benzotriazol-1-yl-N,N,N',N'-tetramethyluronium hexafluoro-phosphate), TEA (triethylamine), MeCN (acetonitrile), MeOH (methanol), DCM (dichloromethane), DMA (dimethyl acetamide), DCC(N,N'-dicyclohexylcarbodiimide), HPLC (high pressure liquid chromatography), TLC (thin layer chromatography), and the like.

Methods 1-6 provide general procedures that may be used to prepare compounds listed in Table 1.

Method 1: Scheme I provides a general procedure that was used to prepare compounds of Formula I.

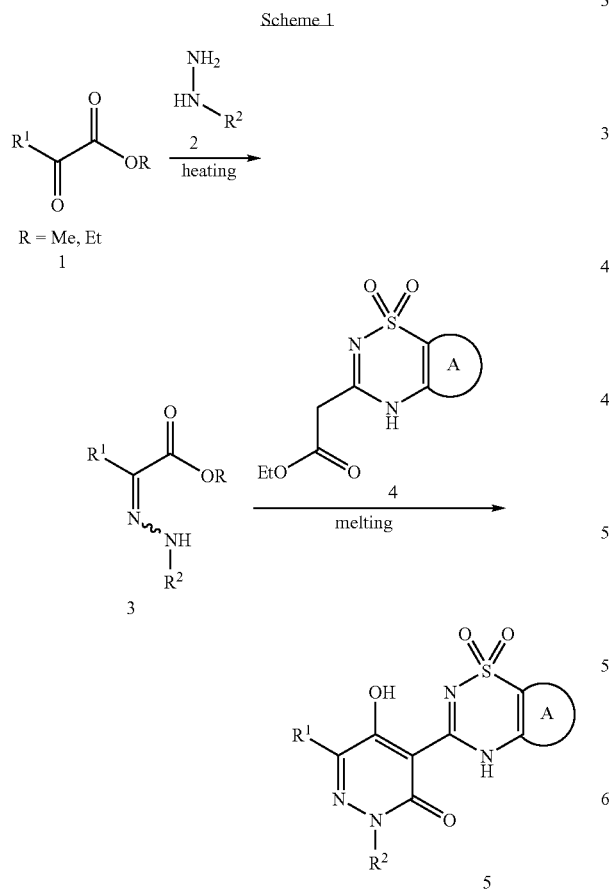

In a typical synthetic route, α-keto-ester 1 can be treated with hydrazine 2 to form hydrazone 3. See, e.g., *J. Heterocyclic Chem.*, 26(3), 619-24 (1989); *Eur. Pat. Appl.*, 331061 (September 1989); *J. Chem Soc. Perkin Trans.* 1: *Organic and Bio-Organic Chem.* (1972-1999), (10), 2721-8 (1988).

Mixing key intermediates of 3 and 4 followed by melting at a temperature in the range of 140-200° C. without solvent can give the desired target molecule 5.

EXAMPLE 1-1

Scheme 1a Describes the Synthesis of Compound 5a

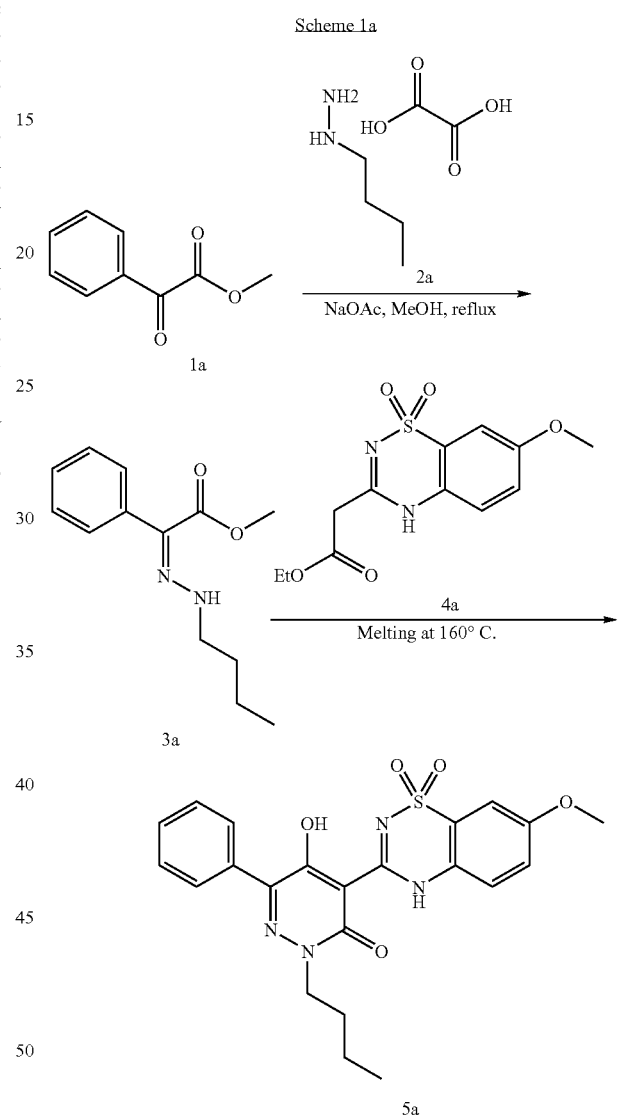

In this specific example, α-keto-ester 1a (2.02 g, 12.3 mmol) was mixed with n-butylhydrazine oxalate (2a) (3.3 g, 18.5 mmol), CH$_3$CO$_2$Na (1.5 g, 18.5 mmol) and 40 mL of MeOH. The mixture was heated to reflux for 1.5 hours. LC-MS analysis of the reaction mixture confirmed the completion of the reaction. The inorganic solid was filtered off and washed with MeOH (20 mL×2). The filtrate was concentrated under reduced vacuum. The liquid-liquid extraction was then performed using EtOAc (30 mL×3) and H$_2$O (20 mL). The organic layer was concentrated and the residue was purified by flash chromatography on silica gel to give the pure desired product (3a) (1.91 g, 66% isolated yield) as yellow oil as a mixture of Z- and E-isomers. LC-MS (ESI$^+$): m/e=235.1 [M+1]$^+$ (exact ms: 234.14). $^1$H NMR (400 MHz, CDCl$_3$): δ

7.22-7.51 (m, 5H), 3.81 (s, 3H, 65%), 3.79 (s, 3H, 35%), 3.55 (t, 2H, 65%, J=7.2 Hz), 3.43 (t, 2H, 35%, J=7.4 Hz), 1.62-1.70 (m, 2H, 65%), 1.49-1.57 (m, 2H, 35%), 1.38-1.47 (m, 2H, 65%), 1.24-1.35 (m, 2H, 35%), 0.97 (t, 3H, 65%, J=7.4 Hz), 0.91 (t, 3H, 35%, J=7.4 Hz).

The reaction condition for this step was described in U.S. Pat. No. 6,355,796, wherein a ketone was reacted with hydroxylamine.

Compound 4a (894.2 mg, 3 mmol) was mixed with the above compound 3a (702.9 mg, 3 mmol). The solid mixture was heated to 160° C. under N$_2$ with stirring for 6 hours. LC-MS indicated incomplete reaction. Extended heating at same temperature for additional 3 h did not improve the conversion. The crude was purified by HPLC purification using a gradient of ACN and water to give the pure desired product (5a) (73.8 mg). Some of the starting material of 4a (213.4 mg) was recovered during the HPLC purification. LC-MS (ESI$^+$): m/e=455.3 [M+1]$^+$ (exact ms: 454.13); $^1$H NMR (400 MHz, CDCl$_3$): δ 7.77-7.79 (m, 2H), 7.45-7.47 (m, 3H), 7.38 (d, 1H, J=2.4 Hz), 7.23 (d, 1H, J=8.8 Hz), 7.19 (dd, 1H, J=9.2 Hz, J$_2$=2.4 Hz), 4.27 (t, 2H, J=7.4 Hz), 3.88 (s, 3H), 1.82-1.89 (m, 2H), 1.38-1.47 (m, 2H), 0.99 (t, 3H, J=7.4 Hz).

Method 2: Scheme 2 provides a general procedure that was used to prepare compounds of Formula I.

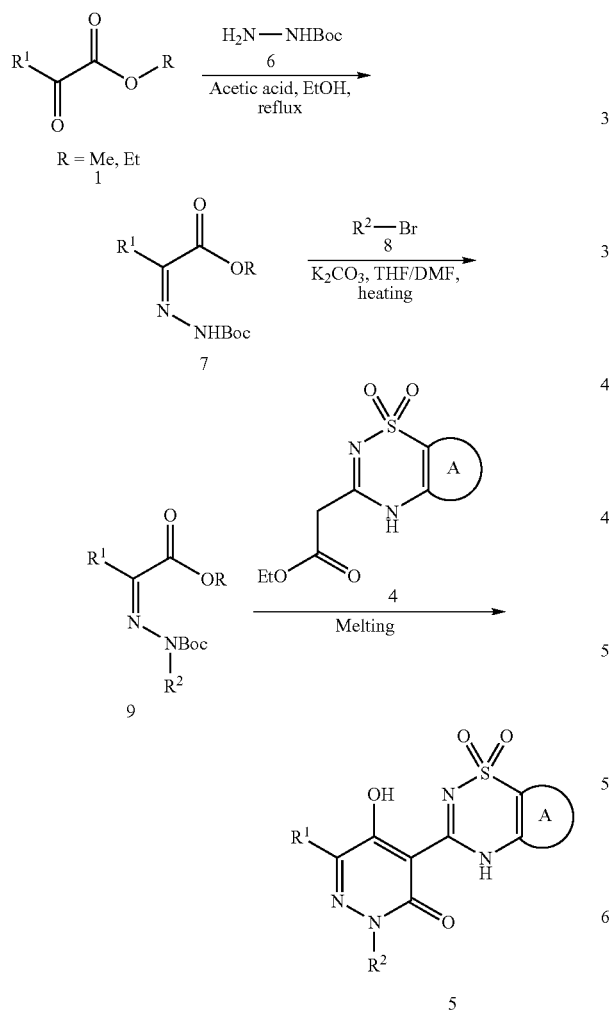

In a typical synthetic route, α-keto-ester 1 is treated with tert-butyl carbazate (6) in the presence of acetic acid under reflux in EtOH to give hydrazone 7. Hydrazone 7 was further alkylated to form the key intermediate 9 by treating with bromide 8 in the presence of base. See Lawton et al., *J. Chem. Soc. Perkin Trans.* 1, 885-897 (1987). Mixing the intermediates of 9 & 4 followed by melting at a temperature in the range of 140-200° C. can give the cyclized product 5.

EXAMPLE 2-1

Scheme 2a Describes the Synthesis of Compound 5b

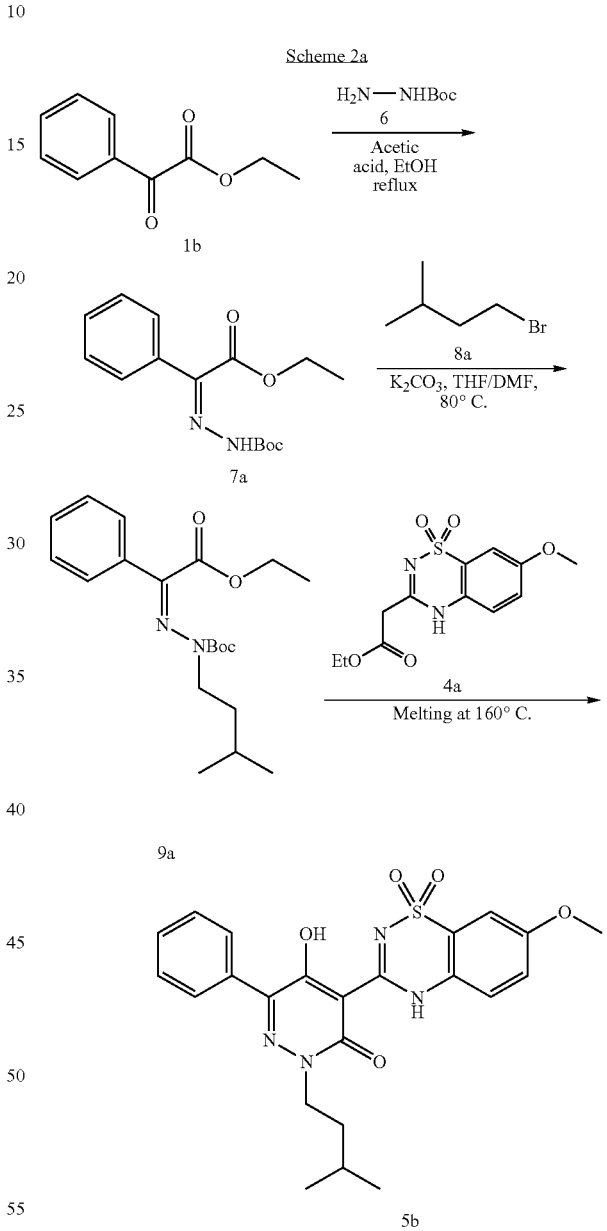

In this specific example, α-keto-ester (1b) (1.0 g, 5.61 mmol) was mixed with tert-butyl carbazate (6) (742 mg, 5.61 mmol), 150 μL of acetic acid and 15 mL of EtOH. The mixture was heated at 60° C. for 3 hours. The LC-MS result confirmed the completion of the reaction and the product (7a) contains the both isomers of E- and Z-form. Upon standing at room temperature, white crystals precipitated from the solution. The top solution was decanted out and the remaining crystals were dried under reduced pressure to give the pure desired product (7a) which was directly used in the next step. LC-MS (ESI$^+$): m/e=293.2 [M+1]$^+$ (exact ms: 292.14).

Hydrazone 7a (949.8 mg, 3.24 mmol) was mixed with isoamylbromide (8a) (390 μL, 3.24 mmol), K$_2$CO$_3$ (2.2 g, 16.2 mmol), DMF (3 mL) and THF (3 mL). The mixture was stirred at 80° C. for 17 hours. The inorganic solid was filtered off and washed with THF. The filtrate was concentrated and the residue was purified by flash chromatography on silica gel to give 440 mg of the desired product 9a in 37.5% isolated yield. LC-MS (ESI$^+$): m/e=363.2 [M+1]$^+$ (exact ms: 362.22).

Compound 9a (285.1 mg, 0.787 mmol) was mixed with compound 4a (235 mg, 0.787 mmol). The solid mixture was heated to 160° C. under N$_2$ for 7 hours. The crude was purified by flash chromatography using a gradient of EtOAc and hexane to give the pure desired product 5b (17.1 mg) as yellow oil. LC-MS (APCI$^+$): m/e=469.2 [M+1]$^+$ (exact ms: 468.13). $^1$H NMR (400 MHz, CDCl$_3$): 7.80-7.82 (m, 2H), 7.47-7.50 (m, 3H), 7.41 (d, 1H, J=2.8 Hz), 7.27 (d, 1H, J=8.8 Hz), 7.22 (1H, dd, J$_1$=9.0 Hz, J$_2$=2.6 Hz), 4.32 (t, 2H, J=7.2 Hz), 3.91 (s, 3H), 1.76-1.81 (m, 2H), 1.66-1.76 (m, 1H), 1.03 (d, 6H, J=6.8 Hz).

EXAMPLE 2-2

Scheme 2b Describes the Synthesis of Compound 5c & 5d 2-(2-Cyclopropyl-ethyl)-5-hydroxy-4-(7-methoxy-1,1-dioxo-1,2-dihydro-1λ$^6$-benzo[1,2,4]thiadiazin-3-yl)-6-thiophen-2-yl-2H-pyridazin-3-one (5c)

In this specific example, compound 9b was made in the same way as that of compound 9a. Compound 9b (654.2 mg) was mixed with compound 4a (533.8 mg) and heated at 160° C. without solvent under N$_2$ atmosphere for 1 h followed by heating at 185° C. for 3 h. The crude product was purified by flash chromatography on silica gel using a gradient of ethyl acetate and hexane (0-100% EtOAc in hexane) to give the desired product 5c (86.5 mg) in 10.2% isolated yield. $^1$H NMR (400 MHz, CDCl$_3$): δ 7.98 (d, 1H, J=3.2 Hz), 7.44 (d, 1H, J=4.8 Hz), 7.41 (d, 1H J=2.4 Hz), 7.19-7.26 (m, 2H), 7.13 (t, 1H, J=4.4 Hz), 4.36 (t, 2H, J=7.0 Hz), 3.90 (s, 3H), 1.78 (q, 2H, J=7.0 Hz), 0.72-0.80 (m, 1H), 0.47-0.51 (m, 2H), 0.065-0.102 (m, 2H); LC-MS (ESI$^+$): m/e=473.1 [M+1]$^+$ (exact MS: 472.09).

2-(2-Cyclopropyl-ethyl)-5-hydroxy-4-(7-hydroxy-1,1-dioxo-1,2-dihydro-1λ$^6$-benzo[1,2,4]thiadiazin-3-yl)-6-thiophen-2-yl-2H-pyridazin-3-one (5d)

Compound 9b (203 mg) was mixed with compound 4b (131.2 mg) and heated at 160° C. without solvent under N$_2$

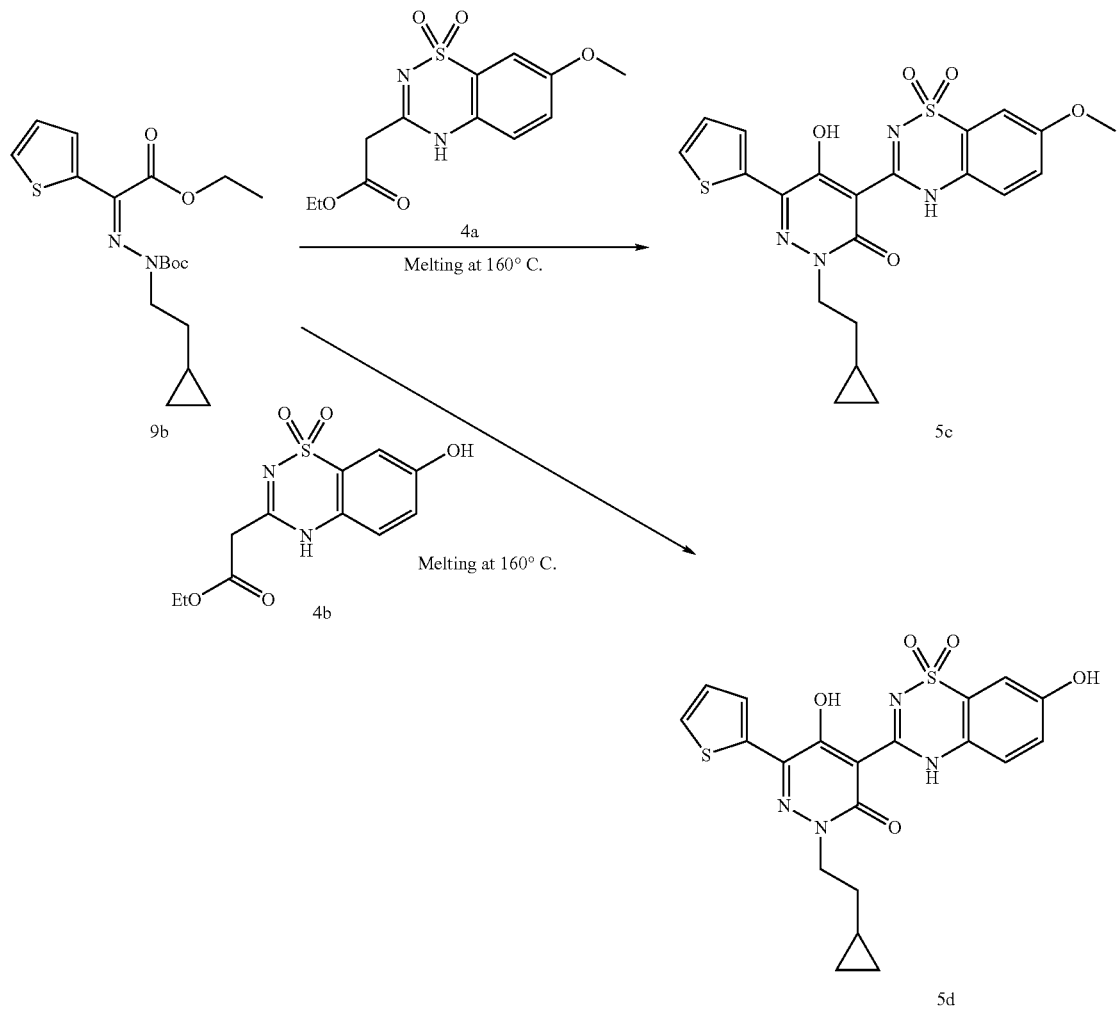

Scheme 2b atmosphere for 4 h. The crude product was purified by flash chromatography on silica gel using a gradient of ethyl acetate and hexane (0-100% EtOAc in hexane) to give the desired product 5d (9.11 mg) in 4.3% isolated yield and recovered starting material of 9b (115.8 mg). $^1$H NMR (400 MHz, DMSO-$d_6$): δ 10.40 (s, br, 1H), 7.91 (d, 1H, J=3.6 Hz), 7.68 (d, 1H, J=4.8 Hz), 7.52 (d, 1H J=9.2 Hz), 7.14-7.17 (m, 3H), 4.23 (t, 2H, J=7.0 Hz), 1.69 (q, 2H, J=7.0 Hz), 0.70-0.80 (m, 1H), 0.38-0.44 (m, 2H), 0.02-0.06 (m, 2H); LC-MS (ESI$^+$): m/e=459.25 [M+1]$^+$ (exact MS: 458.07).

The Following Compounds of Formula I Were Also Made in an Analogous Manner to the Procedure Described in Method 2, Except with the Appropriate Starting Materials.

2-{3-[5-Hydroxy-2-(3-methyl-butyl)-3-oxo-6-thiophen-2-yl-2,3-dihydro-pyridazin-4-yl]-1,1-dioxo-1,2-dihydro-1λ$^6$-benzo[1,2,4]thiadiazin-7-yloxy}-acetamide $^1$H NMR (400 MHz, CD$_3$OD): δ 7.96 (m, 1H), 7.30-7.44 (m, 4H), 7.06-7.08 (m, 1H), 4.58 (s, br, 2H), 4.10-4.26 (m, 2H), 1.62-1.78 (m, 3H), 1.01 (d, 6H, J=6.0 Hz); LC-MS (ESI$^+$): m/e=518.3[M+1]$^+$ (exact MS: 517.11).

2-(2-Cyclopropyl-ethyl)-5-hydroxy-4-(7-methoxy-1,1-dioxo-1,2-dihydro-1λ$^6$-benzo[1,2,4]thiadiazin-3-yl)-6-thiophen-2-yl-2H-pyridazin-3-one $^1$H NMR (400 MHz, CDCl$_3$): δ 7.98 (d, 1H, J=3.2 Hz), 7.44 (d, 1H, J=4.8 Hz), 7.41 (d, 1 H J=2.4 Hz), 7.19-7.26 (m, 2H), 7.13 (t, 1H, J=4.4 Hz), 4.36 (t, 2H, J=7.0 Hz), 3.90 (s, 3H), 1.78 (q, 2H, J=7.0 Hz), 0.72-0.80 (m, 1H), 0.47-0.51 (m, 2H), 0.065-0.102 (m, 2H); LC-MS (ESI$^+$): m/e=473.1 [M+1]$^+$ (exact MS: 472.09).

2-(2-Cyclopropyl-ethyl)-5-hydroxy-4-(7-hydroxy-1,1-dioxo-1,2-dihydro-1λ$^6$-benzo[1,2,4]thiadiazin-3-yl)-6-thiophen-2-yl-2H-pyridazin-3-one $^1$H NMR (400 MHz, DMSO-$d_6$): δ 10.40 (s, br, 1H), 7.91 (d, 1H, J=3.6 Hz), 7.68 (d, 1H, J=4.8 Hz), 7.52 (d, 1H J=9.2 Hz), 7.14-7.17 (m, 3H), 4.23 (t, 2H, J=7.0 Hz), 1.69 (q, 2H, J=7.0 Hz), 0.70-0.80 (m, 1H), 0.38-0.44 (m, 2H), 0.02-0.06 (m, 2H); LC-MS (ESI$^+$): m/e=459.25 [M+1]$^+$ (exact MS: 458.07).

2-Benzyl-5-hydroxy-4-(7-methoxy-1,1-dioxo-1,2-dihydro-1λ$^6$-benzo[1,2,4]thiadiazin-3-yl)-6-phenyl-2H-pyridazin-3-one $^1$H NMR (400 MHz, CDCl$_3$): δ 7.99-8.02 (m, 1H), 7.40-7.45 (m, 2H), 7.26-7.38 (m, 4H), 7.16-7.24 (m, 3H), 7.13-7.15 (m, 1H), 5.42 (s, 2H), 3.91 (s, 3H); LC-MS (ESI$^+$): m/e=495.1 [M+1]$^+$ (exact MS: 494.07).

2-Benzyl-5-hydroxy-4-(7-hydroxy-1,1-dioxo-1,2-dihydro-1λ$^6$-benzo[1,2,4]thiadiazin-3-yl)-6-thiophen-2-yl-2H-pyridazin-3-one $^1$H NMR (400 MHz, DMSO-$d_6$): δ 7.90 (dd, 1H, J$_1$=4.0 Hz, J$_2$=1.2 Hz), 7.66 (m, 1H), 7.45 (d, 1H, J=9.2 Hz), 7.24-7.38 (m, 5H), 7.10-7.16 (m, 3H), 5.32 (s, 2H); LC-MS (ESI$^+$): m/e=481.0 [M+1]$^+$ (exact MS: 480.06).

2-[3-(2-Benzyl-5-hydroxy-3-oxo-6-thiophen-2-yl-2,3-dihydro-pyridazin-4-yl)-1,1-dioxo-1,2-dihydro-1λ$^6$-benzo[1,2,4]thiadiazin-7-yloxy]-acetamide $^1$H NMR (400 MHz, DMSO-$d_6$): δ 7.90 (dd, 1H, J=3.6 Hz, J$_2$=0.8 Hz), 7.67 (d, 1H, J=5.2 Hz), 7.61 (s, br, 1H), 7.57 (d, 1H, J=8.8 Hz), 7.25-7.41 (m, 6H), 7.15 (dd, 1H, J$_1$=4.4 Hz, J$_2$=3.6 Hz), 5.33 (s, 2H), 4.56 (s, 2H); LC-MS (ESI$^+$): m/e=538.1[M+1]$^+$ (exact MS: 537.08).

2-(2-Chloro-6-fluoro-benzyl)-5-hydroxy-4-(7-methoxy-1,1-dioxo-1,2-dihydro-1λ$^6$-benzo[1,2,4]thiadiazin-3-yl)-6-thiophen-2-yl-2H-pyridazin-3-one $^1$H NMR (400 MHz, CDCl$_3$): δ 7.85-7.90 (m, 1H), 7.18-7.44 (m, 5H), 7.03-7.12 (m, 3H), 5.58 (s, 2H), 3.91 (s, 3H); LC-MS (ESI$^+$): m/e=547.2 [M+1]$^+$ (exact MS: 546.02).

2-(2-Chloro-6-fluoro-benzyl)-5-hydroxy-4-(7-hydroxy-1,1-dioxo-1,2-dihydro-1λ$^6$-benzo[1,2,4]thiadiazin-3-yl)-6-thiophen-2-yl-2H-pyridazin-3-one $^1$H NMR (400 MHz, DMSO-$d_6$): δ 10.2 (s, br, 1H), 7.70 (d, 1H, J=3.2 Hz), 7.53 (d, 1H, J=4.4 Hz), 7.41-7.46 (m, 1H), 7.37 (d, 2H, J=8 Hz), 7.27 (t, 1H, J=8 Hz), 7.04-7.10 (m, 3H), 5.38 (s, 2H); LC-MS (ESI$^+$): m/e=533.04 [M+1]$^+$ (exact MS: 532.01).

5-Hydroxy-4-(7-methoxy-1,1-dioxo-1,2-dihydro-1λ$^6$-benzo[1,2,4]thiadiazin-3-yl)-2-(3-methyl-butyl)-6-(1-methyl-1H-pyrrol-2-yl)-2H-pyridazin-3-one LC-MS (ESI$^+$): m/e=472.30 [M+1]$^+$ (exact ms: 471.16); $^1$H NMR (400 MHz, CDCl$_3$): δ 7.42 (d, 1H, J=2.8 Hz), 7.27 (m, 1H), 7.21 (m, 1H), 6.92 (dd, 1H, J=3.6, 2.0 Hz), 6.81 (t, 1H, J=2.0 Hz), 6.26 (m, 1H), 4.28 (m, 2H), 3.92 (s, 3H), 3.84 (s, 3H), 1.75 (m, 3H), 1.01 (d, 6H, J=6.4 Hz).

Method 3: Scheme 3 provides a general procedure that was used to prepare compounds of Formula I.

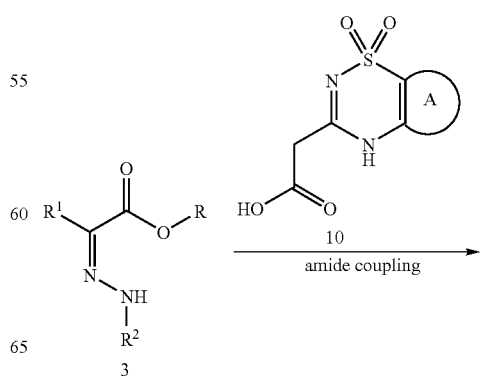

Scheme 3

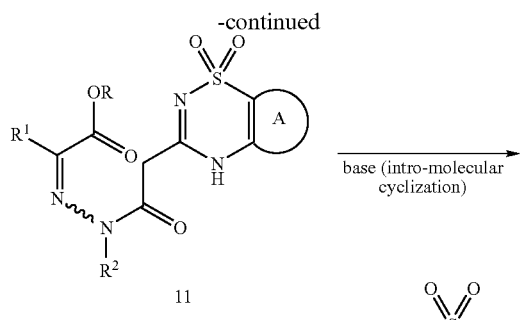

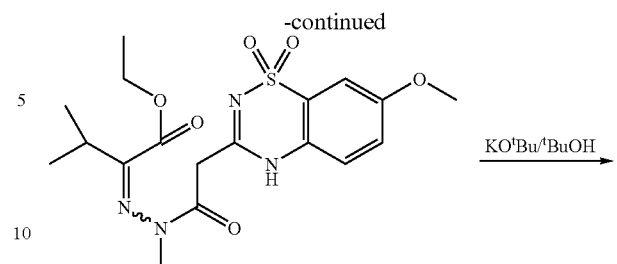

In the synthetic route shown in Scheme 3, hydrazone 3 can be treated with carboxylic acid 10 or with in-situ activated 10 by adding activating reagents such as HBTU, HATU, DCC or via acid chloride intermediate or other amide coupling methods known in the art to form key intermediate 11. See, e.g., Lawton et al., *J. Chem. Soc. Perkin Trans.* 1, 885-897 (1987). Compound 11 can be transformed to the title compound 5 via intra-molecular cyclization using base such as, but not limited to, NaOEt, KO$^t$Bu, KOH, NaH, or LDA.

EXAMPLE 3-1

Scheme 3a describes the synthesis of compounds of 5e, 5f and 5g

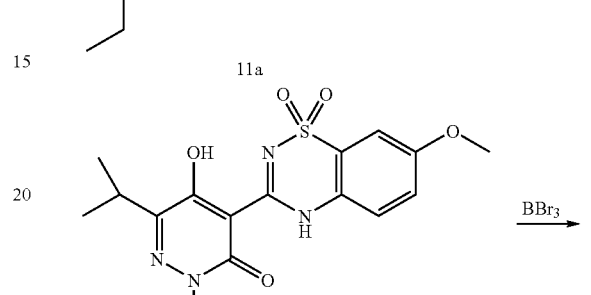

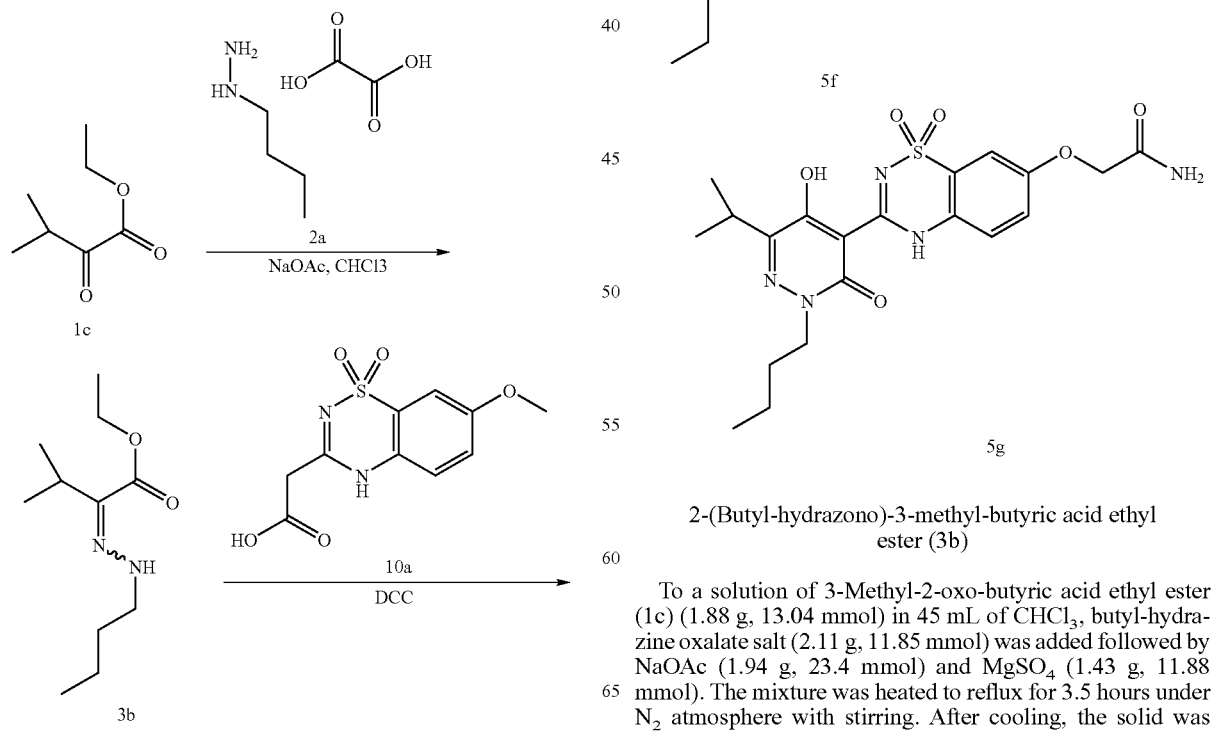

2-(Butyl-hydrazono)-3-methyl-butyric acid ethyl ester (3b)

To a solution of 3-Methyl-2-oxo-butyric acid ethyl ester (1c) (1.88 g, 13.04 mmol) in 45 mL of CHCl$_3$, butyl-hydrazine oxalate salt (2.11 g, 11.85 mmol) was added followed by NaOAc (1.94 g, 23.4 mmol) and MgSO$_4$ (1.43 g, 11.88 mmol). The mixture was heated to reflux for 3.5 hours under N$_2$ atmosphere with stirring. After cooling, the solid was filtered off and the filtrate was concentrated under reduced vacuum. The residue was first cleaned by an extraction between EtOAc (50 mL×3) and H₂O (20 mL). The organic layer was concentrated under reduced pressure and dried under high vacuum overnight to give 2.17 g of the crude product (3b) in 85.4% yield as a mixture of the E- and Z-isomers. This crude product was directly used in the next step without further purification. LC-MS (ESI⁺): m/e=215.4 [M+1]⁺, 237.1 [M+Na]⁺ (exact ms: 214.17).

2-{Butyl-[2-(7-methoxy-1,1-dioxo-1,4-dihydro-1l6-benzo[1,2,4]thiadiazin-3-yl)-acetyl]-hydrazono}-3-methyl-butyric acid ethyl ester (11a)

To a solution of 2-(Butyl-hydrazono)-3-methyl-butyric acid ethyl ester (3b) (79 mg, 0.37 mmol) and (1,1-Dioxo-1,4-dihydro-1l6-benzo[1,2,4]thiadiazin-3-yl)-acetic acid (10a) (100 mg) in 0.4 mL of anhydrous DMF and 2 mL of anhydrous methylene chloride, a solution of 1,3-dicyclohexyl-carbodiimide (DCC) (76.3 mg) in 0.4 mL of methylene chloride was added and the resulted mixture was stirred at room temperature overnight. The solid was filtered off and the filtrate was concentrated under reduced pressure, H₂O (10 mL) was added, extracted with EtOAc (20 mL×3). The crude product was then purified by flash chromatography on silica gel to give the desired product (11a) (102.8 mg) and further cyclized product (5e) (9.5 mg) in total yield of 65.7%. LC-MS (ESI⁺): m/e=467.0 [M+1]⁺ (exact ms: 466.19).

2-Butyl-5-hydroxy-6-isopropyl-4-(7-methoxy-1,1-dioxo-1,2-dihydro-1λ⁶-benzo[1,2,4]thiadiazin-3-yl)-2H-pyridazin-3-one (5e)

To a solution of 2-{Butyl-[2-(7-methoxy-1,1-dioxo-1,4-dihydro-1l6-benzo[1,2,4]thiadiazin-3-yl)-acetyl]-hydrazono}-3-methyl-butyric acid ethyl ester (11a) (68.9 mg, 148 µmol) in 1.1 mL of tert-butanol, 1.0 M of KO$^t$Bu in tert-butanol (370 µL, 370 µmol) and the resulted mixture was shaken at room temperature for 2 hours. The reaction mixture was quenched with 1.0 M HCL in H₂O (370 µL), added 3 mL of brine, extracted with methylene chloride (5 mL×2) and EtOAc (5 mL×3), dried over MgSO₄, filtered, concentrated in vacuo and further purified by flash chromatography on silica gel to give the desired product (5e) (37.1 mg) in 59.6% yield. This product was made in multiple batches and the isolated yield ranged from 59% to 81%. LC-MS (ESI⁺): m/e=421.1 [M+1]⁺ (exact ms: 420.15). ¹H NMR (400 MHz, CDCl₃): δ7.39-7.40 (m, 1H), 7.17-7.26 (m, 2H), 4.19 (t, 2H, J=7.2 Hz), 3.90 (s, 3H), 3.32 (m, J=6.8 Hz, 1H), 1.80 (m, 2H, J=7.6 Hz), 1.40 (m, 2H, J=7.6 Hz), 1.27 (d, 6H, J=6.8 Hz), 0.99 (t, 3H, J=7.4 Hz).

2-Butyl-5-hydroxy-4-(7-hydroxy-1,1-dioxo-1,2-dihydro-1λ⁶-benzo[1,2,4]thiadiazin-3-yl)-6-isopropyl-2H-pyridazin-3-one (5f)

2-Butyl-5-hydroxy-6-isopropyl-4-(7-methoxy-1,1-dioxo-1,2-dihydro-1λ⁶-benzo[1,2,4]thiadiazin-3-yl)-2H-pyridazin-3-one (5e) (56 mg) was dissolved in 3 mL of methylene chloride. BBr₃ (466 µL, 1.0 M in methylene chloride) was added and the mixture was stirred at room temperature for 1.5 hours. LC-MS result showed the incompletion of the reaction. BBr₃ (0.5 mL, 1.0 M) was added and the reaction mixture was continued to shake at room temperature overnight. LC-MS confirmed that the reaction was close to completion. The reaction mixture was poured onto ice (10 mL), extracted with CHCl₃ (20 mL×3). The organic layer was dried over MgSO₄, filtered, concentrated under reduced pressure and further purified by flash chromatography on silica gel to give the desired product (5f) (42.2 mg) in 78.0% yield. ¹H NMR (400 MHz, CDCl₃): δ 7.46 (d, 1H, J=2.8 Hz), 7.16-7.26 (m, 2 H), 4.20 (t, 2H, J=7.2 Hz), 3.34 (m, J=6.8 Hz, 1H), 1.81 (m, 2H), 1.41 (m, 2H), 1.29 (d, 6H, J=6.8 Hz), 1.00 (t, 3H, J=7.4 Hz); LC-MS (ESI⁺): m/e=407.1 [M+1]⁺ (exact MS: 406.13).

2-[3-(2-Butyl-5-hydroxy-6-isopropyl-3-oxo-2,3-dihydro-pyridazin-4-yl)-1,1-dioxo-1,2-dihydro-1λ⁶-benzo[1,2,4]thiadiazin-7-yloxy]-acetamide (5g)

To a solution of 2-Butyl-5-hydroxy-4-(7-hydroxy-1,1-dioxo-1,2-dihydro-1λ⁶-benzo[1,2,4]thiadiazin-3-yl)-6-isopropyl-2H-pyridazin-3-one (5f) (38.7 mg, 95.2 µmol) in anhydrous DMF (4 mL), 2-Bromo-acetamide (14.5 mg, 104.7 µmol) was added followed by K₂CO₃ (39.5 mg, 285.6 µmol). The resulted mixture was heated at 80° C. overnight with stirring. The reaction mixture was concentrated under reduced vacuum and the residue was purified by flash chromatography on silica gel to give the desired product (5g) (21.7 mg) in 49.2% yield. ¹H NMR (400 MHz, DMSO-d₆): δ7.63-7.66 (m, 1H), 7.62 (br, 1 H), 7.40 (br, 1H), 7.34-7.39 (m, 2 H), 4.58 (s, 2H), 4.10 (m, 2H), 3.23 (m, 1H, J=6.8 Hz), 1.72 (m, 2H, J=7.2 Hz), 1.32 (m, 2H. J=7.2 Hz), 1.21 (d, 6H, J=6.4 Hz), 0.91 (t, 3H, J=7.2 Hz); LC-MS (ESI⁺): m/e=464.1-[M+1]⁺ (exact MS: 463.15).

EXAMPLE 3-2

Scheme 3b Describes the Synthesis of Compounds of 5j and 5k

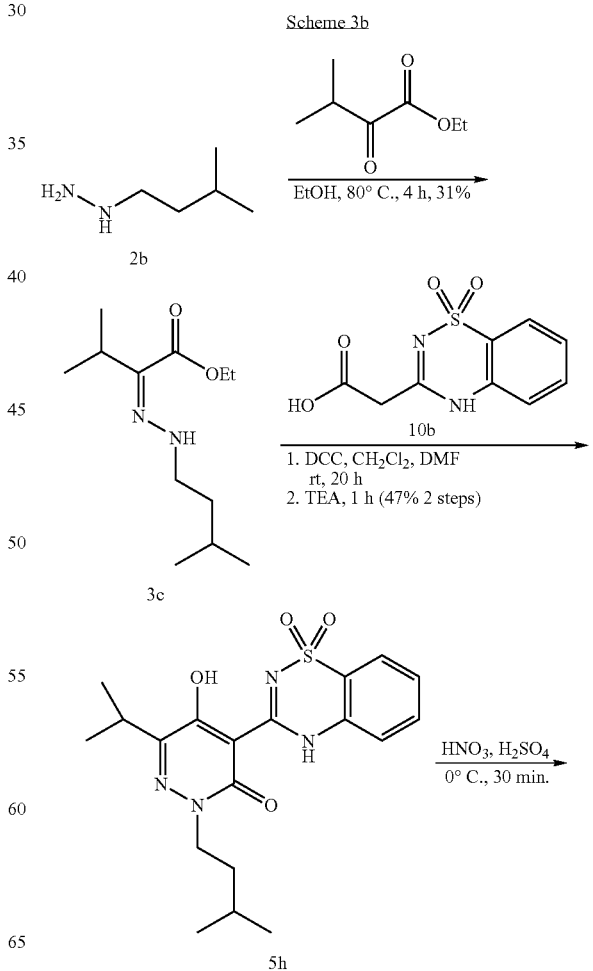

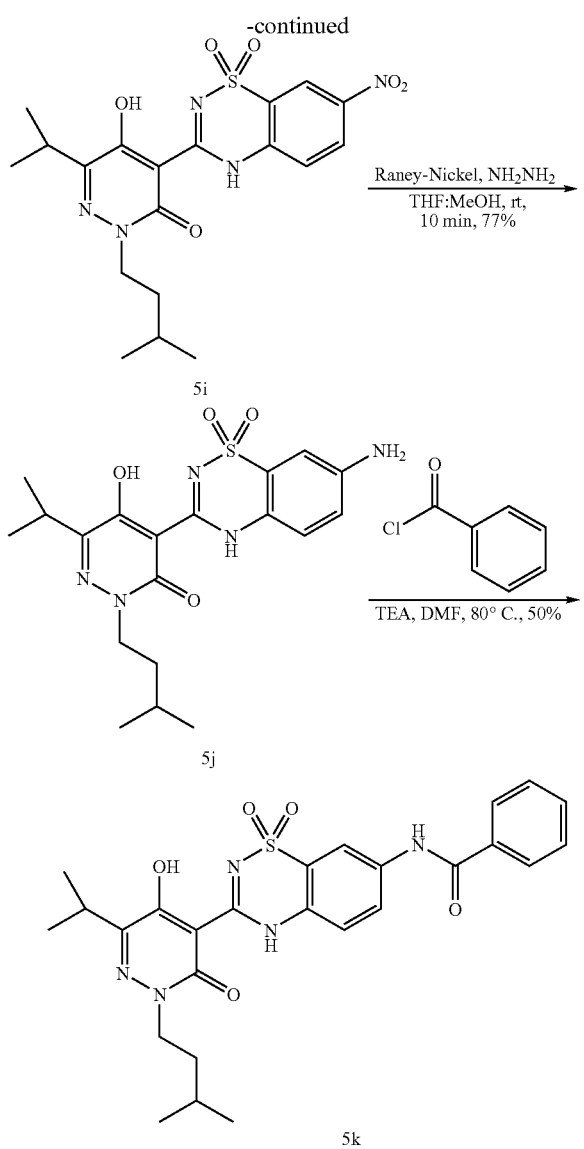

3-Methyl-2-[(3-methyl-butyl)-hydrazono]-butyric acid ethyl ester (3c)

To a solution of 2b (2.00 g, 10.4 mmol) dissolved in EtOH (55 mL) was added ethyl-3-methyl-2-oxobutyrate (1c) (1.7 mL, 1.1 mmol). The solution was heated 4 h at 80° C., cooled to room temperature, and concentrated in vacuo. The crude mixture was dissolved in H$_2$O (100 mL) and extracted with EtOAc (100 mL). The organic layer was dried over MgSO$_4$ and concentrated in vacuo. The crude mixture was purified by flash chromatography on silica gel (0-6% EtOAc/hexanes) to give 3c (1.0 g, 43%) as a clear oil. LC-MS (ESI$^+$) m/e 229 [M+H]$^+$ (exact MS: 228.18).

4-(1,1-Dioxo-1,4-dihydro-1λ$^6$-benzo[1,2,4]thiadiazin-3-yl)-5-hydroxy-6-isopropyl-2-(3-methyl-butyl)-1,6-dihydro-2H-pyridazin-3-one (5h)

N,N'-Dicyclohexylcarbodiimide (0.447 g, 2.17 mmol), compound 10b (0.520 g, 2.17 mmol), and 3c (0.494 g, 2.17 mmol) were dissolved in CH$_2$Cl$_2$ (12 mL) and DMF (2 mL). After stirring at room temperature overnight, triethylamine (0.95 mL, 6.83 mmol) was added to the solution. After stirring 90 min at room temperature, the reaction mixture was filtered, and concentrated in vacuo. The reaction mixture was purified by flash chromatography on silica gel (0-5% MeOH/CH$_2$Cl$_2$) to give 5h (0.413 g, 47%) as a white solid. $^1$H NMR (400 MHz, D$_6$-DMSO) δ 9.91 (br s, 1 H), 7.90 (d, J=10 Hz, 1 H), 7.75 (t, J=8 Hz, 1 H), 7.63 (d, J=10 Hz, 1 H), 7.54 (t, J=10 Hz, 1 H), 4.14 (m, 2 H), 3.32 (t, J=8 Hz, 2 H), 1.65-1.55 (m, 2 H), 1.15 (d, J=8 Hz, 6 H), 0.87 (d, J=6.4 Hz, 6 H). MS (ESI$^+$) m/e 405 [M+H]$^+$.

5-Hydroxy-6-isopropyl-2-(3-methyl-butyl)-4-(7-nitro-1,1-dioxo-1,4-dihydro-1λ$^6$-benzo[1,2,4]thiadiazin-3-yl)-2H-pyridazin-3-one (5i)

To a solution of 5h (0.097 g, 0.025 mmol) in conc H$_2$SO$_4$ (0.65 mL) cooled on ice bath was added conc HNO$_3$ (0.10 mL). After stirring 30 min at 0° C., the reaction mixture was poured onto crushed ice (1.5 g). The resulting precipitate was collected by filtration to give 5i (0.091 g, 85%) as a yellow solid. $^1$H NMR (400 MHz, D$_6$-DMSO) δ 13.90 (s, 1 H), 8.57 (d, J=2.8 Hz, 1 H), 8.49 (dd, J=9.2, 2.8 Hz, 1 H), 7.82 (d, J=8.8 Hz, 1 H), 4.11 (t, J=6.8 Hz, 2 H), 3.23 (m, 2 H), 1.61 (m, 2 H), 1.21 (d, J=8 Hz, 6 H), 0.93 (d, J=8 Hz, 6 H). MS (ESI$^+$) m/e 450 [M+H]$^+$.

4-(7-Amino-1,1-dioxo-1,4-dihydro-1λ$^6$-benzo[1,2,4]thiadiazin-3-yl)-5-hydroxy-6-isopropyl-2-(3-methyl-butyl)-2H-pyridazin-3-one (5j)

To a solution of 5i (0.100 g, 0.22 mmol) in MeOH (5 mL) and THF (5 mL) was added Raney-Nickel (0.6 mL, 50% slurry in H$_2$O) followed by anhydrous NH$_2$NH$_2$ (0.3 mL, 9.56 mmol). The reaction mixture was stirred 15 min at ambient temperature, filtered using a syringe filter with 0.2 μm PTFE membrane, and concentrated in vacuo. The crude mixture was purified by flash column chromatography using silica gel eluted with 0-3% MeOH/CH$_2$Cl$_2$ to give 5j (0.072 g, 77%) as a red solid. $^1$H NMR (400 MHz, D$_6$-DMSO) δ 7.0 (br s, 1 H), 6.93 (s, 1 H), 6.79 (d, J=2.8 Hz, 1 H), 6.76 (d, J=2.4 Hz), 5.33 (br s, 2 H), 3.86 (t, J=6.8 Hz, 2 H), 3.22 (m, 1 H), 1.52 (m, 3 H), 1.08 (d, J=7.2 Hz, 6 H), 0.90 (d, J=6.4 Hz, 6 H). MS(ESI$^+$) m/e 420 [M+H]$^+$.

N-{3-[5-Hydroxy-6-isopropyl-2-(3-methyl-butyl)-3-oxo-2,3-dihydro-pyridazin-4-yl]-1,1-dioxo-1,4-dihydro-1λ$^6$-benzo[1,2,4]thiadiazin-7-yl}-benzamide (5k)

To a solution of 5j (0.048 g, 0.11 mmol) and 4-dimethylaminopyridine (0.0014 g, 0.011 mmol) in DMF was added triethylamine (18 μL, 0.125 mmol) followed by benzoyl chloride (16 μL, 0.137 mmol). The reaction mixture was stirred 4 h at 80° C. and cooled to room temperature. The reaction mixture was treated with sat NaHCO$_3$ (1 mL) and extracted two times with EtOAc (3 mL). The combined organic layer was washed with brine (1 mL), dried over MgSO$_4$, and concentrated in vacuo. The crude mixture was purified by flash column chromatography using silica gel (0-40% EtOAc/hexanes) to give 5k (0.030 g, 50%) as a yellow solid. $^1$H NMR (400 MHz, D$_6$-DMSO) δ 10.63 (br s), 8.45 (d, J=2.4 Hz, 1H), 8.09 (dd, J=8.8, 2 Hz, 1 H), 8.97 (d, J=7.2 Hz, 2 H), 7.67 (d, J=9.2 Hz, 1 H), 7.60 (d, J=7.2 Hz, 1 H), 7.54 (t, J=7.2 Hz, 2 H), 4.13 (d, J=6.8 Hz, 2 H), 3.25 (m, 1 H), 1.63 (m, 3 H), 1.22 (d, J=6.8 Hz, 6 H), 0.93 (d, J=6.4 Hz, 6 H). LC-MS(ESI$^+$) m/e 524 [M+H]$^+$.

Aniline (5j) can be easily derivatized to form sulfonamide by reacting compound 5j with sulfonyl chloride. It also can be alkylated by reacting with activated alkyl bromide or chloride. In addition, aniline 5j can be reacted with aldehydes via reductive amination to form secondary anilines using the methods known in the art.

The Following Compounds of Formula I were also Made using Method 3.

2-Butyl-5-hydroxy-6-(2-hydroxy-1,1-dimethyl-ethyl)-4-(7-methoxy-1,1-dioxo-1,2-dihydro-1$\lambda^6$-benzo[1,2,4]thiadiazin-3-yl)-2H-pyridazin-3-one $^1$H NMR (400 MHz, CDCl$_3$): δ 7.38-7.41 (m, 1H), 7.18-7.25 (m, 2H), 4.18 (t, 2H, J=6.8 Hz), 3.90 (s, 3H), 3.84 (s, 2H), 1.76-1.85 (m, 2H), 1.41 (s, 6H), 1.33-1.44 (m, 2H), 1.00 (t, 3H, J=7.2 Hz); LC-MS (ESI$^+$): m/e=451.0 [M+1]$^+$ (exact MS: 450.16).

2-{3-[5-Hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-N-methyl-acetamide $^1$H NMR (400 MHz, CDCl$_3$): δ 7.99 (d, 1H, J=4 Hz), 7.43-7.50 (m, 2H), 7.32 (d, 1H, J=9.2 Hz), 7.22-7.28 (m, 1H), 7.14 (t, 1H, J=4.6 Hz), 6.53 (s, br, 1H), 4.58 (s, 2H), 4.30 (t, 2H, J=7.2 Hz), 2.96 (d, 3H, J=4.8 Hz), 1.68-1.80 (m, 3H), 1.03 (d, 6H, J=6 Hz); LC-MS (ESI$^+$): m/e=532.18 [M+1]$^+$ (exact MS: 531.12).

4-{7-[2-(3-Amino-pyrrolidin-1-yl)-2-oxo-ethoxy]-1,1-dioxo-1,2-dihydro-1$\lambda^6$-benzo[1,2,4]thiadiazin-3-yl}-5-hydroxy-2-(3-methyl-butyl)-6-thiophen-2-yl-2H-pyridazin-3-one $^1$H NMR (400 MHz, CD$_3$OD): δ 7.93 (d, 1H, J=3.6 Hz), 7.50 (d, 1H, J=5.2 Hz), 7.42-7.46 (m, 1H), 7.36-7.41 (m, 2H), 7.09 (dd, 1H, J=5.0 Hz, J$_2$=4 Hz), 4.89 (s, 2H, 61%), 4.86 (s, 2H, 39%), 4.26 (t, 2H, J=7.2 Hz), 3.94-4.01 (m, 1H), 3.74-3.86 (m, 2H), 3.64-3.73 (m, 2H), 2.51 (m, 1H, 61%, J=6.2 Hz), 2.38 (m, 1H, 39%, J=6.4 Hz), 2.19-2.27 (m, 1H, 61%), 2.06-2.14 (m, 1H, 39%), 1.64-1.79 (m, 3H), 1.02 (d, 6H, J=6.4 Hz); LC-MS (ESI$^+$): m/e=587.3 [M+1]$^+$ (exact MS: 586.17).

[4-Hydroxy-5-(7-methoxy-1,1-dioxo-1,2-dihydro-1$\lambda^6$-benzo[1,2,4]thiadiazin-3-yl)-1-(3-methyl-butyl)-6-oxo-1,6-dihydro-pyridazin-3-yl]-phenyl-acetonitrile $^1$H NMR (400 MHz, DMSO-d$_6$): δ 12.20 (s, 1H), 10.28 (s, 1H), 7.23-7.36 (m, 8H), 4.04 (t, 2H, J=7.6 Hz), 3.84 (s, 3H), 3.60 (s, 1H), 1.57-1.71 (m, 3H), 0.89 (d, 6H, J=6.4 Hz); LC-MS (ESI$^+$): m/e=508.4 [M+1]+(exact MS: 507.16).

2-{3-[5-Hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-propionic acid ethyl ester $^1$H NMR (400 MHz, CDCl$_3$): δ 7.98 (d, 1H, J=3.6 Hz), 7.45 (d, 1H, J=4.8 Hz), 7.34 (s, br, 1H), 7.24-7.27 (m, 2H), 7.13 (t, 1H, J=4.40 Hz), 4.83 (q, 1H, J=6.7 Hz), 4.21-4.30 (m, 4H), 1.77 (q, 2H, J=7.2 Hz), 1.67 (d, 3H, J=6.8 Hz), 1.64-1.72 (m, 3H), 1.30 (t, 3H, J=7.2 Hz), 1.02 (d, 6H, J=6.4 Hz); LC-MS (ESI$^+$): m/e=561.33 [M+1]$^+$ (exact MS: 560.14)

2-{3-[5-Hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-propionamide $^1$H NMR (400 MHz, DMSO-d$_6$): δ 7.90 (d, 1H, J=3.6 Hz), 7.61-7.69 (m, 3H), 7.28-7.34 (m, 3H), 7.16 (dd, 1H, J=5.0 Hz, J$_2$=3.8 Hz), 4.78 (q, 1H, J=6.4 Hz), 4.17 (t, 2H, J=7.0 Hz), 1.60-1.70 (m, 3H), 1.47 (d, 3H, J=6.4 Hz), 0.95 (d, 6H, J=6.4 Hz); LC-MS (ESI$^+$): m/e=532.14 [M+1]$^+$ (exact MS: 531.12).

2-{3-5-Hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-propionic acid $^1$H NMR (400 MHz, DMSO-d$_6$): δ 7.90 (dd, 1H, J=3.6 Hz, J$_2$=1.2 Hz), 7.67 (dd, 1H, J$_1$=5.2 Hz, J$_2$=1.0 Hz), 7.59 (d, 1H, J=9.2 Hz), 7.31 (dd, 1H, J=9.2 Hz, J$_2$=3.0 Hz), 7.22 (d, 1H, J=2.8 Hz), 7.16 (dd, 1H, J=5.0 Hz, J$_2$=3.8 Hz), 5.05 (q, 1H, J=6.8 Hz), 4.16 (t, 2H, J=7.0 Hz), 1.58-1.70 (m, 3H), 1.53 (d, 3H, J=6.8 Hz), 0.95 (d, 6H, J=6.4 Hz); LC-MS (ESI$^+$): m/e=533.3 [M+1]$^+$ (exact MS: 532.11).

4-(1,1-Dioxo-1,2-dihydro-1$\lambda^6$-benzo[1,2,4]thiadiazin-3-yl)-5-hydroxy-6-isopropyl-2-(3-methyl-butyl)-2H-pyridazin-3-one $^1$H NMR (400 MHz, CDCl$_3$): δ 7.98 (d, 1H, J=8.0 Hz), 7.63 (t, 1H, J=7.2 Hz), 7.47 (t, 1H, J=7.8 Hz), 7.30 (d, 1H, J=8.0 Hz), 4.22 (t, 2H, J=7.4 Hz), 3.33 (m, 1H, J=6.8 Hz), 1.60-1.74 (m, 3H), 1.28 (d, 6H, J=6.4 Hz), 1.01 (d, 6H, J=6.0 Hz); LC-MS (ESI$^+$): m/e=405.4 [M+1]+(exact MS: 404.15).

5-Hydroxy-6-isopropyl-4-(7-methoxy-1,1-dioxo-1,2-dihydro-1$\lambda^6$-benzo[1,2,4]thiadiazin-3-yl)-2-(3-methyl-butyl)-2H-pyridazin-3-one $^1$H NMR (400 MHz, CDCl$_3$): δ 7.43 (d, 1H, J=2.4 Hz), 7.21-7.29 (m, 2H), 4.24 (t, 2H, J=7.2 Hz), 3.93 (s, 3H), 3.35 (m, 1H, J=6.9 Hz), 1.62-1.76 (m, 3H), 1.31 (d, 6H, J=6.8 Hz), 1.03 (d, 6H, J=6.4 Hz); LC-MS (ESI$^+$): m/e=435.3 [M+1]$^+$ (exact MS: 434.16).

5-Hydroxy-4-(7-hydroxy-1,1-dioxo-1,2-dihydro-1$\lambda^6$-benzo[1,2,4]thiadiazin-3-yl)-6-isopropyl-2-(3-methyl-butyl)-2H-pyridazin-3-one $^1$H NMR (400 MHz, CDCl$_3$): δ 7.47 (d, 1H, J=2.4 Hz), 7.16-7.23 (m, 2H), 6.81 (s, br, 1H), 4.22 (t, 2H, J=7.0 Hz), 3.33 (m, 1H, J=6.8 Hz), 1.60-1.74 (m, 3H), 1.29 (d, 6H, J=6.8 Hz), 1.00 (d, 6H, J=6.4 Hz); LC-MS (ESI$^+$): m/e=421.3 [M+1]$^+$ (exact MS: 420.15).

2-{3-[5-Hydroxy-6-isopropyl-2-(3-methyl-butyl)-3-oxo-2,3-dihydro-pyridazin-4-yl]-1,1-dioxo-1,2-dihydro-1$\lambda^6$-benzo[1,2,4]thiadiazin-7-yloxy}-acetamide $^1$H NMR (400 MHz, CDCl$_3$): δ 7.46 (d, 1H, J=2.4 Hz), 7.30 (d, 1H, J=8.8 Hz), 7.23-7.25 (m, 1H), 6.45 (s, br, 1H), 5.70 (s, br, 1H), 4.57 (s, 2H), 4.21 (t, 2H, J=7.2 Hz), 3.32 (m, 1H, J=6.8 Hz), 1.63-1.73 (m, 3H), 1.27 (d, 6H, J=6.8 Hz), 1.00 (d, 6H, J=6.4 Hz); LC-MS (ESI$^+$): m/e=478.1 [M+1]+(exact MS: 477.17).

5-Hydroxy-4-(7-methoxy-1,1-dioxo-1,2-dihydro-1λ⁶-benzo[1,2,4]thiadiazin-3-yl)-2-(3-methyl-butyl)-6-(1-methyl-1H-indol-3-yl)-2H-pyridazin-3-one ¹H NMR (400 MHz, DMSO-d₆): 68.27 (d, 1H, J=7.6 Hz), 8.21 (s, br, 1H), 7.49 (d, 1H, J=9.2 Hz), 7.38 (d, 1H, J=8.4 Hz), 7.19-7.29 (m, 3H), 7.14 (t, 1H, J=7.4 Hz), 4.30 (t, 2H, J=7.0 Hz), 3.85 (s, br, 6H), 1.66-1.80 (m, 3H), 0.97 (d, 6H, J=6.4 Hz); LC-MS (ESI⁺): m/e=522.37 [M+1]⁺ (exact MS: 521.17).

2-Benzyl-4-(1,1-dioxo-1,2-dihydro-1λ⁶-benzo[1,2,4]thiadiazin-3-yl)-5-hydroxy-6-isopropyl-2H-pyridazin-3-one ¹H NMR (400 MHz, CDCl₃): δ 7.96-7.98 (m, 1H), 7.61-7.65 (m, 1H), 7.47 (dt, 1H, J₁=7.6 Hz, J₂=1.2 Hz), 7.28-7.41 (m, 6H), 5.36 (s, 2H), 3.34 (m, 1H, J=6.8 Hz), 1.30 (d, 6H, J=7.2 Hz); LC-MS (ESI⁺): m/e=425.7 [M+1]⁺ (exact MS: 424.12).

2-{3-[5-Hydroxy-2-(3-methyl-butyl)-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-butyramide ¹H NMR (400 MHz, CDCl₃): δ 7.94-7.96 (m, 1H), 7.47 (d, 1H, J=2.8 Hz), 7.42 (dd, 1H, J=5.0 Hz, J₂=1.0 Hz), 7.27 (d, 1H, J=9.2 Hz), 7.20-7.23 (m, 1H), 7.11 (dd, 1H, J=5.0 Hz, J₂=3.8 Hz), 6.25 (s, br, 1H), 5.58 (s, br, 1H), 4.58 (t, 1H, J=5.6 Hz), 4.26 (t, 2H, J=7.6 Hz), 1.98-2.06 (m, 2H), 1.62-1.77 (m, 3H), 1.05 (t, 3H, J=7.2 Hz), 1.00 (d, 6H, J=6.4 Hz); LC-MS (ESI⁺): m/e=546.9 [M+1]⁺ (exact MS: 545.14).

N-Hydroxy-2-{3-[5-hydroxy-2-(3-methyl-butyl)-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-acetamide ¹H NMR (400 MHz, CD₃OD): δ 7.96 (d, 1H, J=2.8 Hz), 7.39 (d, 1H, J=5.2 Hz), 7.28-7.33 (m, 3H), 7.05 (t, 1H, J=4.2 Hz), 4.62 (s, br, 2H), 4.13 (t, 2H, J=6.8 Hz), 1.64-1.73 (m, 3H), 1.00 (d, 6H, J=6.4 Hz); LC-MS (ESI⁺): m/e=533.8 [M+1]+(exact MS: 533.10).

2-[3-(2-Cyclobutylmethyl-5-hydroxy-3-oxo-6-thiophen-2-yl-2,3-dihydro-pyridazin-4-yl)-1,1-dioxo-1,2-dihydro-1λ⁶-benzo[1,2,4]thiadiazin-7-yloxy]-acetamide ¹H NMR (400 MHz, CDCl₃): δ 7.99 (dd, 1H, J=3.6 Hz, J₂=1.2 Hz), 7.49 (d, 1H, J=2.4 Hz), 7.46 (dd, 1H, J₁=5.0 Hz, J₂=1.0 Hz), 7.28-7.33 (m, 2H), 7.15 (dd, 1H, J₁=5.0 Hz, J₂=3.8 Hz), 6.45 (s, br, 1H), 5.65 (s, br, 1H), 4.59 (s, 2H), 4.30 (d, 2H, J=7.2 Hz), 2.92 (m, 1H, J=7.2 Hz), 2.10-2.18 (m, 2H), 1.90-2.02 (m, 4H); LC-MS (ESI⁺): m/e=516.27 [M+1]⁺ (exact MS: 515.09).

2-{3-[2-(2-Cyclopropyl-ethyl)-5-hydroxy-3-oxo-6-thiophen-2-yl-2,3-dihydro-pyridazin-4-yl]-1,1-dioxo-1,2-dihydro-1-benzo[1,2,4]thiadiazin-7-yloxy}-acetamide LC-MS (ESI⁺): m/e=516.0 [M+1]⁺ (exact MS: 515.09); ¹H NMR (400 MHz, DMSO-d₆): δ 7.90 (d, 1H, J=3.6 Hz), 7.67 (d, 1H, J=5.2 Hz), 7.62 (s, br, 1H), 7.58-7.61 (m, 1H), 7.40 (s, br, 1H), 7.32-7.38 (m, 2H), 7.16 (dd, 1H, J₁=4.8 Hz, J₂=3.6 Hz), 4.57 (s, 2H), 4.22 (t, 2H), 1.69 (q, 2H, J=7.2 Hz), 0.70-0.80 (m, 1H), 0.38-0.43 (m, 2H), 0.04 (q, 2H, J=5.2 Hz).

2-Cyclobutylmethyl-4-(1,1-dioxo-1,2-dihydro-1λ⁶-benzo[1,2,4]thiadiazin-3-yl)-5-hydroxy-6-isopropyl-2H-pyridazin-3-one LC-MS (ESI⁺): m/e=403.39 [M+1]⁺ (exact MS: 402.14); ¹H NMR (400 MHz, CDCl₃): δ 7.98 (dd, 1H, J₁=7.2 Hz, J₂=0.8 Hz), 7.62-7.66 (m, 1H), 7.46-7.50 (m, 1H), 7.28 (d, 1H, J=8.4 Hz), 4.22 (d, 2H, J=7.6 Hz), 3.33 (m, 1H, J=6.8 Hz), 2.86 (m, 1H, J=7.6 Hz), 2.05-2.11 (m, 2H), 1.86-2.00 (m, 4H), 1.28 (d, 6H, J=6.8 Hz)

6-Butyl-5-hydroxy-4-(7-methoxy-1,1-dioxo-1,2-dihydro-1λ⁶-benzo[1,2,4]thiadiazin-3-yl)-2-(3-methyl-butyl)-2H-pyridazin-3-one LC-MS (ESI⁺): m/e=449.20 [M+1]⁺ (exact ms: 448.18); ¹H NMR (400 MHz, CDCl₃): δ 7.40 (d, 1H, J=2.8 Hz), 7.23 (d, 1H, J=8.4 Hz), 7.19 (dd, 1H, J=8.4, 2.8 Hz), 4.20 (t, 2H, J=7.2 Hz), 3.90 (s, 3H), 2.74 (t, 2H, J=7.6 Hz), 1.68 (m, 5H), 1.41 (m, 2H), 1.00 (d, 6H, 6.0 Hz), 0.98 (t, 3H, J=7.2 Hz).

6-Butyl-5-hydroxy-4-(7-hydroxy-1,1-dioxo-1,2-dihydro-1λ⁶-benzo[1,2,4]thiadiazin-3-yl)-2-(3-methyl-butyl)-2H-pyridazin-3-one LC-MS (ESI⁺): m/e=435.2 [M+1]⁺ (exact ms: 434.16); ¹H NMR (400 MHz, CDCl₃): δ 7.46 (d, 1H, J=2.8 Hz), 7.21 (d, 1H, J=8.8 Hz), 7.16 (dd, 1H, J=8.8, 2.8 Hz), 6.83 (broad s, 1H), 4.20 (t, 2H, J=6.8 Hz), 2.75 (t, 2H, J=7.2 Hz), 1.69 (m, 5H), 1.42 (m, 2H), 1.00 (d, 6H, 6.0 Hz), 0.98 (t, 3H, J=7.2 Hz).

2-{3-[6-Butyl-5-hydroxy-2-(3-methyl-butyl)-3-oxo-2,3-dihydro-pyridazin-4-yl]-1,1-dioxo-1,2-dihydro-1λ⁶-benzo[1,2,4]thiadiazin-7-yloxy}-acetamide LC-MS (ESI⁺): m/e=492.24 [M+1]⁺ (exact ms: 491.18); ¹H NMR (400 MHz, CDCl₃): δ 7.43 (d, 1H, J=2.4 Hz), 7.29 (d, 1H, J=8.8 Hz), 7.24 (dd, 1H, J=8.8, 2.4 Hz), 4.54 (s, 2H), 4.16 (t, 2H, J=7.6 Hz), 2.71 (t, 2H, J=7.2), 1.64 (m, 5H), 1.38 (m, 2H), 0.96 (d, 6H, 7.2 Hz), 0.94 (t, 3H, J=7.6 Hz).

2-Butyl-5-hydroxy-4-(7-methoxy-1,1-dioxo-1,2-dihydro-1λ⁶-benzo[1,2,4]thiadiazin-3-yl)-6-(3-methyl-butyl)-2H-pyridazin-3-one LC-MS (ESI⁺): m/e=449.23 [M+1]⁺ (exact ms: 448.18); ¹H NMR (400 MHz, CDCl₃): δ 7.40 (d, 1H, J=2.4 Hz), 7.23 (d, 1H, J=8.8 Hz), 7.19 (dd, 1H, J=8.8, 2.4 Hz), 4.18 (t, 2H, J=7.6 Hz), 3.90 (s, 3H), 2.74 (m, 2H), 1.80 (m, 2H), 1.62 (m, 1H), 1.58 (m, 2H), 1.40 (m, 2H), 1.00 (t, 3H, J=7.2 Hz), 0.98 (d, 6H, J=6.4 Hz).

2-Butyl-5-hydroxy-4-(7-hydroxy-1,1-dioxo-1,2-dihydro-1λ⁶-benzo[1,2,4]thiadiazin-3-yl)-6-(3-methyl-butyl)-2H-pyridazin-3-one LC-MS (ESI⁺): m/e=435.24 [M+1]⁺ (exact ms: 434.16); ¹H NMR (400 MHz, CDCl₃): δ 7.46 (d, 1H, J=2.8 Hz), 7.20 (d, 1H, J=8.8 Hz), 7.16 (dd, 1H, J=8.8, 2.8 Hz), 6.80 (broad s, 1H), 4.18 (t, 2H, J=7.6 Hz), 2.76 (m, 2H), 1.80 (m, 2H), 1.64 (m, 1H), 1.58 (m, 2H), 1.40 (m, 2H), 1.00 (t, 3H, J=7.2 Hz), 0.98 (d, 6H, J=6.4 Hz).

2-{3-[2-Butyl-5-hydroxy-6-(3-methyl-butyl)-3-oxo-2,3-dihydro-pyridazin-4-yl]-1,1-dioxo-1,2-dihydro-1λ⁶-benzo[1,2,4]thiadiazin-7-yloxy}-acetamide LC-MS (ESI⁺): m/e=492.25 [M+1]⁺ (exact ms: 491.18); ¹H NMR (400 MHz, CDCl₃): δ 7.47 (d, 1H, J=2.8 Hz), 7.29 (d, 1H, J=9.2 Hz), 7.24 (dd, 1H, J=9.2, 2.8 Hz), 6.46 (broad s, 1H), 5.67 (broad s, 1H), 4.58 (s, 2H), 4.18 (t, 2H, J=7.2 Hz), 2.75 (m, 2H), 1.80 (m, 2H), 1.62 (m, 1H), 1.58 (m, 2H), 1.40 (m, 2H), 1.01 (t, 3H, J=7.2 Hz), 0.98 (d, 6H, J=6.4 Hz).

2,6-Dibutyl-5-hydroxy-4-(7-methoxy-1,1-dioxo-1,2-dihydro-1λ⁶-benzo[1,2,4]thiadiazin-3-yl)-2H-pyridazin-3-one LC-MS (ESI⁺): m/e=435.31 [M+1]⁺ (exact ms: 434.16); ¹H NMR (400 MHz, CDCl₃): δ 7.40 (d, 1H, J=2.4 Hz), 7.22 (d, 1H, J=8.8 Hz), 7.19 (dd, 1H, J=8.8, 2.4 Hz), 4.18 (t, 2H, J=7.6 Hz), 3.90 (s, 3H), 2.74 (t, 2H, J=8.0 Hz), 1.80 (m, 2H), 1.68 (m, 2H), 1.41 (m, 4H), 0.99 (t, 3H, J=7.2 Hz), 0.98 (t, 3H, J=7.2 Hz).

2,6-Dibutyl-5-hydroxy-4-(7-hydroxy-1,1-dioxo-1,2-dihydro-1,1-benzo[1,2,4]thiadiazin-3-yl)-2H-pyridazin-3-one LC-MS (ESI⁺): m/e=421.04 [M+1]⁺ (exact ms: 420.15); ¹H NMR (400 MHz, CDCl₃): δ 7.46 (d, 1H, J=2.4 Hz), 7.20 (d, 1H, J=8.8 Hz), 7.16 (dd, 1H, J=8.8, 2.4 Hz), 6.90 (broad s, 1H), 4.18 (t, 2H, J=7.2 Hz), 2.75 (t, 2H, J=8.0 Hz), 1.80 (m, 2H), 1.68 (m, 2H), 1.41 (m, 4H), 0.99 (t, 3H, J=7.2 Hz), 0.98 (t, 3H, J=7.2 Hz).

2-[3-(2,6-Dibutyl-5-hydroxy-3-oxo-2,3-dihydro-pyridazin-4-yl)-1,1-dioxo-1,2-dihydro-1λ⁶-benzo[1,2,4]thiadiazin-7-yloxy]-acetamide LC-MS (ESI⁺): m/e=478.17 [M+1]⁺ (exact ms: 477.17); ¹H NMR (400 MHz, CDCl₃): δ 7.47 (d, 1H, J=2.4 Hz), 7.29 (d, 1H, J=8.8 Hz), 7.25 (dd, 1H, J=8.8, 2.4 Hz), 6.47 (broad s, 1H), 5.77 (broad s, 1H), 4.58 (s, 2H), 4.18 (t, 2H, J=7.2 Hz), 2.75 (t, 2H, J=7.6 Hz), 1.80 (m, 2H), 1.68 (m, 2H), 1.41 (m, 4H), 0.99 (t, 3H, J=7.2 Hz), 0.98 (t, 3H, J=7.2 Hz).

5-Hydroxy-4-(7-methoxy-1,1-dioxo-1,2-dihydro-1λ⁶-benzo[1,2,4]thiadiazin-3-yl)-2-(3-methyl-butyl)-6-propyl-2H-pyridazin-3-one LC-MS (ESI⁺): m/e=435.31 [M+1]⁺ (exact ms: 434.16); ¹H NMR (400 MHz, CDCl₃): δ 7.40 (d, 1H, J=2.4 Hz), 7.23 (d, 1H, J=8.8 Hz), 7.19 (dd, 1H, J=8.8, 2.4 Hz), 4.20 (t, 2H, J=7.6 Hz), 3.90 (s, 3H), 2.72 (t, 2H, J=7.6 Hz), 1.72 (m, 5H), 1.01 (t, 3H, J=7.2 Hz), 0.99 (d, 6H, J=6.0 Hz).

5-Hydroxy-4-(7-hydroxy-1,1-dioxo-1,2-dihydro-1λ⁶-benzo[1,2,4]thiadiazin-3-yl)-2-(3-methyl-butyl)-6-propyl-2H-pyridazin-3-one LC-MS (ESI⁺): m/e=421.04 [M+1]⁺ (exact ms: 420.15); ¹H NMR (400 MHz, CDCl₃): δ 7.47 (d, 1H, J=2.4 Hz), 7.22 (d, 1H, J=8.8 Hz), 7.17 (dd, 1H, J=8.8, 2.4 Hz), 4.20 (t, 2H, J=7.6 Hz), 2.73 (t, 2H, J=7.6 Hz), 1.72 (m, 5H), 1.02 (t, 3H, J=7.2 Hz), 1.00 (d, 6H, J=6.4 Hz).

2-{3-[5-Hydroxy-2-(3-methyl-butyl)-3-oxo-6-propyl-2,3-dihydro-pyridazin-4-yl]-1,1-dioxo-1,2-dihydro-1λ⁶-benzo[1,2,4]thiadiazin-7-yloxy}-acetamide LC-MS (ESI⁺): m/e=478.19 [M+1]⁺ (exact ms: 477.17); ¹H NMR (400 MHz, DMSO): δ 7.66 (d, 1H, J=8.8 Hz), 7.62 (broad s, 1H), 7.40 (Broad s, 1H), 7.38 (d, 1H, J=3.2 Hz), 7.35 (m, 1H), 4.58 (s, 2H), 4.12 (t, 2H, J=6.8 Hz), 2.64 (t, 2H, J=7.6 Hz), 1.65 (m, 4H), 1.61 (m, 1H), 0.94 (t, 3H, J=7.2 Hz), 0.92 (d, 6H, J=6.4 Hz).

5-Hydroxy-4-(7-methoxy-1,1-dioxo-1,2-dihydro-1λ⁶-benzo[1,2,4]thiadiazin-3-yl)-2,6-bis-(3-methyl-butyl)-2H-pyridazin-3-one LC-MS (ESI⁺): m/e=463.23 [M+1]⁺ (exact ms: 462.19); ¹H NMR (400 MHz, CDCl₃): δ 7.40 (d, 1H, J=2.8 Hz), 7.24 (d, 1H, J=8.4 Hz), 7.19 (dd, 1H, J=8.4, 2.8 Hz), 4.19 (t, 2H, J=7.6 Hz), 3.90 (s, 3H), 2.75 (m, 2H), 1.74-1.55 (m, 6H), 1.00 (d, 6H, J=6.4 Hz), 0.98 (d, 6H, J=6.4 Hz).

5-Hydroxy-4-(7-hydroxy-1,1-dioxo-1,2-dihydro-1λ⁶-benzo[1,2,4]thiadiazin-3-yl)-2,6-bis-(3-methyl-butyl)-2H-pyridazin-3-one LC-MS (ESI⁺): m/e=449.18 [M+1]⁺ (exact ms: 448.18); ¹H NMR (400 MHz, CDCl₃): δ 7.47 (d, 1H, J=2.4 Hz), 7.21 (d, 1H, J=8.8 Hz), 7.17 (dd, 1H, J=8.8, 2.4 Hz), 6.90 (s, 1H), 4.20 (t, 2H, J=7.6 Hz), 2.75 (m, 2H), 1.74-1.54 (m, 6H), 1.00 (d, 6H, J=6.4 Hz), 0.98 (d, 6H, J=6.4 Hz).

2-{3-[5-Hydroxy-2,6-bis-(3-methyl-butyl)-3-oxo-2,3-dihydro-pyridazin-4-yl]-1,1-dioxo-1,2-dihydro-1λ⁶-benzo[1,2,4]thiadiazin-7-yloxy}-acetamide LC-MS (ESI⁺): m/e=506.24 [M+1]⁺ (exact ms: 505.20); ¹H NMR (400 MHz, CDCl₃): δ 7.46 (d, 1H, J=2.4 Hz), 7.30 (d, 1H, J=9.2 Hz), 7.17 (dd, 1H, J=8.8, 2.4 Hz), 6.47 (s, 1H), 5.75 (s, 1H), 4.58 (s, 2H), 4.20 (t, 2H, J=7.6 Hz), 2.75 (m, 2H), 1.74-1.54 (m, 6H), 1.00 (d, 6H, J=6.4 Hz), 0.98 (d, 6H, J=6.4 Hz).

6-Furan-2-yl-5-hydroxy-4-(7-methoxy-1,1-dioxo-1,2-dihydro-1λ⁶-benzo[1,2,4]thiadiazin-3-yl)-2-(3-methyl-butyl)-2H-pyridazin-3-one LC-MS (ESI⁺): m/e=459.3 [M+1]⁺ (exact ms: 458.13); ¹H NMR (400 MHz, CDCl₃): δ 7.62 (dd, 1H, J=2.0, 0.8 Hz), 7.41 (d, 1H, J=2.4 Hz), 7.33 (dd, 1H, J=3.6, 0.8 Hz), 7.27 (d, 1H, J=8.8 Hz), 7.22 (dd, 1H, J=8.8, 3.2 Hz), 6.58 (dd, 1H, J=3.6, 2.0 Hz), 4.33 (t, 2H, J=7.6 Hz), 3.91 (s, 3H), 1.78 (m, 2H), 1.71 (m, 1H), 1.02 (d, 6H, J=6.4 Hz).

2-(3,3-Dimethyl-butyl)-4-(1,1-dioxo-1,2-dihydro-1λ⁶-benzo[1,2,4]thiadiazin-3-yl)-5-hydroxy-6-isopropyl-2H-pyridazin-3-one LC-MS (ESI⁺): m/e=419.20 [M+1]⁺ (exact ms: 418.17); ¹H NMR (400 MHz, CDCl₃): δ 7.97 (m, 1H), 7.63 (m, 1H), 7.48 (m, 1H), 7.31 (d, 1H, J=8.0 Hz), 4.21 (m, 2H), 3.33 (m, 1H), 1.71 (m, 2H), 1.28 (d, 6H, J=6.8 Hz), 1.03 (s, 9H).

2-(2-Cyclopropylethyl)-4-(1,1-dioxo-1,2-dihydro-1λ⁶-benzo[1,2,4]thiadiazin-3-yl)-5-hydroxy-6-isopropyl-2H-pyridazin-3-one LC-MS (ESI⁺): 403.38 [M+H]⁺. ¹H-NMR (400 MHz, CDCl₃, ppm): 7.95 (dd, 1H, J=8.0, 1.4 Hz); 7.63 (t, 1H, J=7.8 Hz); 7.47 (t, 1H, J=7.6 Hz); 7.29 (d, 1H, J=8.2 Hz); 4.29 (t, 2H, J=7.0 Hz); 3.33 (septet, 1H, J=6.8 Hz); 1.73 (q, 2H, J=7.0 Hz); 1.27 (d, 6H, J=6.6 Hz); 0.73 (m, 1H); 0.46 (m, 2H) 0.05 (q, 2H, J=5.3 Hz).

6-tert-Butyl-2-(3,3-dimethyl-butyl)-5-hydroxy-4-(7-methoxy-1,1-dioxo-1,2-dihydro-1$\lambda^6$-benzo[1,2,4]thiadiazin-3-yl)-2H-pyridazin-3-one LC-MS (ESI$^+$): m/e=463.90 [M+1]$^+$ (exact ms: 462.19); $^1$H NMR (400 MHz, CDCl$_3$): δ 7.40 (d, 1H, J=2.87 Hz), 7.25 (m, 1H), 7.19 (dd, 1H, J=8.8, 2.8 Hz), 4.20 (m, 2H), 3.90 (s, 3H), 1.72 (m, 2H), 1.41 (s, 9H), 1.02 (s, 9H).

3-[1-(3,3-Dimethyl-butyl)-4-hydroxy-5-(7-methoxy-1,1-dioxo-1,2-dihydro-1$\lambda^6$-benzo[1,2,4]thiadiazin-3-yl)-6-oxo-1,6-dihydro-pyridazin-3-yl]-propionitrile LC-MS (ESI$^+$): m/e=460.17 [M+1]$^+$ (exact ms: 459.16); $^1$H NMR (400 MHz, DMSO-d$_6$): δ 7.24 (d, 1H, J=8.8 Hz), 7.15 (dd, 1H, J=8.8, 2.8 Hz), 7.12 (d, 1H, J=2.8 Hz), 3.91 (m, 2H), 3.81 (s, 3H), 2.77 (m, 4H), 1.55 (m, 2H), 0.93 (s, 9H).

2-(3,3-Dimethyl-butyl)-5-hydroxy-4-(7-methoxy-1,1-dioxo-1,2-dihydro-1$\lambda^6$-benzo[1,2,4]thiadiazin-3-yl)-6-thiophen-2-yl-2H-2yl-2H-pyridazin-3-one LC-MS (ESI$^+$): m/e=489.10 [M+1]$^+$ (exact ms: 488.12); $^1$H NMR (400 MHz, CDCl$_3$): δ 7.99 (dd, 1H, J=4.0, 0.8 Hz), 7.45 (dd, 1H, J=5.2, 0.8 Hz), 7.41 (d, 1H, J=2.4 Hz), 7.28 (1H, d, J=9.2 Hz), 7.21 (dd, 1H, J=9.2, 2.8 Hz), 7.14 (dd, 1H, J=5.6, 4.0 Hz), 4.29 (m, 2H), 3.91 (s, 3H), 1.77 (m, 2H), 1.05 (s, 9H).

2-{3-[2-(3,3-Dimethyl-butyl)-5-hydroxy-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-acetamide LC-MS (ESI$^+$): m/e=532.16 [M+1]$^+$ (exact ms: 531.12); $^1$H NMR (400 MHz, DMSO-d$_6$): δ 7.90 (d, 1H, J=3.2 Hz), 7.64 (d, 1H, J=4.8 Hz), 7.61 (broad s, 1H), 7.57 (d, 1H, J=9.2 Hz), 7.40 (broad s, 1H), 7.33 (m, 2H), 7.15 (dd, 1H, J=4.8, 3.6 Hz), 4.56 (s, 2H), 4.14 (m, 2H), 1.67 (m, 2H), 0.97 (s, 9H).

2-{3-[2-(3,3-Dimethyl-butyl)-5-hydroxy-6-(5-methyl-thiophen-2-yl)-3-oxo-2,3-dihydro-pyridazin-4-yl]-1,1-dioxo-1,2-dihydro-λ$^6$-benzo[1,2,4]thiadiazin-7-yloxy}-acetamide LC-MS (ESI$^+$): m/e=546.25 [M+1]$^+$ (exact ms: 545.14); $^1$H NMR (400 MHz, DMSO-d$_6$): δ 7.70 (d, 1H, J=2.8 Hz), 7.61 (s, 1H), 7.54 (d, 1H, J=9.2 Hz), 7.32 (dd, 1H, J=8.8, 2.4 Hz), 7.30 (s, 1H), 6.82 (d, 1H, J=2.4 Hz), 4.55 (s, 2H), 4.10 (m, 2H), 2.47 (s, 3H), 1.65 (m, 2H), 0.97 (s, 9H).

2-Benzyl-4-(1,1-dioxo-1,2-dihydro-1$\lambda^6$-benzo[1,2,4]thiadiazin-3-yl)-5-hydroxy-6-(5-methyl-thiophen-2-yl)-2H-pyridazin-3-one $^1$H NMR (400 MHz, CDCl$_3$): 14.06 (s, 1H), 7.99 (d, 1H, J=7.6 Hz), 7.81 (d, 1H, J=4 Hz), 7.64 (t, 1H, J=7.8 Hz), 7.50 (m, 3H), 7.38 (m, 4H), 6.80 (d, 1H, J=3.6 Hz), 5.41 (s, 2H), 2.57 (s, 3H); LC-MS (ESI$^+$): m/e=479.1 [M+1]$^+$.

2-{3-[2-(2-Cyclopropyl-ethyl)-5-hydroxy-6-(5-methyl-thiophen-2-yl)-3-oxo-2,3-dihydro-pyridazin-4-yl]-1,1-dioxo-1,2-dihydro-1$\lambda^6$-benzo[1,2,4]thiadiazin-7-yloxy}-acetamide LC-MS (ESI$^+$): m/e 530.9 [M+1]$^+$; $^1$H NMR (DMSO-d$_6$): 7.72 (d, 1H, J=3.2 Hz), 7.62 (s, br, 1H), 7.61 (d, 1H, J=9.2 Hz), 7.40 (s, br, 1H), 7.33-7.37 (m, 2H), 6.84 (dd, 1H, J=3.6 Hz, J$_2$=0.8 Hz), 4.57 (s, 2H), 4.20 (t, 2H, J=7.0 Hz), 2.47 (s, 3H), 1.67 (q, 2H, J=6.9 Hz), 0.68-0.79 (m, 1H), 0.38-0.43 (m, 2H), 0.03 (q, 2H, J=4.8 Hz).

2-{3-[2-Cyclobutylmethyl-5-hydroxy-6-(5-methyl-thiophen-2-yl)-3-oxo-2,3-dihydro-pyridazin-4-yl]-1,1-dioxo-1,2-dihydro-1$\lambda^6$-benzo[1,2,4]thiadiazin-7-yloxy}-acetamide LC-MS (ESI$^+$): m/e 530.8 [M+1]$^+$; $^1$H NMR (DMSO-d$_6$, ppm): 7.71 (d, 1H, J=3.6 Hz), 7.62 (s, br, 1H), 7.60 (d, 1H, J=8.8 Hz), 7.40 (s, br, 1H), 7.32-7.38 (m, 2H), 6.83-6.85 (m, 1H), 4.57 (s, 2H), 4.15 (d, 2H, J=7.6 Hz), 2.71-2.84 (m, 1H), 2.47 (s, 3H), 1.98-2.06 (m, 2H), 1.81-1.92 (m, 4H).

6-tert-Butyl-2-(3,3-dimethyl-butyl)-5-hydroxy-4-(7-hydroxy-1,1-dioxo-1,2-dihydro-1$\lambda^6$-benzo[1,2,4]thiadiazin-3-yl)-2H-pyridazin-3-one LC-MS (ESI$^+$): m/e=449.20 [M+1]$^+$ (exact ms: 448.18); $^1$H NMR (400 MHz, CDCl$_3$): δ 7.46 (d, 1H, J=2.8 Hz), 7.24 (d, 1H, J=8.8 Hz), 7.17 (dd, 1H, J=8.8, 2.8 Hz), 6.44 (br, s, 1H), 4.21 (m, 2H), 3.90 (s, 3H), 1.72 (m, 2H), 1.42 (s, 9H), 1.02 (s, 9H).

2-{3-[6-tert-Butyl-2-(3,3-dimethyl-butyl)-5-hydroxy-3-oxo-2,3-dihydro-pyridazin-4-yl]-1,1-dioxo-1,2-dihydro-1$\lambda^6$-benzo[1,2,4]thiadiazin-7-yloxy}-acetamide LC-MS (ESI$^+$): m/e=506.9 [M+1]$^+$ (exact ms: 505.20); $^1$H NMR (400 MHz, DMSO-d$_6$): δ 7.67 (d, 1H, J=8.8 Hz), 7.62 (br, s, 1H), 7.40 (br, s, 1H), 7.37 (dd, 1H, J=8.8, 2.8 Hz), 7.35 (m, 1H), 4.58 (s, 2H), 4.13 (m, 2H), 1.65 (m, 2H), 1.37 (s, 9H), 0.95 (s, 9H).

Method 4: Scheme 4 provides a general procedure that was used to prepare compounds of Formula I.

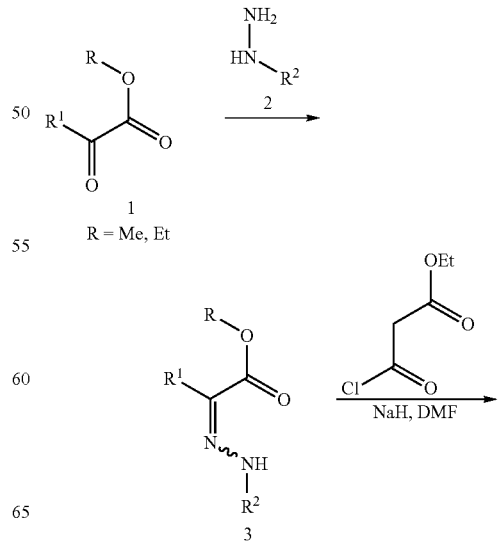

Scheme 4

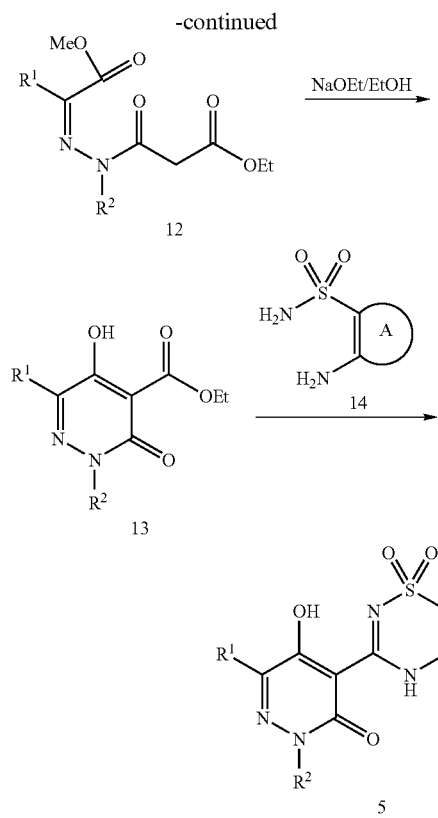

In the general procedure, the α-ketoesters were reacted with hydrazines to form hydrazones that were then treated with ethyl malonyl chloride followed by base treatment to generate the cyclized pyridazinone (13) intermediate. This intermediate was then mixed with the o-amino sulfonamide (14) without or with solvent in a heated condition to give the desired compounds (5) of Formula I.

EXAMPLE 4-1

Scheme 4a describes the synthesis of 4-(1,1-Dioxo-1,2-dihydro-1λ$^6$-pyrido[4,3-e][1,2,4]thiadiazin-3-yl)-5-hydroxy-2-(3-methyl-butyl)-6-thiophen-2-yl-2H-pyridazin-3-one (5l)

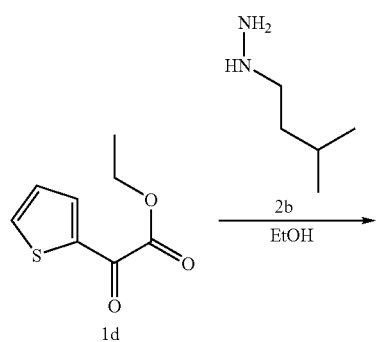

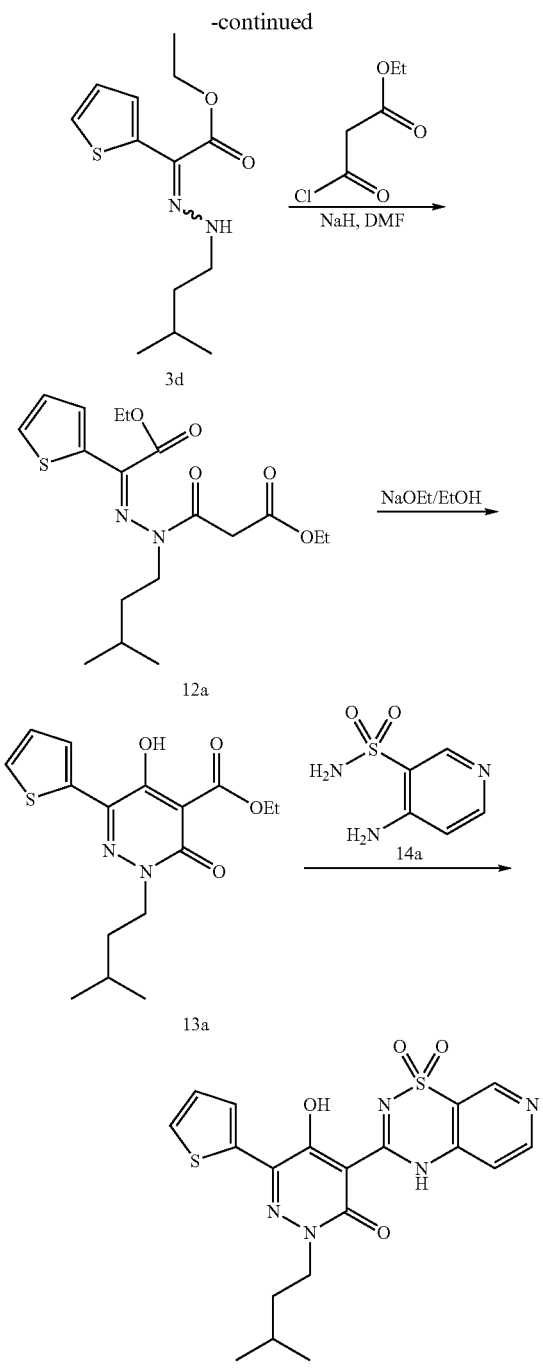

[(3-Methyl-butyl)-hydrazono]-thiophen-2-yl-acetic acid ethyl ester (3d)

To a solution of oxo-thiophen-2-yl-acetic acid ethyl ester (1d) (3.97 g, 21.6 mmol) in absolute ethanol (100 mL), (3-Methyl-butyl)-hydrazine (2b) (2.0 g, 19.6 mmol) was added. The mixture was stirred at 80° C. under N$_2$ atmosphere for 2-25 hours. The reaction mixture was concentrated under reduced pressure and the residue was purified by flash chromatography on silica gel to give the desired product (3d) (2.48 g) that was directly used in the next step. LC-MS (ESI+): m/e 269.2 [M+1]+, 537.4 [2M+1]+, 559.0 [2M+Na]+ (exact ms: 268.12).

[(2-Ethoxycarbonyl-acetyl)-(3-methyl-butyl)-hydrazono]-thiophen-2-yl-acetic acid ethyl ester (12a)

To a solution of [(3-Methyl-butyl)-hydrazono]-thiophen-2-yl-acetic acid ethyl ester (3d) (400 mg, 1.49 mmol) in anhydrous DMF (8 mL) at 0° C. under $N_2$ atmosphere, NaH (Aldrich) (60% in mineral oil, 78 mg, 1.94 mmol) was added, and the resulting suspension was stirred for 20 min. Ethyl malonyl chloride (Alfa Aesar) (317 μL, 2.24 mmol) was added. The reaction mixture was stirred at 0° C. for 1 hour, and quenched by addition of $H_2O$, extracted with EtOAc (50 mL×2). The combined organic layer was washed with brine, dried over $MgSO_4$, concentrated under reduced pressure and the residue was purified by flash chromatography on silica gel to give the desired product (12a) (380 mg, 67%) as a mixture of E/Z isomers. LC-MS (ESI+): m/e 383.4 [M+1]+ (exact ms: 382.16); $^1$H NMR (400 MHz, CDCl$_3$): δ 7.40 (dd, 1H, J=4.8, 0.8 Hz), 7.16 (m, 1H), 7.04 (dd, 1H, J=5.6, 4.0 Hz), 4.45 (q, 2H, J=7.2 Hz), 4.20 (m, 2H), 3.86 (m, 2H), 3.71 (s, 2H), 1.57 (m, 1H), 1.50 (m, 2H), 1.43 (t, 3H, J=7.2 Hz), 1.26 (t, 3H, J=7.2 Hz), 0.92 (d, 6H, J=6.4 Hz).

5-Hydroxy-2-(3-methyl-butyl)-3-oxo-6-thiophen-2-yl-2,3-dihydro-pyridazine-4-carboxylic acid ethyl ester (13a)

To a solution of [(2-Ethoxycarbonyl-acetyl)-(3-methyl-butyl)-hydrazono]-thiophen-2-yl-acetic acid ethyl ester (12a) (380 mg, 1.0 mmol) in EtOH (6 mL) at room temperature, sodium ethoxide (Aldrich) (21 wt % in ethanol, 0.4 mL, 1.1 mmol) was added, and the resulting mixture was stirred for 30 min. Aqueous HCl (5%, 0.75 mL) was added slowly, and then followed by liquid-liquid extraction with $H_2O$/EtOAc. The combined organic layer was washed with brine, dried over $MgSO_4$, concentrated under reduced pressure and the residue was purified by flash chromatography on silica gel to give the desired product (13a) (280 mg, 83%) as yellow solid. LC-MS (ESI+): m/e=337.30 [M+1]+(exact ms: 336.11); $^1$H NMR (400 MHz, CDCl$_3$): δ 7.89 (dd, 1H, J=3.6, 1.2 Hz), 7.39 (dd, 1H, J=5.2, 1.2 Hz), 7.10 (dd, 1H, J=5.2, 3.6 Hz), 4.53 (q, 2H, J=7.2 Hz), 4.22 (m, 2H), 1.73 (m, 2H), 1.68 (m, 1H), 1.50 (t, 3H, J=7.2 Hz), 0.99 (d, 6H, J=6.4 Hz).

4-(1,1-Dioxo-1,2-dihydro-1λ$^6$-pyrido[4,3-e][1,2,4]thiadiazin-3-yl)-5-hydroxy-2-(3-methyl-butyl)-6-thiophen-2-yl-2H-pyridazin-3-one (5l)

5-Hydroxy-2-(3-methyl-butyl)-3-oxo-6-thiophen-2-yl-2,3-dihydro-pyridazine-4-carboxylic acid ethyl ester (13a) (153 mg, 0.46 mmol) and 4-Amino-3-pyridine sulfonamide (14a) (80 mg, 0.46 mmol) were dissolved in N-Methylpyrrolidinone (NMP) (2 mL) under $N_2$ atmosphere, and then stirred at 180° C. for 30 min. The reaction mixture was cooled to room temperature, liquid-liquid extraction was then performed using EtOAc and $H_2O$. The combined organic layer was washed with brine, dried over $MgSO_4$, concentrated under reduced pressure and the residue was purified by flash chromatography on silica gel followed by HPLC purification to give the title compound (5l) (5 mg, 5%) as yellow solid. LC-MS (ESI+): m/e=446.08 [M+1]+ (exact ms: 445.09); $^1$H NMR (400 MHz, DMSO-d$_6$): δ 9.00 (s, 1H), 8.64 (d, 1H, J=6.0 Hz), 7.89 (dd, 1H, J=3.6, 1.2 Hz), 7.56 (dd, 1H, J=5.2, 1.2 Hz), 7.49 (d, 1H, J=6.0 Hz), 7.10 (dd, 1H, J=5.2, 3.6 Hz), 4.06 (t, 2H, J=6.8 Hz), 1.62(m, 3H), 0.93 (d, 6H, J=6.4 Hz).

Compounds of formula 1 that contain other 6-membered aromatic heterocycles to replace the pyridine ring of the above compound (5l) may be prepared in similar way using this method.

The following compounds of Formula I were made in a manner analogous to the procedure described in Method 4, except with the appropriate starting materials.

5-Hydroxy-4-(7-methoxy-1,1-dioxo-1,2-dihydro-1λ$^6$-benzo[1,2,4]thiadiazin-3-yl)-2-(3-methyl-butyl)-6-(3-methyl-thiophen-2-yl)-2H-pyridazin-3-one $^1$H NMR: (DMSO-d$_6$, 400 MHz) δ 7.39 (d, 1H, J=5.1 Hz), 7.24 (d, 1H, J=9.0 Hz), 7.15 (dd, 1H, J=9.0, 2.7 Hz), 7.11 (d, 1H, J=2.7 Hz), 6.89 (d, 1H, J=5.1 Hz), 4.02-3.97 (m, 2H), 3.81 (s, 3H), 2.40 (s, 3H), 1.62-1.59 (m, 4H), 0.93 (d, 6H, J=6.2 Hz); LC-MS (ESI+): m/e 489.13 [M+H]+.

2-{3-[5-Hydroxy-2-(3-methyl-butyl)-6-(3-methyl-thiophen-2-yl)-3-oxo-2,3-dihydro-pyridazin-4-yl]-1,1-dioxo-1,2-dihydro-1λ$^6$-benzo[1,2,4]thiadiazin-7-yloxy}-acetamide $^1$H NMR: (DMSO-d$_6$, 400 MHz) δ 7.60 (s, 1H), 7.49 (d, 1H, J=5.1 Hz), 7.42 (d, 1H, J=9.0 Hz), 7.38 (s, 1H), 7.28-7.22 (m, 2H), 6.95 (d, 1H, J=5.1 Hz), 4.52 (s, 2H), 4.07-4.06 (m, 2H), 2.37 (s, 3H), 1.65-1.60 (m, 4H), 0.84 (d, 6H, J=6.6 Hz); LC-MS (ESI+): m/e 532.15 [M+H]+.

5-Hydroxy-4-(7-methoxy-1,1-dioxo-1,2-dihydro-1λ$^6$-benzo[1,2,4]thiadiazin-3-yl)-2-(3-methyl-butyl)-6-thiazol-2-yl-2H-pyridazin-3-one LC-MS (ESI+): m/e=476 [M+H]+(exact MS: 475.10); $^1$H NMR (400 MHz, CDCl$_3$) δ 8.06-8.10 (m, 1H), 7.57-7.61 (m, 1H), 7.40-7.43 (m, 1H), 7.21-7.29 (m, 2H), 4.40 (t, 2H, J=7.6 Hz), 3.92 (s, 3H), 1.70-1.84 (m, 3H), 1.03 (d, 6H, J=6.8 Hz).

Method 5: Scheme 5 Describes the Synthesis of Compounds of Formula I.

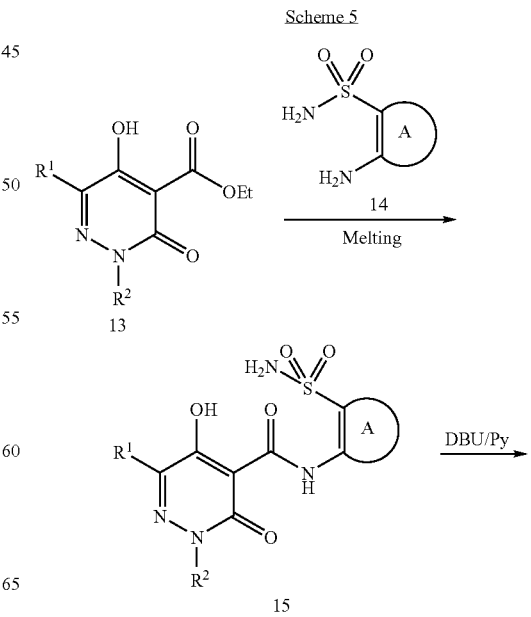

-continued

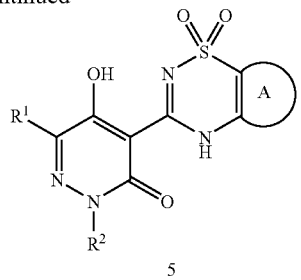
5

In the general procedure, the compound 13 was mixed with compound 14 and heated at a temperature between 160° C. and 170° C. without solvent to give the amide 15. The compound 15 was then treated with 1,8-diazabicyclo[5,4,0]undec-7-ene (DBU) in the presence of pyridine under heating condition in a sealed tube at a temperature between 140° C. to 160° C. to give the desired product (5).

EXAMPLE 5-1

Scheme 5a Describes the Synthesis of Compound 5m

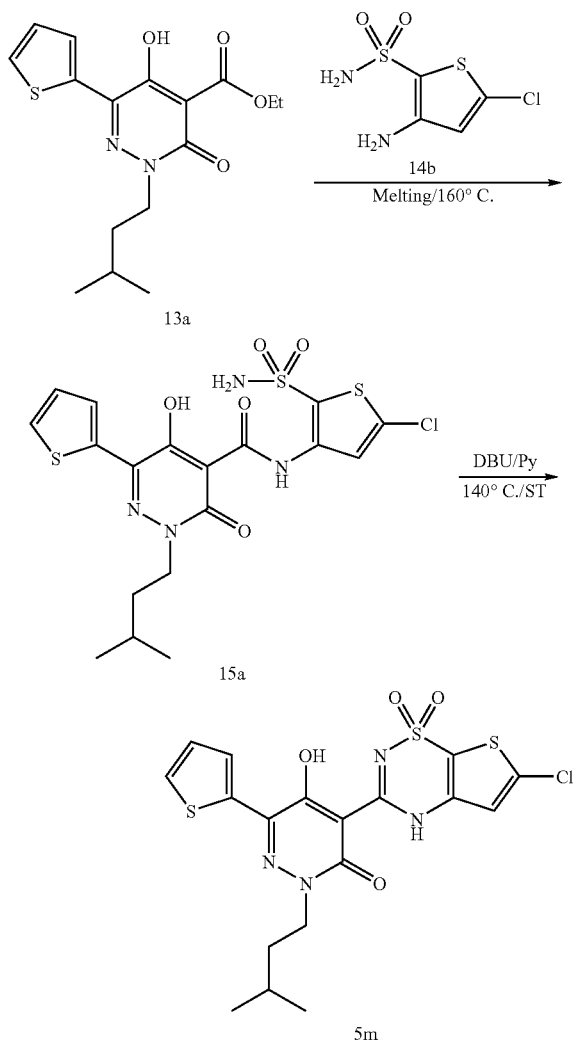

5-Hydroxy-2-(3-methyl-butyl)-3-oxo-6-thiophen-2-yl-2,3-dihydro-pyridazine-4-carboxylic acid (5-chloro-2-sulfamoyl-thiophen-3-yl)-amide (15a)

The ester (13a) made by Method 4 (86 mg, 0.26 mmol) and 3-Amino-5-chloro-thiophene-2-sulfonic acid amide (14b) (54 mg, 0.26 mmol) were mixed in a reaction vial and stirred in a preheated oil-bath at 160° C. for 10 mins to give the corresponding 5-hydroxy-2-(3-methyl-butyl)-3-oxo-6-thiophen-2-yl-2,3-dihydro-pyridazine-4-carboxylic acid (5-chloro-2-sulfamoyl-thiophen-3-yl)-amide (15a) as a dark yellow solid which was used directly in next step without further purification. LC-MS (ESI$^+$): m/e=503.09 [M+1]+(exact ms: 502.02).

4-(2-Chloro-7,7-dioxo-4,7-dihydro-1,7$\lambda^6$-dithia-4,6-diaza-inden-5-yl)-5-hydroxy-2-(3-methyl-butyl)-6-thiophen-2-yl-2H-pyridazin-3-one (5m)

To a solution of the amide intermediate (15a) (54 mg, 0.11 mmol) in anhydrous pyridine (1.5 mL) in a sealed tube, 1,8-Diazabicyclo[5,4,0] undec-7-ene (DBU) (20 μL) was added and then stirred at 140° C. (oil bath temperature) for 24 hrs. The reaction mixture was cooled to room temperature and solvent was removed in vacuo, and then the residue was further dried in high vacuum for 2 hrs. The crude material was purified by flash chromatography on silica gel using hexane and EtOAc to give the desired product (5m) (8.0 mg, 15%) as a yellow solid. LC-MS (ESI$^+$): m/e=485.21 [M+1]$^+$ (exact ms: 484.01); $^1$H NMR (400 MHz, DMSO-d$_6$): δ 7.86 (dd, 1H, J=3.2, 1.2 Hz), 7.52 (dd, 1H, J=5.2, 0.8 Hz), 7.46 (s, 1H), 7.07 (dd, 1H, J=5.2, 3.2 Hz), 4.03 (m, 2H), 1.60 (m, 3H), 0.93 (d, 6H, J=6.4 Hz).

Compounds of formula I that contain the 5-membered aromatic heterocycles as A-ring in place of the thiophene of previous examples as shown above in example 5-1 may be synthesized in a way similar to method 5.

Schemes 6-11 Describe the Synthetic Routes for the Indicated Intermediates.

Scheme 6 Describes the Synthesis of the Intermediate 2.

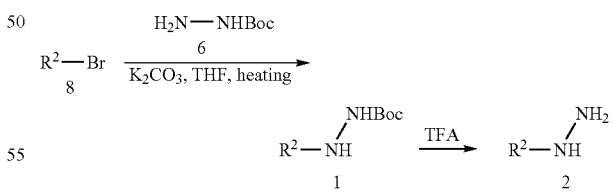

In a typical synthetic route as shown in Scheme 6, bromide 8 can react with tert-butyl carbazate 6 in the presence of K$_2$CO$_3$ upon heating to form Boc-protected hydrazine 1 using the literature procedures described in Huck et al., *Synlett,* 2001 (9), 1467-1469 (2001) and *Tetrahedron Letters,* 40(18), 3543-3546 (1999). The Boc-group can be removed either by treating with TFA or HCl to give the hydrazine 2 as TFA or HCl salt.

EXAMPLE 6-1

Scheme 6a Describes the Synthesis of Cyclobutylmethyl-Hydrazine Trifluoroacetic Acid Salt

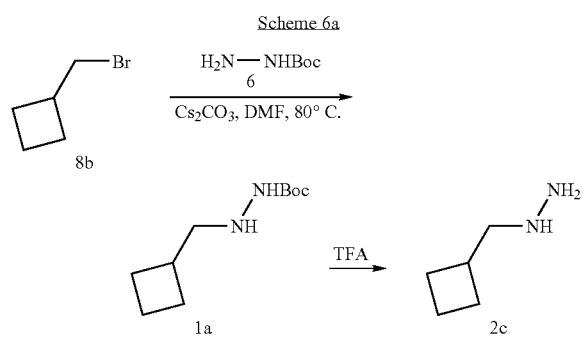

In this specific example, the bromide 8b (2.39 g, 18.1 mmol) was reacted with tert-butyl carbazate 6 (3.24 g, 21.74 mmol) in the presence of Cs$_2$CO$_3$ (12 g, 36.24 mmol) in 40 mL of DMF at 80° C. overnight. MS spectrum confirmed the formation of the desired product (1a) with very little starting material left. After cooling down the reaction mixture, the solid was filtered off. The filtrate was concentrated under vacuum and the crude residue was further purified by flash chromatography on silica gel using a gradient of ethyl acetate in hexane (0-50%). The pure desired product (1a) (669.1 mg) was obtained in 22.5% isolated yield. LC-MS: (ESI$^+$): m/e=201 [M+1]$^+$, 223.2 [M+Na]$^+$, 400.7 [2M+1]$^+$, 423.5 [2M+Na]$^+$ (exact MS: 200.15).

Compound 1a (306 mg) was treated with 10 mL of 20% of TFA in methylene chloride and the reaction mixture was stirred at room temperature for 4.5 hours. LC-MS result confirmed the desired product. The reaction mixture was concentrated under reduced pressure and dried over high vacuum overnight to give yellow oil as the desired product 2c as TFA salt that was directly used in the next step. LC-MS: (ESI$^+$): m/e=201.4 [2M+1]+(exact MS: 100.15).

Scheme 7 Describes the Synthesis of the Intermediate 2.

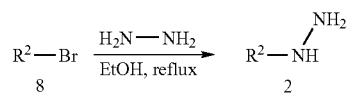

Bromide 8 can be treated with large excess of hydrazine monohydrate in ethanol under reflux condition to give the desired hydrazine 2.

EXAMPLE 7-1

Scheme 7a describes the synthesis of 3-methyl-butyl-hydrazine (2)

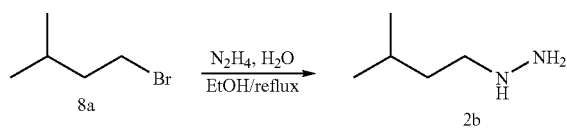

(3-Methyl-butyl)-hydrazine (2b)

To a solution of hydrazine monohydrate (Aldrich) (40 mL) in EtOH (250 mL) under N$_2$ atmosphere, 1-Bromo-3-methyl-butane (8a) (Aldrich) (15.1 g, 100 mmol) was added rapidly, and the resulting mixture was refluxed for 24 hrs. The mixture was cooled down to room temperature and concentrated under reduced pressure. The residue was taken in H$_2$O (40 mL)/DCM (200 mL), solid K$_2$CO$_3$ was added to saturate aqueous layer. Two layers were separated and aqueous layer was extracted with DCM (2×100 mL). The combined organic layers were dried over K$_2$CO$_3$, and then concentrated under reduced pressure to give the desired product (2b) (7.0 g, 70%) as colorless oil. $^1$H NMR (400 MHz, CDCl$_3$): δ 2.80 (m, 2H), 1.65 (m, 1H), 1.41 (m, 2H), 0.93 (d, 6H, J=6.4 Hz).

EXAMPLE 7-2

Synthesis of cyclobutylmethyl-hydrazine (2c)

Cyclobutylmethyl-hydrazine (2c)

Using a similar synthetic route starting with cyclobutylmethyl bromide, cyclobutylmethyl-hydrazine (2c) was also prepared. LC-MS: (ESI$^+$): m/e=201.4 [2M+1]$^+$ (exact MS: 100.10); $^1$H NMR (400 MHz, CDCl$_3$): δ 3.06 (s, br, 3H), 2.81 (d, 2H, J=7.6 Hz), 2.47-2.54 (m, 1H), 2.05-2.13 (m, 2H), 1.83-1.97 (m, 2H), 1.66-1.75 (m, 2H).

Scheme 8 Describes the Synthesis of the Hydrazine Oxalate Salt 6.

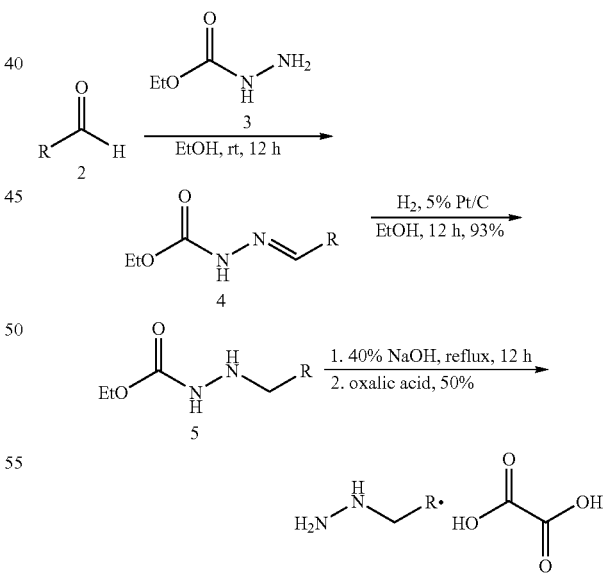

In a general procedure, aldehyde 2 can undergo the reductive amination with compound 3 to give compound 4 which can be reduced to the compound 5. Compound 5 can be treated with NaOH followed by the acidification using oxalic acid to give the desired hydrazine oxalate salt (6).

EXAMPLE 8-1

Scheme 8a describes the synthesis of 2-cyclopropylethyl-hydrazine oxalate salt (6a)

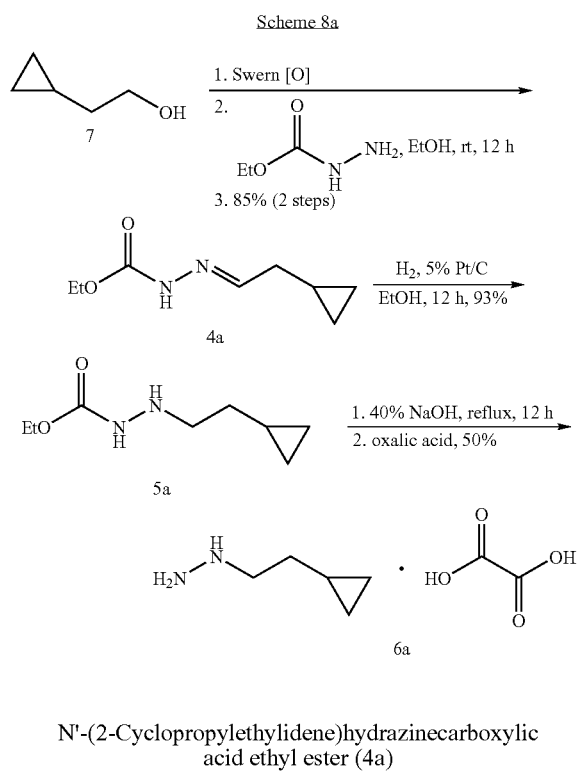

N'-(2-Cyclopropylethylidene)hydrazinecarboxylic acid ethyl ester (4a)

Oxalyl chloride (4.7 mL, 54.3 mmol) was dissolved in 120 mL of $CH_2Cl_2$ and the resulting solution cooled to −78° C. Dimethylsulfoxide (7.7 mL, 0.109 mol) was added dropwise and the reaction mixture was stirred for 10 min at −78° C. 2-Cyclopropylethanol (2) (4.25 g, 49.3 mmol) was dissolved in 10 mL of $CH_2Cl_2$ and added all at once to the reaction. After stirring for 1 h, triethylamine (34.7 mL, 0.25 mol) was added and the reaction was warmed to room temperature. The heterogeneous mixture was then partitioned between $CH_2Cl_2$ and water and extracted twice with $CH_2Cl_2$. The organic layers were combined, washed with brine, dried over $MgSO_4$, and filtered. The resulting solution of 2-cyclopropylethanal was concentrated in vacuo to a volume of approximately 50 mL using a rotary evaporator bath filled with crushed ice. Due to the volatility of this aldehyde, it was used as a crude mixture and not purified further.

The solution of 2-cyclopropylethanal was diluted with 50 mL EtOH. Ethyl carbazate (5.14 g, 49.3 mmol) was added and the solution stirred at room temperature for 12 h, upon which it was concentrated in vacuo and the crude material was purified by flash column chromatography (0-5% MeOH in $CH_2Cl_2$) to give 7.1 g (85%) of the hydrazone (4a) as a colorless crystalline solid. $^1$H-NMR (400 MHz, $CDCl_3$): 8.21 (br s, 1H); 7.21 (s, 1H); 4.23 (m, 2H); 2.17 (t, 3H, J=5.9 Hz) 1.06 (m, 2H); 0.80 (m, 1H); 0.1 (d, 2H); 0.48 (m, 2H); 0.13 (m, 2H) ppm.

N'-(2-Cyclopropylethyl)hydrazinecarboxylic acid ethyl ester (5a)

N'-(2-cyclopropylethylidene)hydrazinecarboxylic acid ethyl ester (4a) (1.5 g, 8.9 mmol) was dissolved in 35 mL EtOH and to this solution was added 5% Pt/C (0.2 g, 0.9 mol). The atmosphere in the flask was evacuated and replaced three times with $H_2$. The reaction was stirred at room temperature for 12 h under a slightly positive pressure of $H_2$, upon which it was filtered through neutral alumina and concentrated to afford 1.4 g (93%) of the desired product (La) as a clear colorless liquid. $^1$H-NMR (400 MHz, $CDCl_3$): 4.18 (q, 2H, J=7.0 Hz); 3.00 (t, 2H, J=7.0 Hz) 1.42 (q, 2H, J=7.0 Hz); 1.29 (t, 3H, J=7.2 Hz); 0.73 (m, 1H); 0.1 (d, 2H); 0.47 (m, 2H); 0.08 (m, 2H) ppm.

2-Cyclopropylethyl-hydrazine oxalate salt (6a)

N'-(2-Cyclopropylethyl)hydrazinecarboxylic acid ethyl ester (5a) (2.2 g, 12.6 mmol) was suspended in 7 mL of a 40% aqueous NaOH solution. The biphasic mixture was heated for 12 h at 120° C., upon which it was cooled to room temperature and partitioned between brine and $CH_2Cl_2$. The organic layer was removed, dried over $MgSO_4$, and filtered. Oxalic acid (1.1 g, 12.6 mmol) was added to the filtrate, which after 12 h was filtered and dried in vacuo to yield 1.7 g (50%) of the oxalate salt (6a) as a white powder. $^1$H-NMR (400 MHz, $D_2O$): 3.13 (t, 2H, J=7.2 Hz); 1.46 (q, 2H, J=7.2 Hz); 0.61 (m, 1H); 0.1 (d, 2H); 0.39 (m, 2H); 0.01 (m, 2H) ppm.

EXAMPLE 8-2

Synthesis of 3-methylbutyl hydrazine oxalate salt (6b)

Using a similar synthetic route starting with isovaleraldehyde and ethyl carbazate, the oxalate salt of 3-methylbutyl hydrazine (6b) was also prepared. $^1$H-NMR (400 MHz, $D_2O$): 3.09 (t, 2H, J=8.0 Hz); 1.58 (m, 1H); 1.47 (m, 2H); 0.84 (d, 6H, J=6.3 Hz) ppm.

EXAMPLE 8-3

Synthesis of (3,3-dimethyl-butyl)-hydrazine oxalate salt (6c)

Using the same synthetic route, (3,3-dimethyl-butyl)-hydrazine oxalate salt (6c) was also prepared. $^1$H NMR (400 MHz, $D_2O$): δ 3.08 (m, 2H), 1.47 (m, 2H), 0.85 (s, 9H) ppm.

Scheme 9 describes the synthesis of intermediates of 9, 4a, 10a, 10b and 4b.

Scheme 9

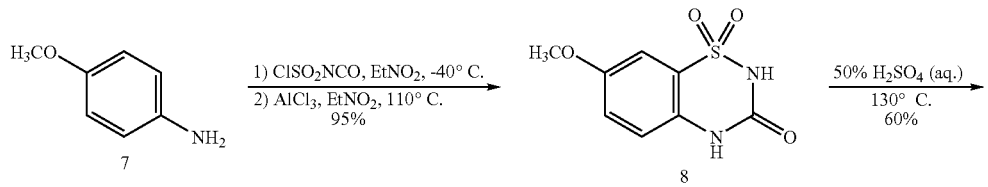

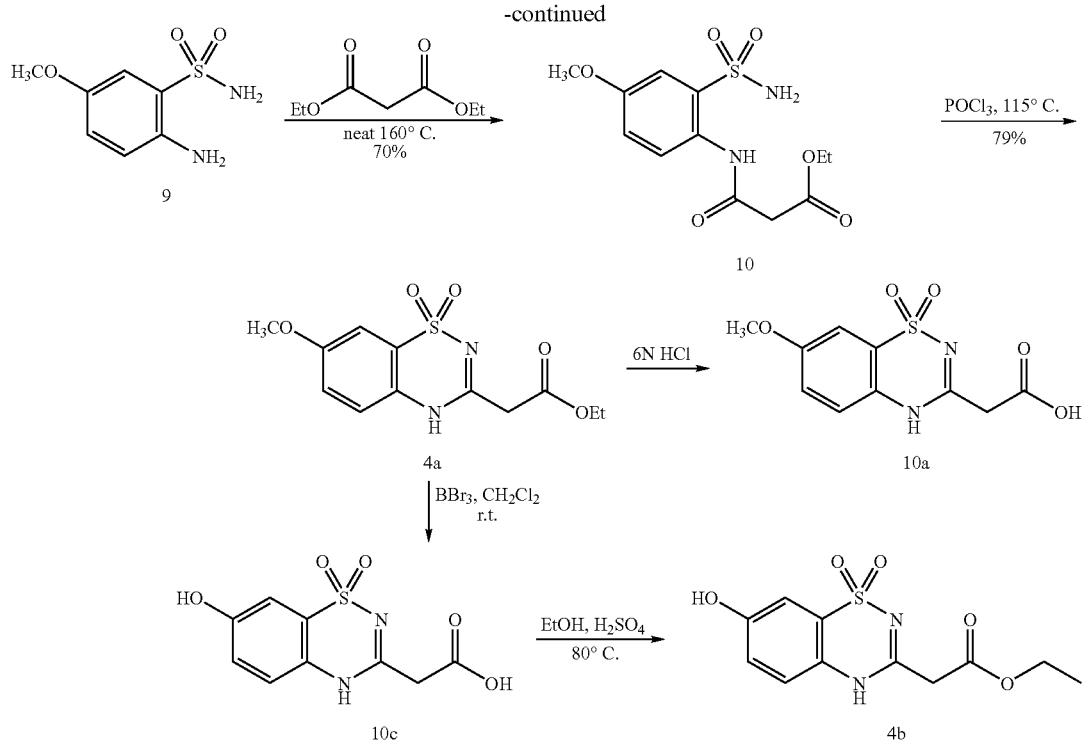

7-Methoxy-1,1-dioxo-1,4-dihydro-2H-1λ⁶-benzo[1,2,4]thiadiazin-3-one (8)

A solution of chlorosulfonyl isocyanate (17 mL, 195 mmol.) was dissolved in 150 mL of nitroethane and cooled to −40° C. A solution of 4-methoxyaniline (Z) (20 g, 162 mmol) in 100 mL of nitroethane was then added drop-wise from a dropper funnel with stirring. After the addition was completed, the reaction was stirred for an additional 5 minutes and aluminum chloride (25 g, 195 mmol) was added. The mixture was then quickly heated to 110° C. with stirring for 20 minutes. The crude material was then poured onto ice and the precipitate was collected by suction filtration, washed with cold water, and dried in vacuo to produce 35 g of the desired product (8) as a purple powder in 95% yield. $^1$H NMR (400 MHz, DMSO-$d_6$): δ 11.05 (s, 1H), 7.2 (m, 3H), 3.78 (s, 3H), 3.6 (br, 1H).

2-Amino-5-methoxy-benzenesulfonamide (9)

A solution of 8 (15 g, 65.7 mmol) was dissolved in 140 mL of 50% aqueous sulfuric acid. The solution was then heated to 130° C. for 6 hours. The solution was then poured over ice and neutralized at 0° C. with the addition of saturated aqueous sodium hydroxide. The mixture was then extracted with ethyl acetate. The organic phase was washed with brine, and dried over magnesium sulfate, filtered and dried in vacuo to produce 8.1 g of the desired product (2) as a brown solid in 60% yield. See procedure described in Girard, Y, et al., *J. Chem. Soc. Perkin Trans* 1, 1043-1047 (1979). $^1$H NMR (400 MHz, DMSO-$d_6$): δ 7.19 (s, 2H), 7.07 (d, 1H, J=2.8 Hz), 6.90 (dd, 1H, J=8.8 Hz, $J_2$=2.8 Hz), 6.73 (d, 1H, J=8.8 Hz), 5.40 (s, 2H), 3.65 (s, 3H).

N-(4-Methoxy-2-sulfamoyl-phenyl)-malonamic acid ethyl ester (10)

A neat suspension of 9 (8.0 g, 40 mmol) in diethylmalonate (14.1 g, 82 mmol) was heated to 160° C. for 60 minutes then cooled to room temperature. The mixture was triturated in hexane and decanted twice. The mixture was then triturated in diethyl ether and decanted twice. The remaining solid was then dried in vacuo to produce 8.8 g of the desired product (10) as a brown solid in 70% yield. $^1$H NMR (400 MHz, DMSO-$d_6$): δ 9.39 (s, 1H), 7.72 (d, 1H, J=8.8 Hz), 7.46 (s, 2H), 7.34 (m, 1H), 7.16 (m, 1H), 4.10 (m, 2H), 3.78 (s, 3H), 3.54 (s, 2H), 1.95 (m, 3H).

(7-Methoxy-1,1-dioxo-1,4-dihydro-1λ⁶-benzo[1,2,4]thiadiazin-3-yl)-acetic acid ethyl ester (4a)

A mixture of 10 (8.0 g, 28 mmol) in phosphorous oxychloride (150 mL, 1.64 mol) was heated to reflux for 2.5 hours, then cooled to room temperature and concentrated in vacuo. The residue was then dissolved in ethyl acetate and neutralized with saturated aqueous sodium bicarbonate. The organic phase was washed with 2 N hydrochloric acid and then brine, dried over magnesium sulfate, filtered, and concentrated in vacuo. The solid product was then triturated in diethyl ether to produce 6.6 g of the desired product (4a) as a brown solid in 79% yield. See procedure described in International Patent Application No. PCT/US03/16374. $^1$H NMR (400 MHz, DMSO-$d_6$): δ12.20 (s, 1H), 7.27 (m, 2 H), 7.20 (s, 1H), 4.14 (q, 2H, J=7.2 Hz), 3.73 (s, 3H), 3.66 (s, 2H), 1.21 (t, 3H, J=7.6 Hz); LC-MS (ESI$^+$): m/e=299.1 [M+1]$^+$.

(7-Methoxy-1,1-dioxo-1,4-dihydro-1λ6-benzo[1,2,4]thiadiazin-3-yl)-acetic acid (10a)

To a slurry of (7-Methoxy-1,1-dioxo-1,4-dihydro-1λ⁶-benzo[1,2,4]thiadiazin-3-yl)-acetic acid ethyl ester (4a) (1.0 g, 3.35 mmol) in 5 mL of THF and 1 mL of DMF, 10 mL of 6.0 M of HCL in $H_2O$ was added and the reaction mixture was shaken at room temperature for 2 days or a week. The reaction mixture was diluted with brine, filtered, washed and collected the solid that was further dried under high vacuum overnight to give desired product of 705.4 mg as first batch of product (10a). The filtrate was extracted three times with EtOAc. The organic layer was dried over MgSO$_4$, filtered, concentrated under reduced pressure and further dried under high vacuum overnight to give the second batch of the desired product (10a) (185.2 mg). In total 890.6 mg of the compound 10a was obtained with 98.4% yield. This product was directly used in the next step without further purification. This reaction was repeated multiple times on a bigger scale and the yields varied from 85 to 98%.

(7-Hydroxy-1,1-dioxo-1,4-dihydro-1λ$^6$-benzo[1,2,4]thiadiazin-3-yl)-acetic acid (10c)

To a solution of compound 4a (1 g, 3.7 mmol) in dichloromethane (23 mL), a solution of 1.0 M of BBr$_3$ in dichloromethane was added dropwise at 0° C. over 5 minutes. The reaction mixture was stirred at 0° C. to room temperature overnight. LC-MS result confirmed the completion of the reaction. The reaction mixture was poured onto 50 mL of ice which was extracted with EtOAc (150 mL×3). The combined organic layer was dried over MgSO$_4$, filtered, concentrated under reduced pressure and further dried under high vacuum to give 826.8 mg of desired product (10c) as brown foam in 87.2% yield. This crude product was directly used in next step without further purification. LC-MS: (ESI$^+$) m/e=257.10 [M+1]$^+$ (exact ms: 256.02).

In a separate experiment, the above reaction was repeated on a bigger scale where 1.5 g (5.03 mmol) of starting material of 4a was used resulting in the crude product of 10c that was directly transferred to compound 4b.

(7-Hydroxy-1,1-dioxo-1,4-dihydro-1λ$^6$-benzo[1,2,4]thiadiazin-3-yl)-acetic acid ethyl ester (4b)

EtOH (15 mL) and 150 μL of H$_2$SO$_4$ (conc.) were added into the compound 10c (5.03 mmol) and the mixture was heated to 80° C. for 45 minutes with stirring. The solvent was partially evaporated to half of the original volume under reduced pressure. EtOAc (30 mL) was added and the resulted mixture was washed with H$_2$O (15 mL×3) via extraction. The aqueous layer was back extracted with EtOAc once (60 mL) and the combined organic layer was dried over anhydrous MgSO$_4$, filtered, concentrated to give the desired product (4b) (1.11 g) as a gray solid. This crude material was directly used in next step without further purification. LC-MS: (ESI$^+$) m/e=285.10 [M+1]$^+$ (exact ms: 284.05).

Scheme 10 Describes the Synthesis of the Intermediate 10b.

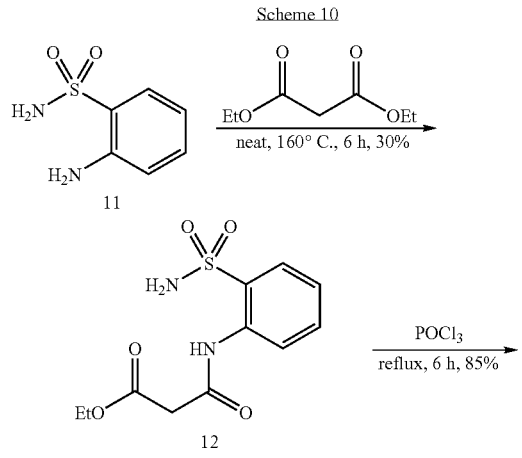

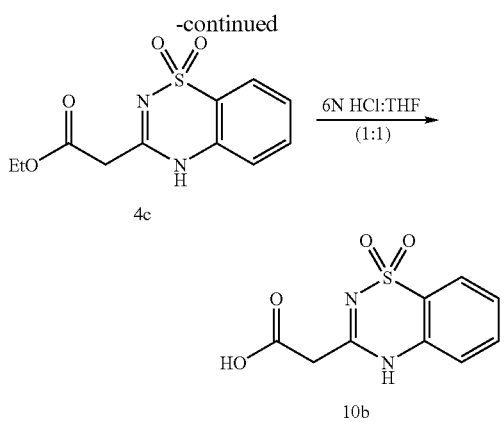

N-(2-Sulfamoyl-phenyl)-malonamic acid ethyl ester (12)

A suspension of 2-aminobenzenesulfonamide (11) (10.0 g, 58.1 mmol) in diethylmalonte (18.1 mL) was heated to 160° C. The reaction mixture became homogeneous upon heating and was continually stirred for 6 h at 160° C. Upon cooling to room temperature diethyl ether (150 mL) was added to the reaction mixture to induce precipitation. The precipitate was collected by vacuum filtration to give 12 as a purple solid (5.0 g, 30%). $^1$H NMR (400 MHz, D$_6$-DMSO) δ 9.57 (s, 1 H), 7.99 (d, J=8 Hz, 1 H), 7.84 (dd, J=8, 1 Hz, 1 H), 7.58 (td, J=8, 1 Hz, 1 H), 7.53 (s, 2 H), 7.31 (td, J=8, 1 Hz, 1 H), 4.14 (dt, J=7.2, 7.2 Hz, 2 H), 3.60 (s, 2 H), 1.22 (t, J=7.2H, 3 H). MS(ESI$^+$) m/e 537 [M+H]$^+$.

(1,1-Dioxo-1,4-dihydro-1λ$^6$-benzo[1,2,4]thiadiazin-3-yl)-acetic acid ethyl ester (4c)

A mixture of 12 (2.50 g, 8.73 mmol) in phosphorous oxychloride (50 mL) was heated under reflux for 6 h, cooled to room temperature, and concentrated in vacuo. The residue was dissolved in ethyl acetate (200 mL) and extracted with saturated Na$_2$CO$_3$ (100 mL). The organic layer was washed with 1 N HCl (50 mL), dried over MgSO$_4$, and concentrated in vacuo to give 4c (1.99 g, 85%) as a yellow solid. $^1$H NMR (400 MHz, D$_6$-DMSO) δ 12.22 (s, 1H), 7.79 (d, J=12 Hz, 1 H), 7.67 (t, J=10 Hz, 1 H), 7.45 (t, J=8 Hz, 1 H), 7.30 (d, J=8 Hz, 1 H), 4.15 (dt, J=7.2, 7.2 Hz, 2H), 3.69 (s, 2 H), 1.21 (t, J=7.2 Hz, 3 H).

(1,1-Dioxo-1,4-dihydro-1λ6-benzo[1,2,4]thiadiazin-3-yl)-acetic acid (10b)

A solution of 4c (1.98 g, 7.36 mmol) in THF (10 mL) and 6 N HCl (20 mL) was stirred for 2 days at room temperature. Chloroform (20 mL) was added to the solution to induce precipitation upon vigorous stirring 15 min. The precipitate was collected by vacuum filtration to give 10b (1.50 g, 85%) as a yellow solid. $^1$H NMR (400 MHz, D$_6$-DMSO) δ 12.25 (s, 1 H), 7.78 (d, J=8 Hz, 1 H), 7.66 (td, J=8, 1 Hz, 1 H), 7.44 (td, J=8, 1 Hz, 1 H), 7.32 (d, J=8 Hz, 1 H), 3.70 (br s, 1 H), 3.58 (s, 2 H).

Scheme 11 Describes the Synthesis of the Intermediate 14b.

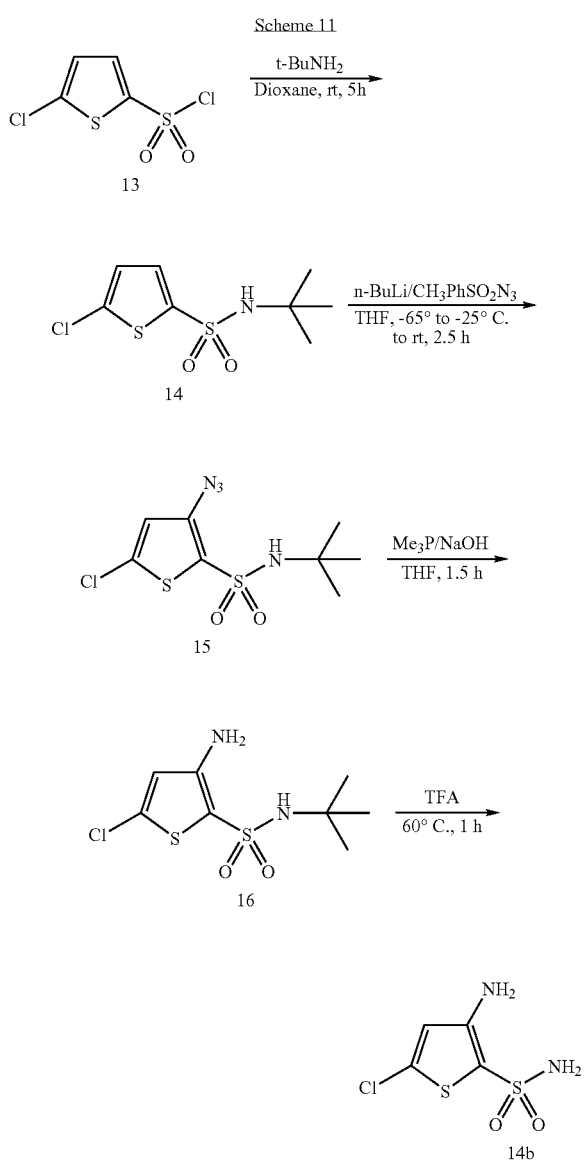

The intermediate 14b was prepared in a way similar to the procedure described in Hansen, J. B. et al. *J. Med. Chem.* 2002, 45, 4171-4187.

3-Amino-5-chloro-thiophene-2-sulfonic acid amide (14b)

$^1$H NMR (400 MHz, DMSO-$d_6$) δ 7.32 (br s, 2H), 6.58 (s, 1H), 5.93 (br s, 2H). LC-MS (ESI$^+$): m/e=213.20 [M+H]$^+$.

The corresponding HCl salt (3-Amino-5-chlorothiophene-2-sulfonamide hydrochloride) of 14b as HCl salt was also made according to the same literature method.

Biological Testing

The ability of compounds of Formula I to inhibit HCV replication can be demonstrated in the following in vitro assays.

NS5B Polymerase Inhibition Assay

Compounds were tested for HCV polymerase inhibition. Assays were performed in a 96-well streptavidin-coated FlashPlate using 50 nM enzyme, 0.5 µCi of [α-$^{33}$P]GTP, 0.63 µM GTP, and 250 nM 5'biotinylated oligo (rG$_{13}$)/poly rC in 20 mM Tris-HCl, pH 7.5, 5 mM MgCl$_2$, 20 mM NaCl, 5 mM dithiothreitol, and 0.1 g/L BSA. The reaction was stopped by aspiration after 75 min at 28° C. and the plate was washed several times. After washing, incorporated radioactivity was counted using a Microbeta scintillation counter.

Test results (IC$_{50}$ values) for compounds of Formula I are summarized in Table 1, wherein ++ means NS5B polymerase inhibition with IC$_{50}$ values less than 10 µM, + means IC$_{50}$ values between 10 µM and 50 µM and not determined means the IC50 value was not measured.

The measured mass for each compound in Table 1 corresponded to the predicted mass.

HCV Replicon Assay (Replicon EC$_{50}$ (µM))

Cell Line:

Human hepatocyte Huh7 cells containing the HCV dicistronic replicon were obtained from Ralf Bartenschlager at the University of Mainz, Germany. These cells are maintained under G418-Geneticin selection and passaged when 80-90% confluent.

This Huh7 cell line contains an autonomously replicating RNA element (replicon) incorporating the non-structural HCV elements necessary for replication, and upon which the survival of the replicon in the cell depends. Inhibition of any of the critical HCV functions by a compound leads to loss of the replicon copy number.

The assay is conducted by preparing sufficient 96-well plates containing Huh7 cells, wherein cells are seeded at 4500 cells/well, in 200 µl of final media volume. Cells are then incubated for 24 hours at 37° C., 5% CO$_2$, and 95% humidity before compound is added.

Eight point half-log concentration response assays are conducted to determine potency/EC$_{50}$ of Formula I compounds to inhibit HCV replicon replication. The final percent DMSO acceptable in this assay system is 0.5%. Compounds are diluted in media in an appropriate format and 50 µl of each drug dilution is added to each well. Cells are then incubated with compounds for 3 days at 37° C., 5% CO$_2$, and 95% humidity.

Quantification of RNA is performed by bDNA (branched DNA) technology from genospectra using NS3 as a RNA viral marker and GAPDH as a cellular RNA marker. Cell cytotoxicity is gauged by GAPDH level.

After 72 h exposure the media was discarded from the assay plate and the cell monolayers were lysed by addition of 150 µL lysis mixture (Genospectra) with incubation at 53° C. for 45 minutes. Following incubation, each lysate was thoroughly mixed and 5 µL (NS3 probe) or 10 µL (GAPDH probe) of each lysate was then transferred to the capture plate and analyzed by bDNA assay.

| | Structure | Name | NS5B Polymerase IC50 |
|---|---|---|---|
| 1 | 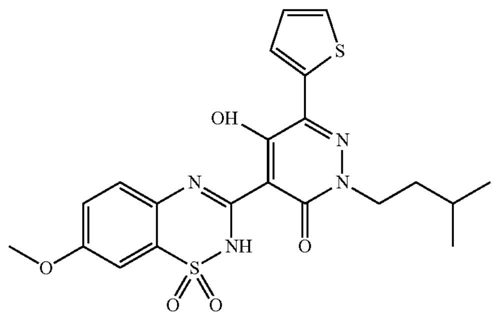 | 5-Hydroxy-4-(7-methoxy-1,1-dioxo-1,2-dihydro-1$\lambda^6$-benzo[1,2,4]thiadiazin-3-yl)-2-(3-methyl-butyl)-6-thiophen-2-yl-2H-pyridazin-3-one | ++ |
| 2 | 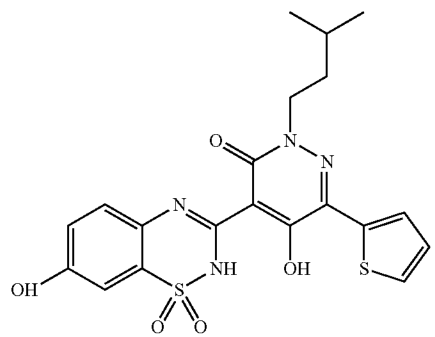 | 5-Hydroxy-4-(7-hydroxy-1,1-dioxo-1,2-dihydro-1$\lambda^6$-benzo[1,2,4]thiadiazin-3-yl)-2-(3-methyl-butyl)-6-thiophen-2-yl-2H-pyridazin-3-one | ++ |
| 3 | 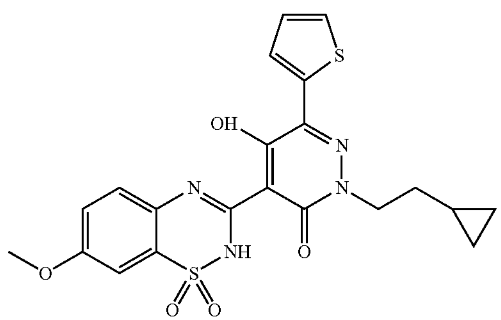 | 2-(2-Cyclopropyl-ethyl)-5-hydroxy-4-(7-methoxy-1,1-dioxo-1,2-dihydro-1$\lambda^6$-benzo[1,2,4]thiadiazin-3-yl)-6-thiophen-2-yl-2H-pyridazin-3-one | ++ |

-continued

| | Structure | Name | NS5B Polymerase IC50 |
|---|---|---|---|
| 4 | 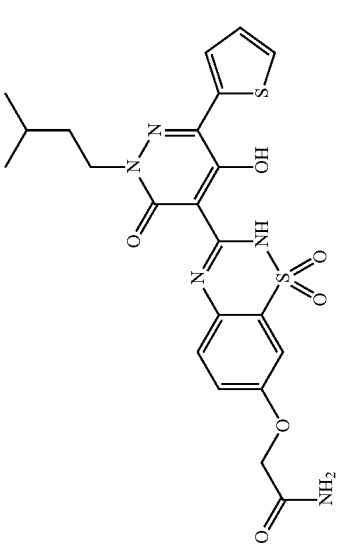 | 2-{3-[5-Hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-acetamide | ++ |
| 5 | 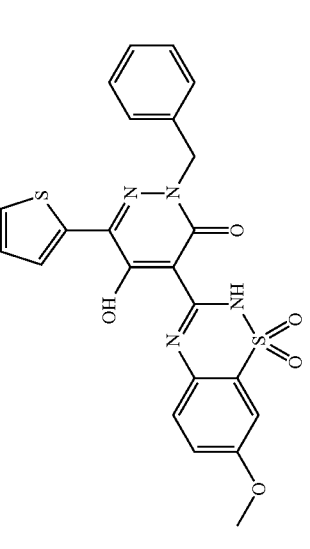 | 2-Benzyl-5-hydroxy-4-(7-methoxy-1,1-dioxo-1,2-dihydro-1$\lambda^6$-benzo[1,2,4]thiadiazin-3-yl)-6-thiophen-2-yl-2H-pyridazin-3-one | + |
| 6 | 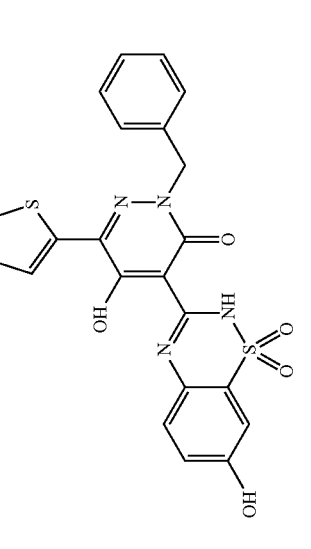 | 2-Benzyl-5-hydroxy-4-(7-hydroxy-1,1-dioxo-1,2-dihydro-1$\lambda^6$-benzo[1,2,4]thiadiazin-3-yl)-6-thiophen-2-yl-2H-pyridazin-3-one | ++ |

| | Structure | Name | NS5B Polymerase IC50 |
|---|---|---|---|
| 7 | 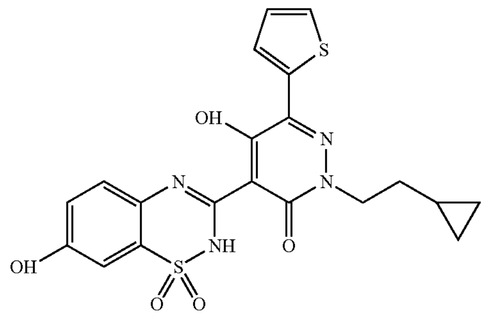 | 2-(2-Cyclopropyl-ethyl)-5-hydroxy-4-(7-hydroxy-1,1-dioxo-1,2-dihydro-1λ⁶-benzo[1,2,4]thiadiazin-3-yl)-6-thiophen-2-yl-2H-pyridazin-3-one | ++ |
| | | 2-[3-(2-Benzyl-5-hydroxy-3-oxo-6-thiophen-2-yl-2,3-dihydro-pyridazin-4-yl)-1,1-dioxo-1,2-dihydro-1λ⁶-benzo[1,2,4]thiadiazin-7-yloxy]-acetamide | |
| 9 | 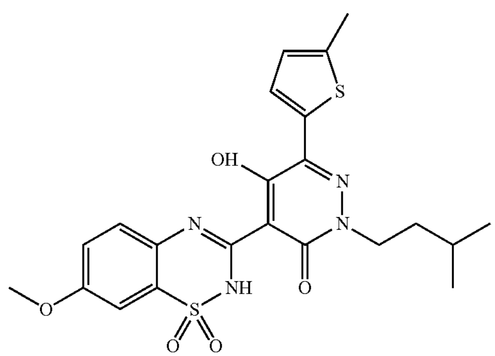 | 5-Hydroxy-4-(7-methoxy-1,1-dioxo-1,2-dihydro-1λ⁶-benzo[1,2,4]thiadiazin-3-yl)-2-(3-methyl-butyl)-6-(5-methyl-thiophen-2-yl)-2H-pyridazin-3-one | + |

| | Structure | Name | NS5B Polymerase IC50 |
|---|---|---|---|
| 10 | 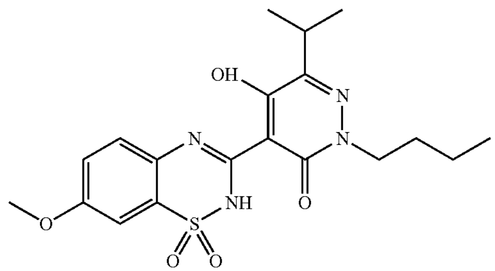 | 2-Butyl-5-hydroxy-6-isopropyl-4-(7-methoxy-1,1-dioxo-1,2-dihydro-1λ⁶-benzo[1,2,4]thiadiazin-3-yl)-2H-pyridazin-3-one | + |
| 11 | 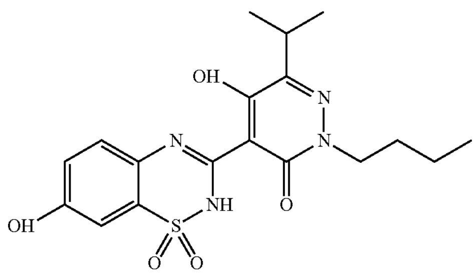 | 2-Butyl-5-hydroxy-4-(7-hydroxy-1,1-dioxo-1,2-dihydro-1λ⁶-benzo[1,2,4]thiadiazin-3-yl)-6-isopropyl-2H-pyridazin-3-one | ++ |
| 12 | 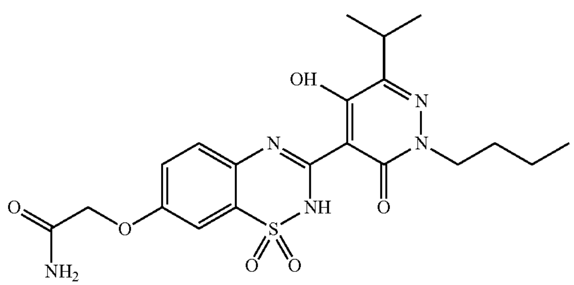 | 2-[3-(2-Butyl-5-hydroxy-6-isopropyl-3-oxo-2,3-dihydro-pyridazin-4-yl)-1,1-dioxo-1,2-dihdyro-1λ⁶-benzo[1,2,4]thiadiazin-7-yloxy]-actamide | ++ |

-continued

| | Structure | Name | NS5B Polymerase IC50 |
|---|---|---|---|
| 13 | 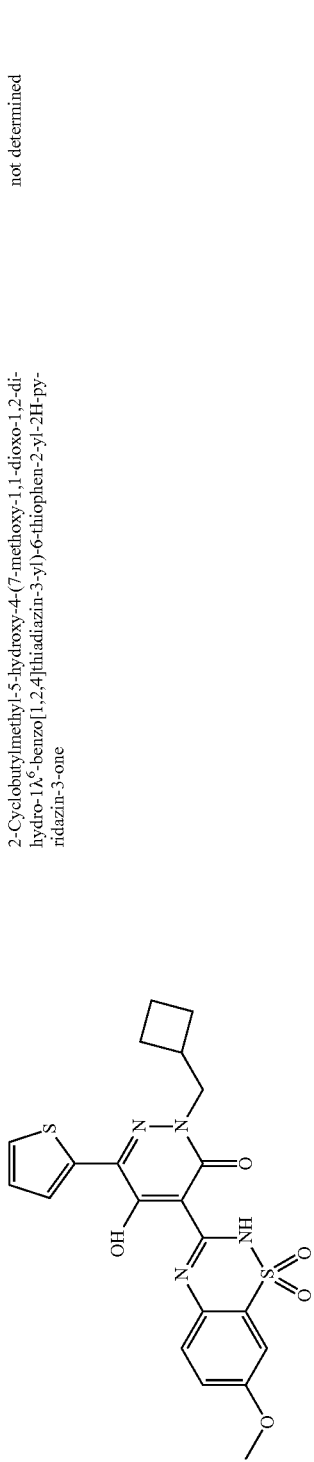 | 2-Cyclobutylmethyl-5-hydroxy-4-(7-methoxy-1,1-dioxo-1,2-dihydro-1$\lambda^6$-benzo[1,2,4]thiadiazin-3-yl)-6-thiophen-2-yl-2H-pyridazin-3-one | not determined |
| 14 | 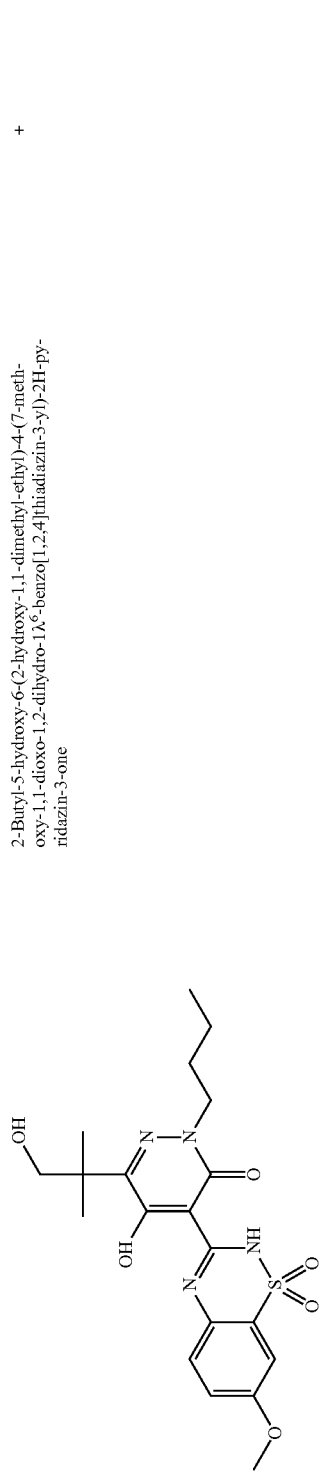 | 2-Butyl-5-hydroxy-6-(2-hydroxy-1,1-dimethyl-ethyl)-4-(7-methoxy-1,1-dioxo-1,2-dihydro-1$\lambda^6$-benzo[1,2,4]thiadiazin-3-yl)-2H-pyridazin-3-one | + |
| 15 | 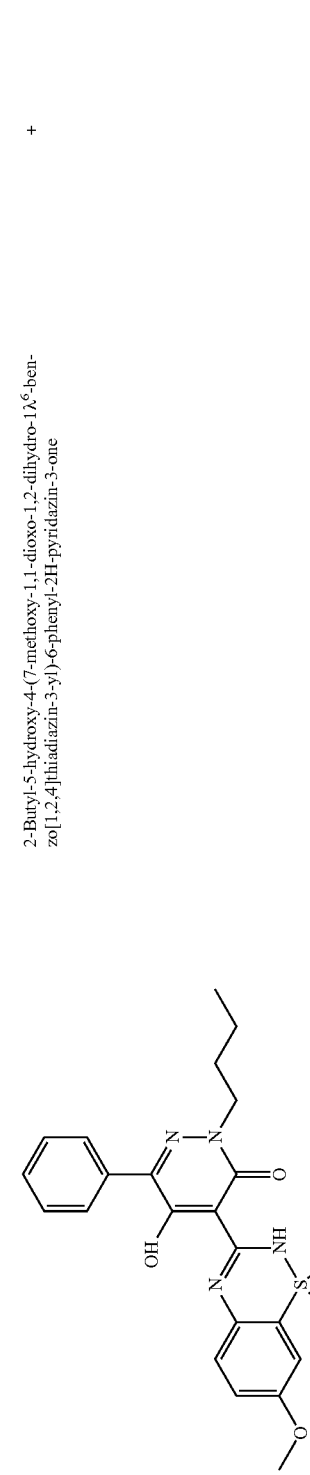 | 2-Butyl-5-hydroxy-4-(7-methoxy-1,1-dioxo-1,2-dihydro-1$\lambda^6$-benzo[1,2,4]thiadiazin-3-yl)-6-phenyl-2H-pyridazin-3-one | + |

| | Structure | Name | NS5B Polymerase IC50 |
|---|---|---|---|
| 16 | 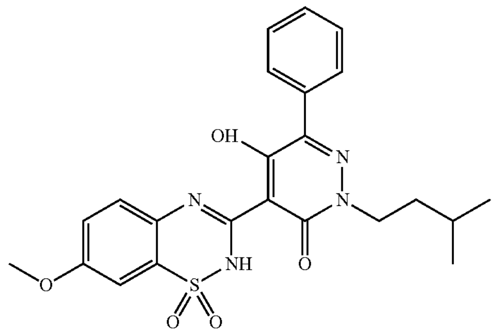 | 5-Hydroxy-4-(7-methoxy-1,1-dioxo-1,2-dihydro-1λ⁶-benzo[1,2,4]thiadiazin-3-yl)-2-(3-methyl-butyl)-6-phenyl-2H-pyridazin-3-one | + |
| 17 | 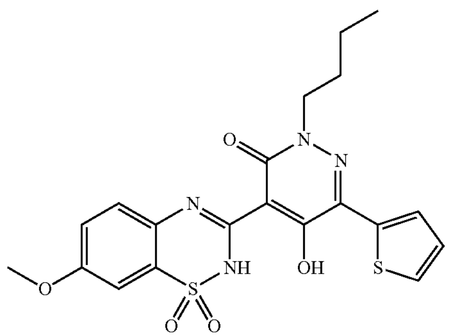 | 2-Butyl-5-hydroxy-4-(7-methoxy-1,1-dioxo-1,2-dihydro-1λ⁶-benzo[1,2,4]thiadiazin-3-yl)-6-thiophen-2-yl-2H-pyridazin-3-one | ++ |
| 18 | 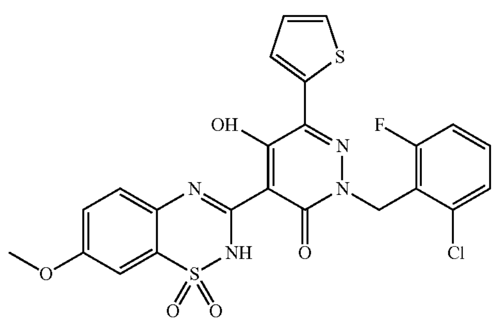 | 2-(2-Chloro-6-fluoro-benzyl)-5-hydroxy-4-(7-methoxy-1,1-dioxo-1,2-dihydro-1λ⁶-benzo[1,2,4]thiadiazin-3-yl)-6-thiophen-2-yl-2H-pyridazin-3-one | not determined |

-continued

| | Structure | Name | NS5B Polymerase IC50 |
|---|---|---|---|
| 19 | 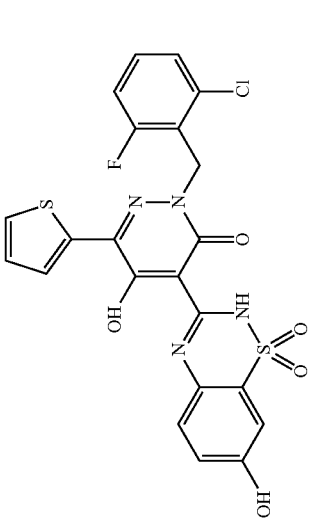 | 2-(2-Chloro-6-fluoro-benzyl)-5-hydroxy-4-(7-hydroxy-1,1-di-oxo-1,2-dihydro-1λ⁶-benzo[1,2,4]thiadiazin-3-yl)-6-thio-phen-2-yl-2H-pyridazin-3-one | + |
| 20 | 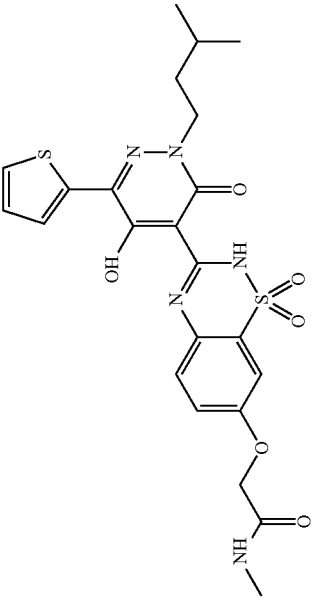 | 2-{3-[5-Hydroxy-2-(3-methyl-butyl)-3-oxo-6-thiophen-2-yl-2,3-di-hydro-pyridazin-4-yl]-1,1-dioxo-1,2-dihydro-1λ⁶-ben-zo[1,2,4]thiadiazin-7-yloxy}-N-methyl-acetamide | ++ |
| 21 | 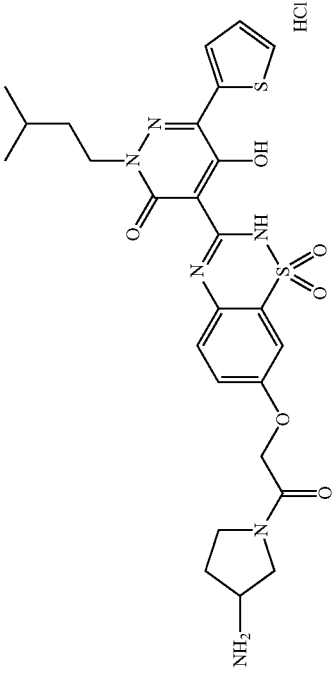 | 4-{7-[2-(3-Amino-pyrrolidin-1-yl)-2-oxo-ethoxy]-1,1-dioxo-1,2-di-hydro-1λ⁶-benzo[1,2,4]thiadiazin-3-yl}-5-hydroxy-2-(3-methyl-butyl)-6-thiophen-2-yl-2H-pyridazin-3-one | ++ |

| | Structure | Name | NS5B Polymerase IC50 |
|---|---|---|---|
| 22 | 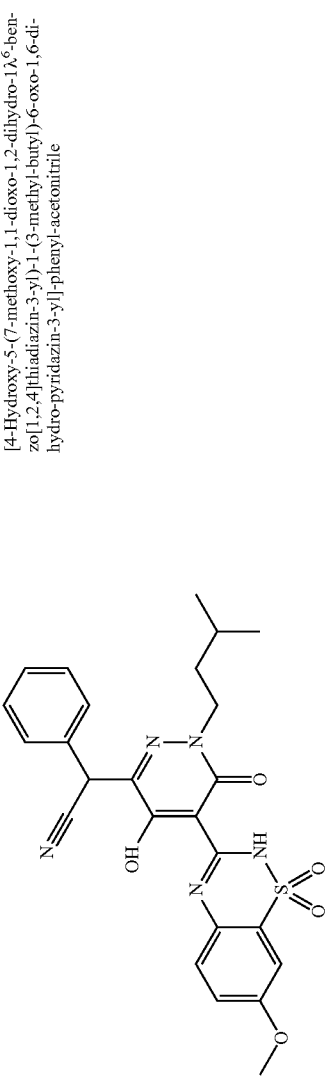 | [4-Hydroxy-5-(7-methoxy-1,1-dioxo-1,2-dihydro-1λ⁶-benzo[1,2,4]thiadiazin-3-yl)-1-(3-methyl-butyl)-6-oxo-1,6-dihydro-pyridazin-3-yl]-phenyl-acetonitrile | not determined |
| 23 | 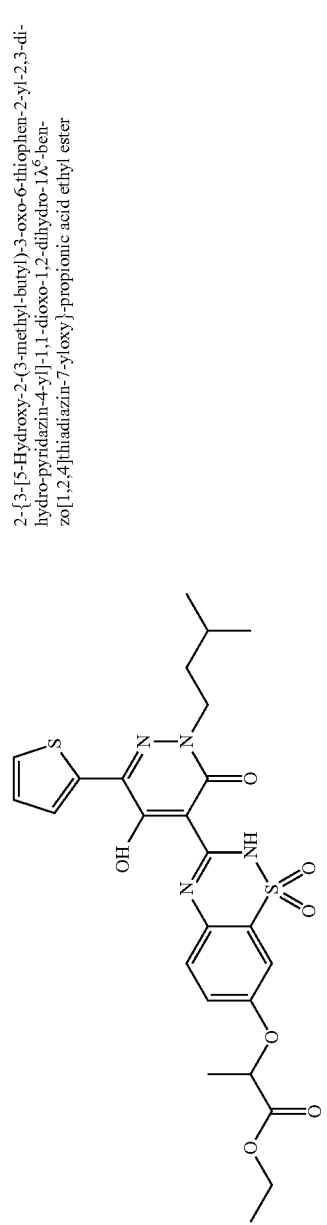 | 2-{3-[5-Hydroxy-2-(3-methyl-butyl)-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-propionic acid ethyl ester | ++ |
| 24 | 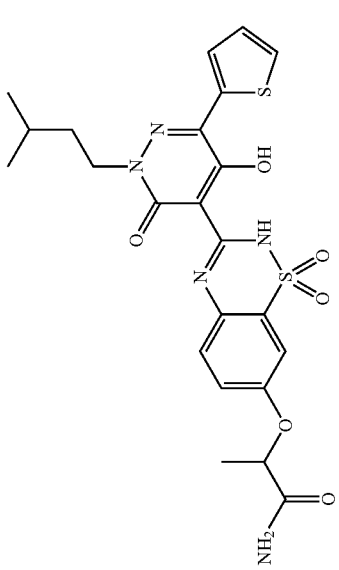 | 2-{3-[5-Hydroxy-2-(3-methyl-butyl)-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-propionamide | ++ |

-continued
| | Structure | Name | NS5B Polymerase IC50 |
|---|---|---|---|
| 25 | 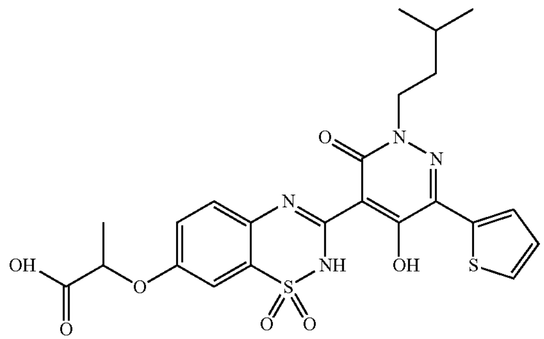 | 2-{3-[5-Hydroxy-2-(3-methyl-butyl)-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-propionic acid | ++ |
| 26 | 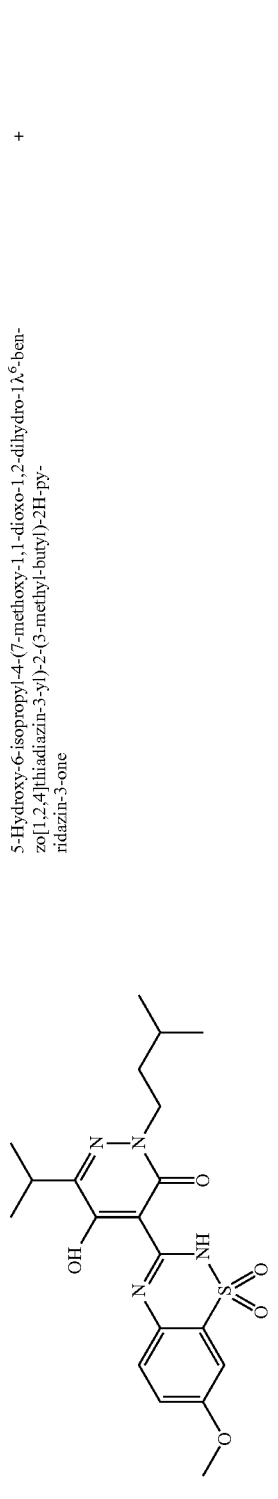 | 5-Hydroxy-6-isopropyl-4-(7-methoxy-1,1-dioxo-1,2-dihydro-1λ⁶-benzo[1,2,4]thiadiazin-3-yl)-2-(3-methyl-butyl)-2H-pyridazin-3-one | + |
| 27 | 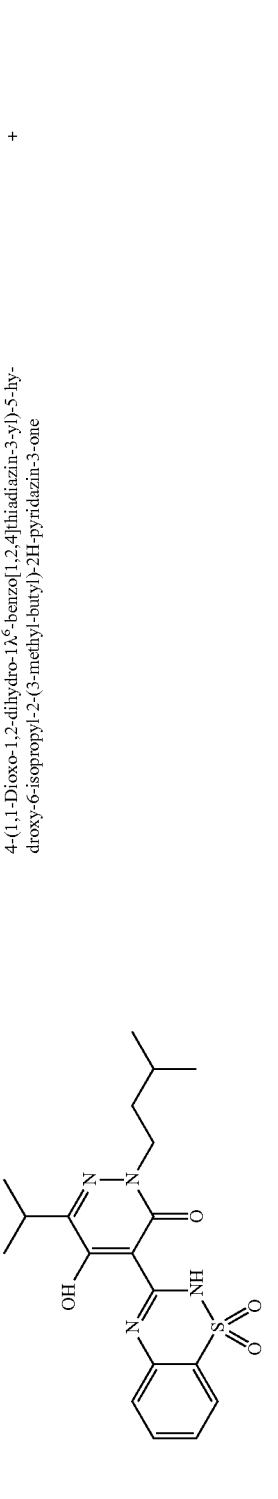 | 4-(1,1-Dioxo-1,2-dihydro-1λ⁶-benzo[1,2,4]thiadiazin-3-yl)-5-hydroxy-6-isopropyl-2-(3-methyl-butyl)-2H-pyridazin-3-one | + |

| | Structure | Name | NS5B Polymerase IC50 |
|---|---|---|---|
| 28 | 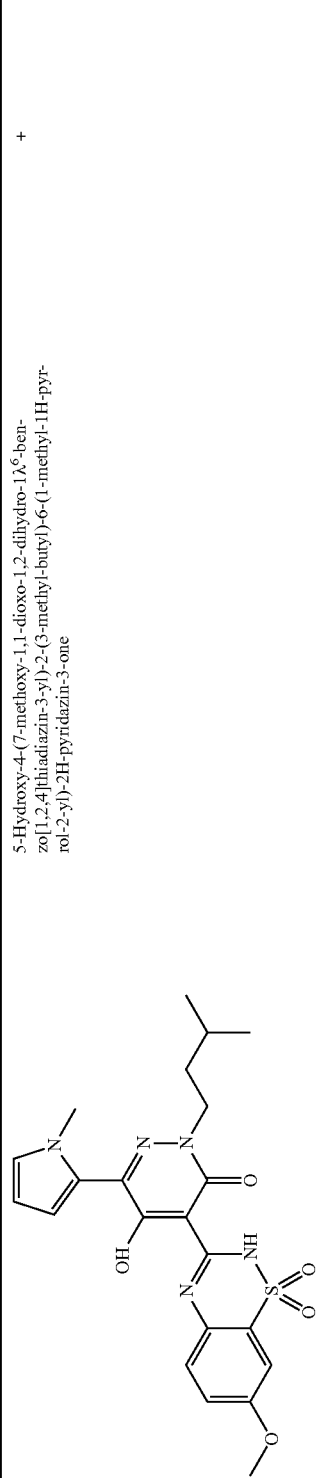 | 5-Hydroxy-4-(7-methoxy-1,1-dioxo-1,2-dihydro-1λ⁶-benzo[1,2,4]thiadiazin-3-yl)-2-(3-methyl-butyl)-6-(1-methyl-1H-pyrrol-2-yl)-2H-pyridazin-3-one | + |
| 29 | 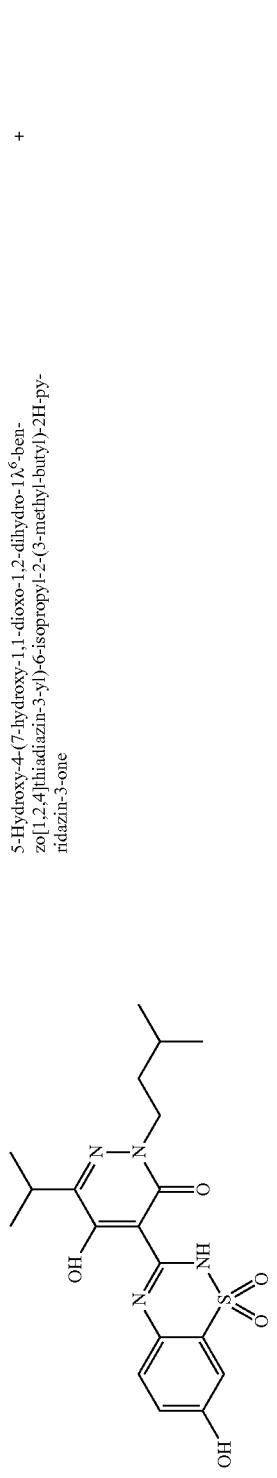 | 5-Hydroxy-4-(7-hydroxy-1,1-dioxo-1,2-dihydro-1λ⁶-benzo[1,2,4]thiadiazin-3-yl)-6-isopropyl-2-(3-methyl-butyl)-2H-pyridazin-3-one | + |
| 30 | 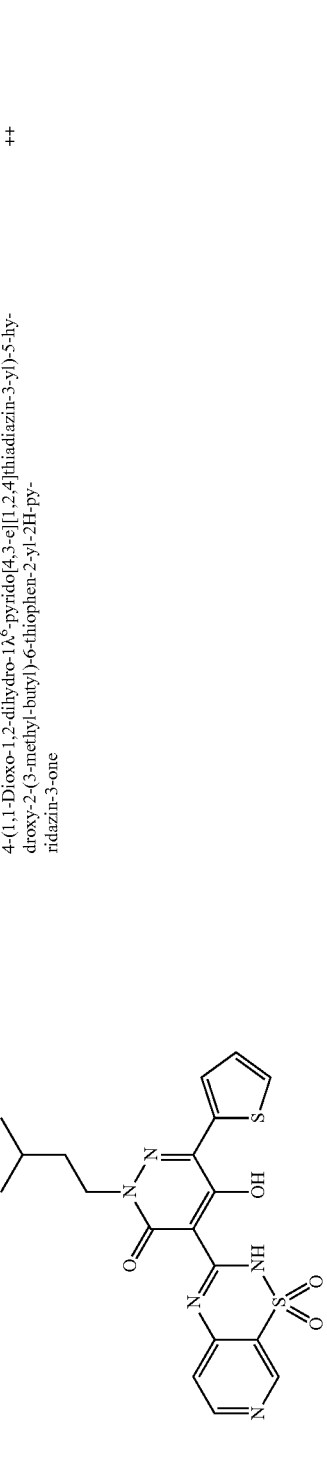 | 4-(1,1-Dioxo-1,2-dihydro-1λ⁶-pyrido[4,3-e][1,2,4]thiadiazin-3-yl)-5-hydroxy-2-(3-methyl-butyl)-6-thiophen-2-yl-2H-pyridazin-3-one | ++ |

| | Structure | Name | NS5B Polymerase IC50 |
|---|---|---|---|
| 31 | 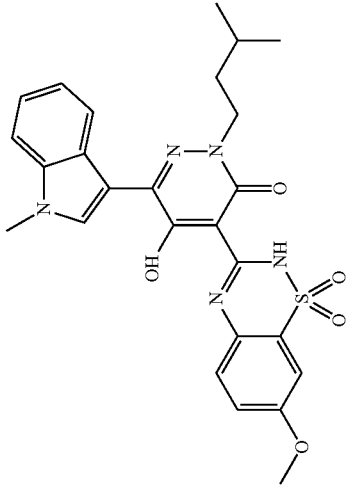 | 5-Hydroxy-4-(7-methoxy-1,1-dioxo-1,2-dihydro-1λ⁶-benzo[1,2,4]thiadiazin-3-yl)-2-(3-methyl-butyl)-6-(1-methyl-1H-indol-3-yl)-2H-pyridazin-3-one | not determined |
| 32 | 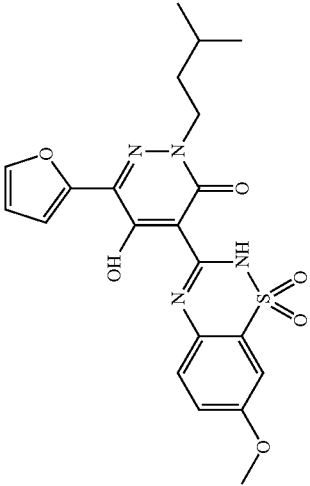 | 6-Furan-2-yl-5-hydroxy-4-(7-methoxy-1,1-dioxo-1,2-dihydro-1λ⁶-benzo[1,2,4]thiadiazin-3-yl)-2-(3-methyl-butyl)-2H-pyridazin-3-one | ++ |
| 33 | 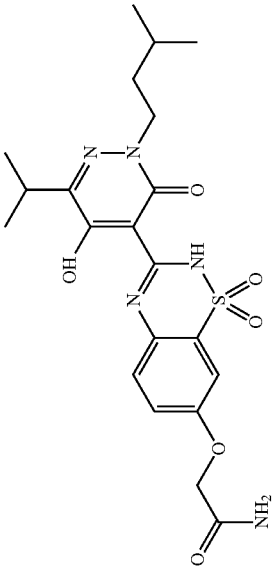 | 2-{3-[5-Hydroxy-6-isopropyl-2-(3-methyl-butyl)-3-oxo-2,3-dihydro-pyridazin-4-yl]-1,1-dioxo-1,2-dihydro-1λ⁶-benzo[1,2,4]thiadiazin-7-yloxy}-acetamide | ++ |

-continued

| | Structure | Name | NS5B Polymerase IC50 |
|---|---|---|---|
| 34 | 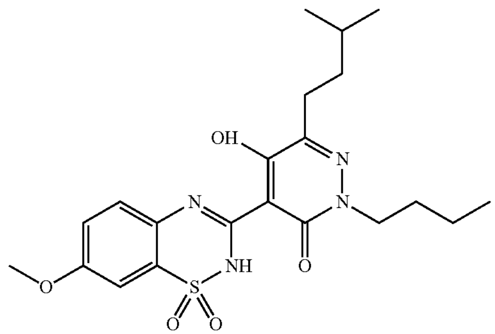 | 2-Butyl-5-hydroxy-4-(7-methoxy-1,1-dioxo-1,2-dihydro-1λ⁶-benzo[1,2,4]thiadiazin-3-yl)-6-(3-methyl-butyl)-2H-pyridazin-3-one | ++ |
| 35 | 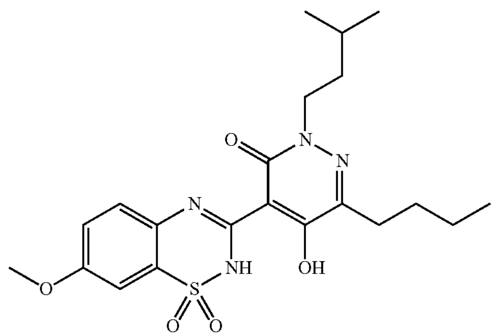 | 6-Butyl-5-hydroxy-4-(7-methoxy-1,1-dioxo-1,2-dihdyro-1λ⁶-benzo[1,2,4]thiadiazin-3-yl)-2-(3-methyl-butyl)-2H-pyridazin-3-one | ++ |
| 36 | 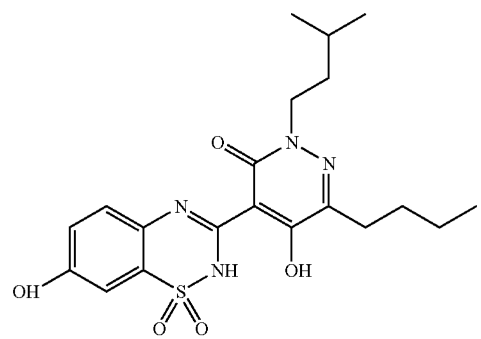 | 6-Butyl-5-hydroxy-4-(7-hydroxy-1,1-dioxo-1,2-dihydro-1λ⁶-benzo[1,2,4]thiadiazin-3-yl)-2-(3-methyl-butyl)-2H-pyridazin-3-one | ++ |

| | Structure | Name | NS5B Polymerase IC50 |
|---|---|---|---|
| 37 | 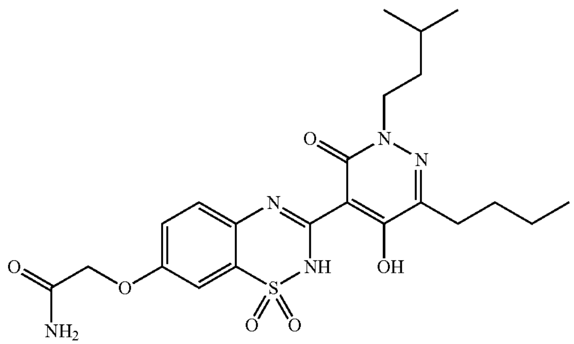 | 2-{3-[6-Butyl-5-hydroxy-2-(3-methyl-butyl)-3-oxo-2,3-dihydro-pyridazin-4-yl]-1,1-dioxo-1,2-dihydro-1λ⁶-benzo[1,2,4]thiadiazin-7-yloxy}-acetamide | ++ |
| 38 | 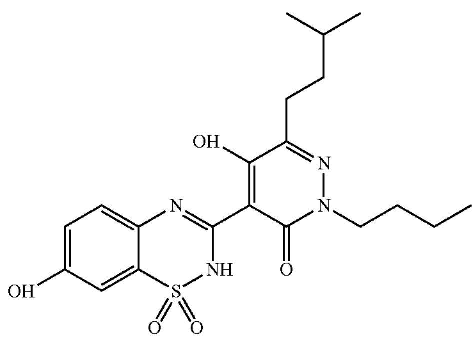 | 2-Butyl-5-hydroxy-4-(7-hydroxy-1,1-dioxo-1,2-dihydro-1λ⁶-benzo[1,2,4]thiadiazin-3-yl)-6-(3-methyl-butyl)-2H-pyridazin-3-one | ++ |
| 39 | 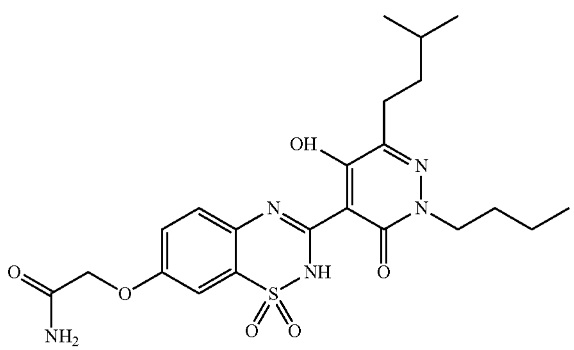 | 2-{3-[2-Butyl-5-hydroxy-6-(3-methyl-butyl)-3-oxo-2,3-dihydro-pyridazin-4-yl]-1,1-dioxo-1,2-dihydro-1λ⁶-benzo[1,2,4]thiadiazin-7-yloxy}-acetamide | ++ |

| | Structure | Name | NS5B Polymerase IC50 |
|---|---|---|---|
| 40 | 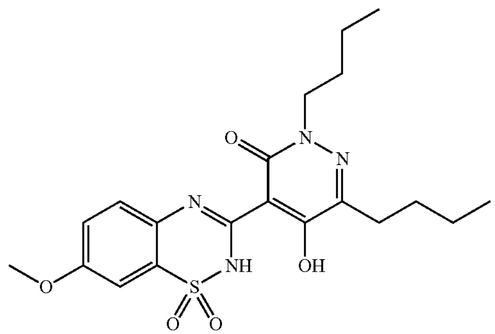 | 2,6-Dibutyl-5-hydroxy-4-(7-methoxy-1,1-dioxo-1,2-dihydro-1λ⁶-benzo[1,2,4]thiadiazin-3-yl)-2H-pyridazin-3-one | + |
| 41 | 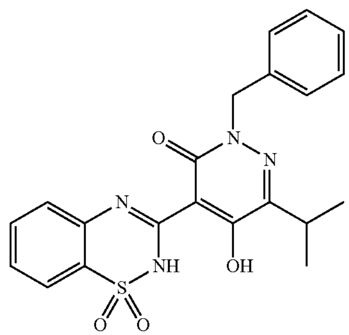 | 2-Benzyl-4-(1,1-dioxo-1,2-dihydro-1λ⁶-benzo[1,2,4]thiadiazin-3-yl)-5-hydroxy-6-isopropyl-2H-pyridazin-3-one | + |
| 42 | 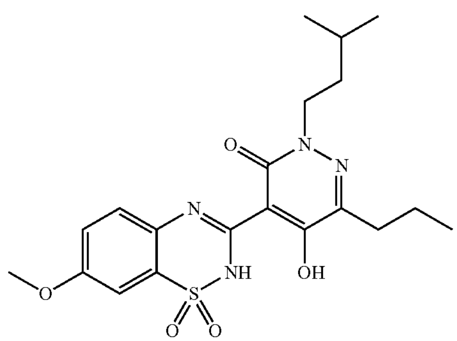 | 5-Hydroxy-4-(7-methoxy-1,1-dioxo-1,2-dihydro-1λ⁶-benzo[1,2,4]thiadiazin-3-yl)-2-(3-methyl-butyl)-6-propyl-2H-pyridazin-3-one | ++ |

| | Structure | Name | NS5B Polymerase IC50 |
|---|---|---|---|
| 43 | 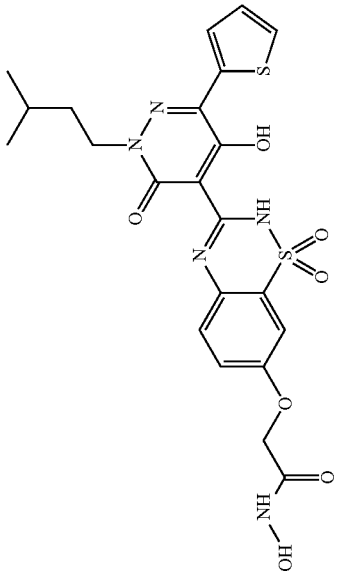 | N-Hydroxy-2-{3-[5-hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-acetamide | ++ |
| 44 | 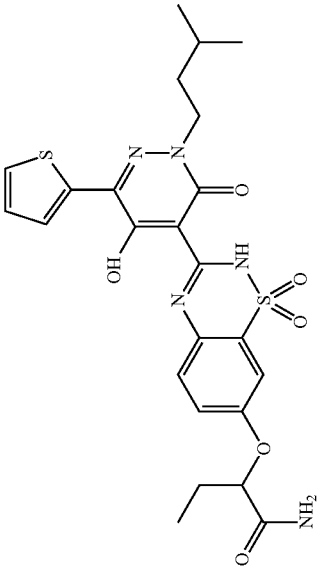 | 2-{3-[5-Hydroxy-2-(3-methyl-butyl)-3-oxo-6-thiophen-2-yl-2,3-dihydro-pyridazin-4-yl]-1,1-dioxo-1,2-dihydro-1$\lambda^6$-benzo[1,2,4]thiadiazin-7-yloxy}-butyramide | ++ |
| 45 | 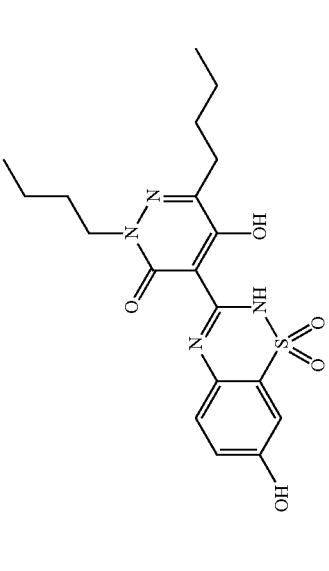 | 2,6-Dibutyl-5-hydroxy-4-(7-hydroxy-1,1-dioxo-1,2-dihydro-1$\lambda^6$-benzo[1,2,4]thiadiazin-3-yl)-2H-pyridazin-3-one | ++ |

| | Structure | Name | NS5B Polymerase IC50 |
|---|---|---|---|
| 46 | 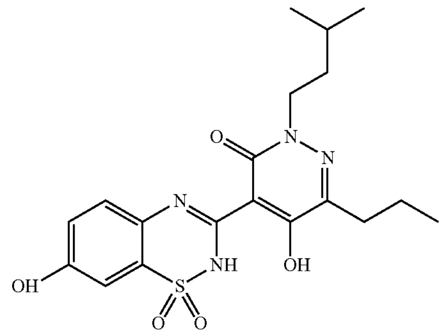 | 5-Hydroxy-4-(7-hydroxy-1,1-dioxo-1,2-dihydro-1λ⁶-benzo[1,2,4]thiadiazin-3-yl)-2-(3-methyl-butyl)-6-propyl-2H-pyridazin-3-one | ++ |
| 47 | 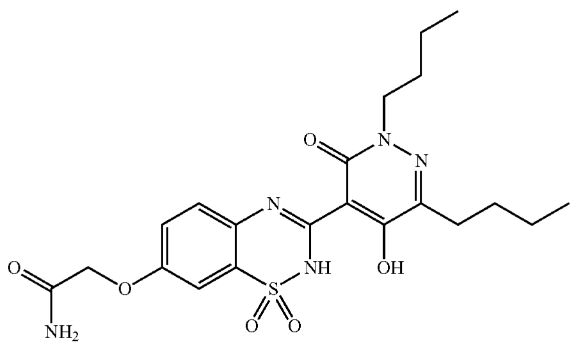 | 2-[3-(2,6-Dibutyl-5-hydroxy-3-oxo-2,3-dihydro-pyridazin-4-yl)-1,1-dioxo-1λ⁶-benzo[1,2,4]thiadiazin-7-yloxy]-acetamide | ++ |
| 48 | 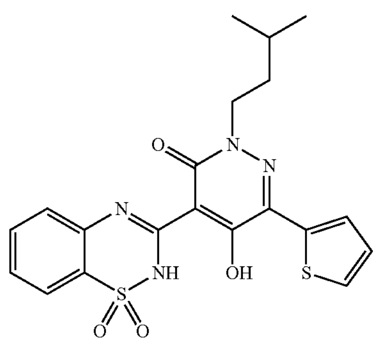 | 4-(1,1-Dioxo-1,2-dihydro-1λ⁶-benzo[1,2,4]thiadiazin-3-yl)-5-hydroxy-2-(3-methyl-butyl)-6-thiophen-2-yl-2H-pyridazin-3-one | ++ |

-continued

| | Structure | Name | NS5B Polymerase IC50 |
|---|---|---|---|
| 49 | 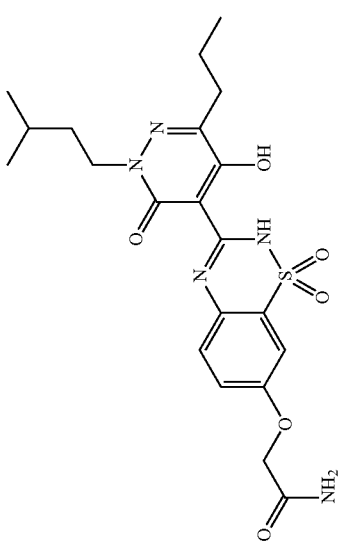 | 2-{3-[5-Hydroxy-2-(3-methyl-butyl)-3-oxo-6-propyl-2,3-dihydro-pyridazin-4-yl]-1,1-dioxo-1,2-dihydro-1$\lambda^6$-benzo[1,2,4]thiadiazin-7-yloxy}-acetamide | ++ |
| 50 | 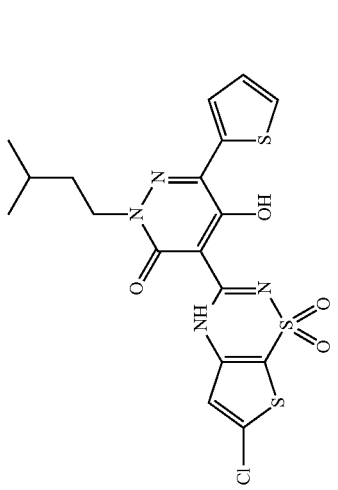 | 4-(2-Chloro-7,7-dioxo-4,7-dihydro-1,7$\lambda^6$-dithia-4,6-diaza-inden-5-yl)-5-hydroxy-2-(3-methyl-butyl)-6-thiophen-2-yl-2H-pyridazin-3-one | + |
| 51 | 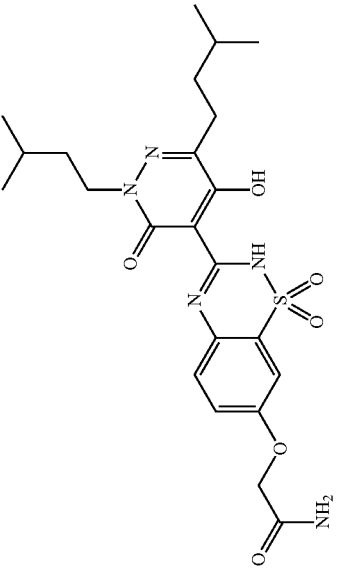 | 2-{3-[5-Hydroxy-2,6-bis-(3-methyl-butyl)-3-oxo-2,3-dihydro-pyridazin-4-yl]-1,1-dioxo-1,2-dihydro-1$\lambda^6$-benzo[1,2,4]thiadiazin-7-yloxy}-acetamide | ++ |

| | Structure | Name | NS5B Polymerase IC50 |
|---|---|---|---|
| 52 | 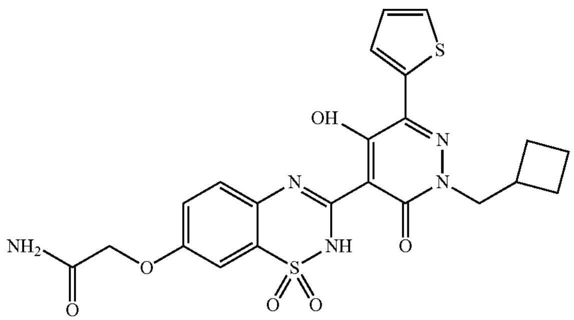 | 2-[3-(2-Cyclobutylmethyl-5-hydroxy-3-oxo-6-thiophen-2-yl-2,3-dihydro-pyridazin-4-yl)-1,1-dioxo-1,2-dihydro-1$\lambda^6$-benzo[1,2,4]thiadiazin-7-yloxy]-acetamide | ++ |
| 53 | 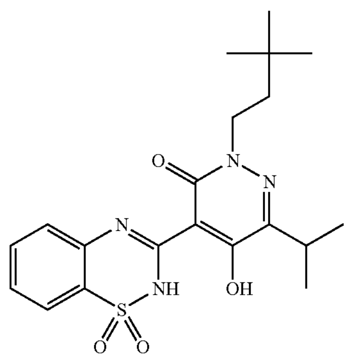 | 2-(3,3-Dimethyl-butyl)-4-(1,1-dioxo-1,2-dihydro-1$\lambda^6$-benzo[1,2,4]thiadiazin-3-yl)-5-hydroxy-6-isopropyl-2H-pyridazin-3-one | ++ |
| 54 | 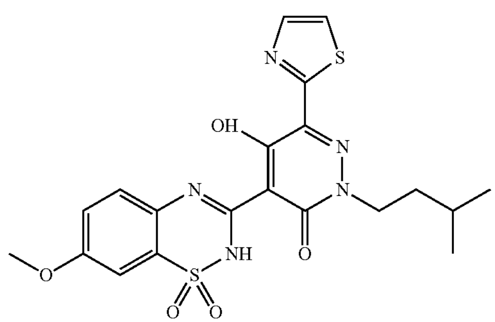 | 5-Hydroxy-4-(7-methoxy-1,1-dioxo-1,2-dihydro-1$\lambda^6$-benzo[1,2,4]thiadiazin-3-yl)-2-(3-methyl-butyl)-6-thiazol-2-yl-2H-pyridazin-3-one | ++ |

| | Structure | Name | NS5B Polymerase IC50 |
|---|---|---|---|
| 55 | 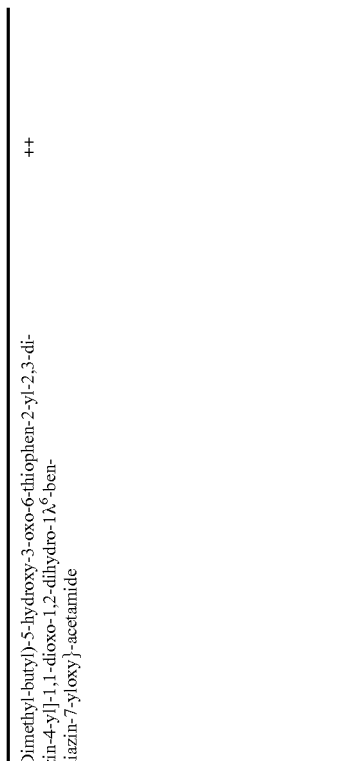 | 2-{3-[2-(3,3-Dimethyl-butyl)-5-hydroxy-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-acetamide | ++ |
| 56 | 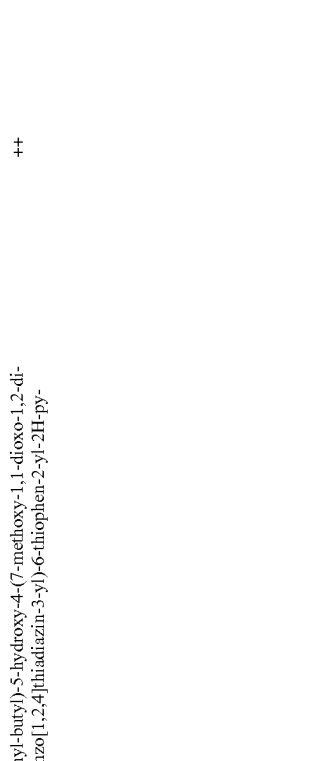 | 2-(3,3-Dimethyl-butyl)-5-hydroxy-4-(7-methoxy-1,1-dioxo-1,2-dihydro-1λ⁶-benzo[1,2,4]thiadiazin-3-yl)-6-thiophen-2-yl-2H-pyridazin-3-one | ++ |
| 57 | 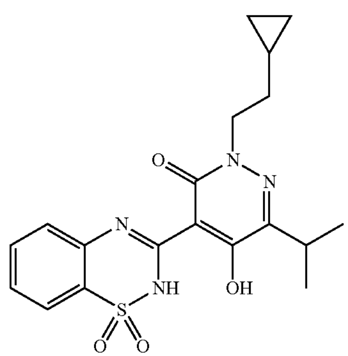 | 2-(2-Cyclopropyl-ethyl)-4-(1,1-dioxo-1,2-dihydro-1λ⁶-benzo[1,2,4]thiadiazin-3-yl)-5-hydroxy-6-isopropyl-2H-pyridazin-3-one | ++ |

-continued

| | Structure | Name | NS5B Polymerase IC50 |
|---|---|---|---|
| 58 | 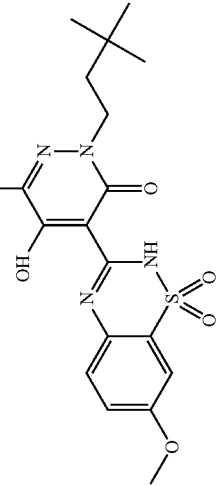 | 3-[1-(3,3-Dimethyl-butyl)-4-hydroxy-5-(7-methoxy-1,1-dioxo-1,2-dihydro-1λ⁶-benzo[1,2,4]thiadiazin-3-yl)-6-oxo-1,6-dihydro-pyridazin-3-yl]-propionitrile | + |
| 59 | 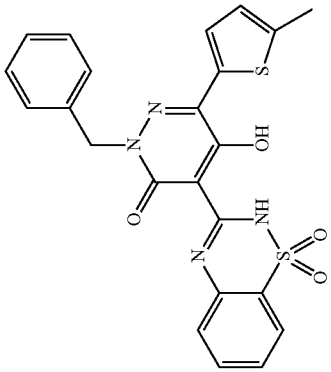 | 2-Benzyl-4-(1,1-dioxo-1,2-dihydro-1λ⁶-benzo[1,2,4]thiadiazin-3-yl)-5-hydroxy-6-(5-methyl-thiophen-2-yl)-2H-pyridazin-3-one | ++ |
| 60 | 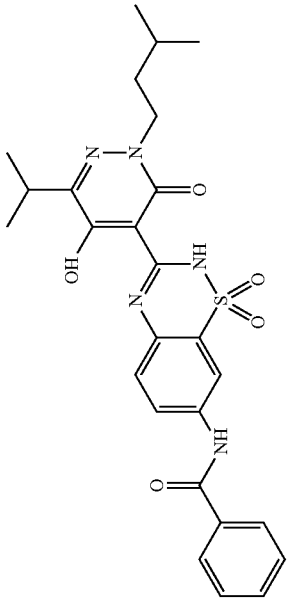 | N-{3-[5-Hydroxy-6-isopropyl-2-(3-methyl-butyl)-3-oxo-2,3-dihydro-pyridazin-4-yl]-1,1-dioxo-1,2-dihydro-1λ⁶-benzo[1,2,4]thiadiazin-7-yl}-benzamide | not determined |

| | Structure | Name | NS5B Polymerase IC50 |
|---|---|---|---|
| 61 | 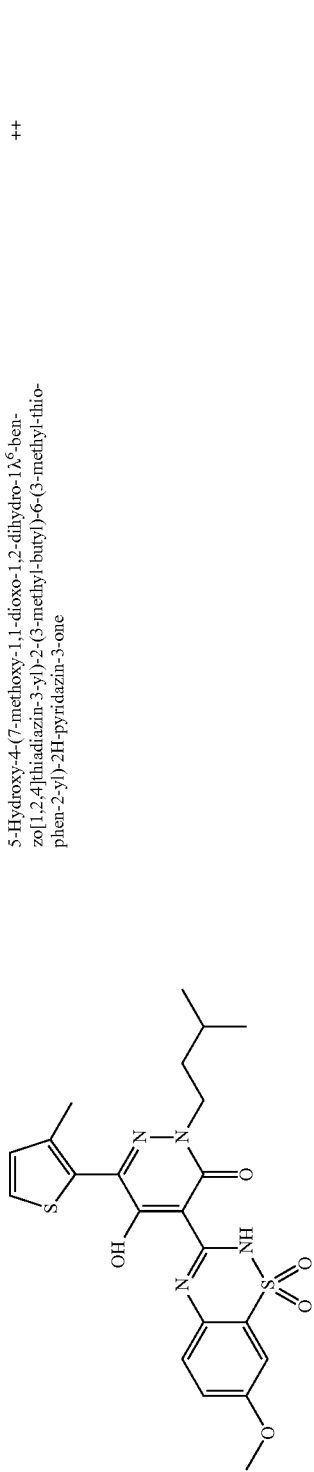 | 5-Hydroxy-4-(7-methoxy-1,1-dioxo-1,2-dihydro-1λ⁶-benzo[1,2,4]thiadiazin-3-yl)-2-(3-methyl-butyl)-6-(3-methyl-thiophen-2-yl)-2H-pyridazin-3-one | ++ |
| 62 | 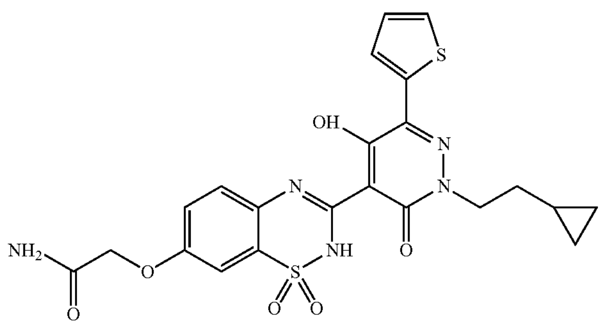 | 2-{3-[2-(2-Cyclopropyl-ethyl)-5-hydroxy-3-oxo-6-thiophen-2-yl-2,3-dihydro-pyridazin-4-yl]-1,1-dioxo-1,2-dihydro-1λ⁶-benzo[1,2,4]thiadiazin-7-yloxy}-acetamide | ++ |
| 63 | 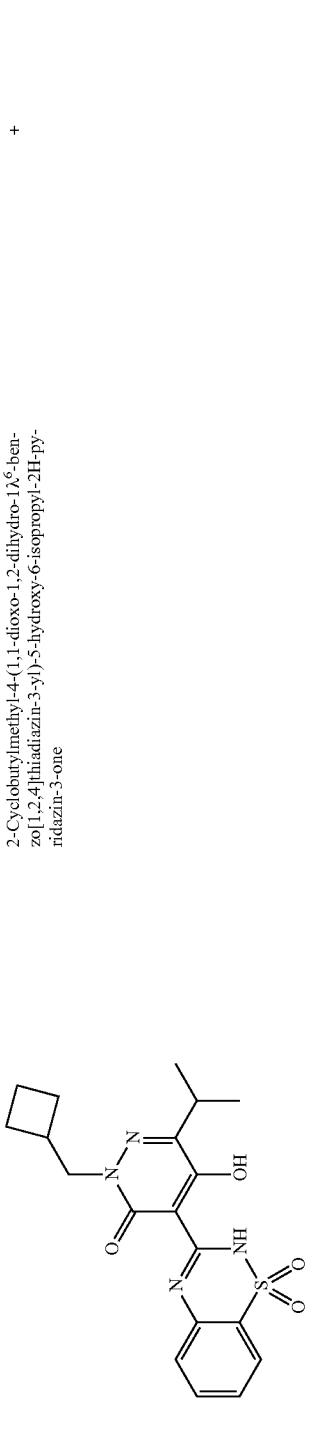 | 2-Cyclobutylmethyl-4-(1,1-dioxo-1,2-dihydro-1λ⁶-benzo[1,2,4]thiadiazin-3-yl)-5-hydroxy-6-isopropyl-2H-pyridazin-3-one | + |

| | Structure | Name | NS5B Polymerase IC50 |
|---|---|---|---|
| 64 | 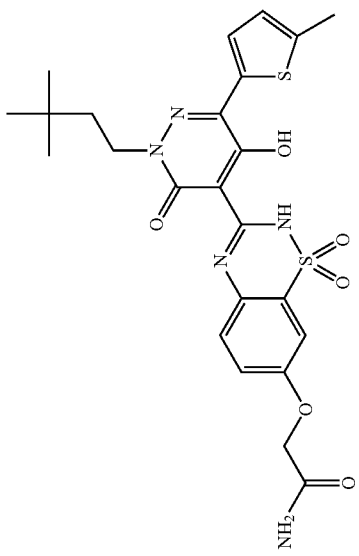 | 2-{3-[2-(3,3-Dimethyl-butyl)-5-hydroxy-6-(5-methyl-thiophen-2-yl)-3-oxo-2,3-dihydro-pyridazin-4-yl]-1,1-dioxo-1,2-dihydro-1λ⁶-benzo[1,2,4]thiadiazin-7-yloxy}-acetamide | ++ |
| 65 | 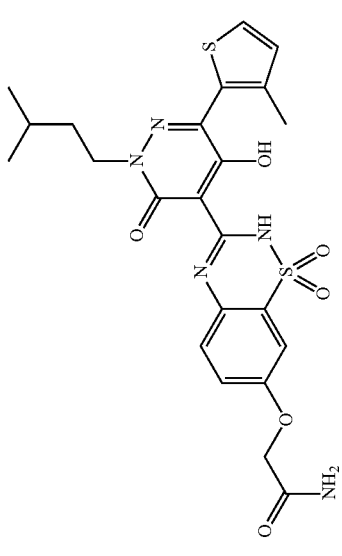 | 2-{3-[5-Hydroxy-2-(3-methyl-butyl)-6-(3-methyl-thiophen-2-yl)-3-oxo-2,3-dihydro-pyridazin-4-yl]-1,1-dioxo-1,2-dihydro-1λ⁶-benzo[1,2,4]thiadiazin-7-yloxy}-acetamide | ++ |
| 66 | 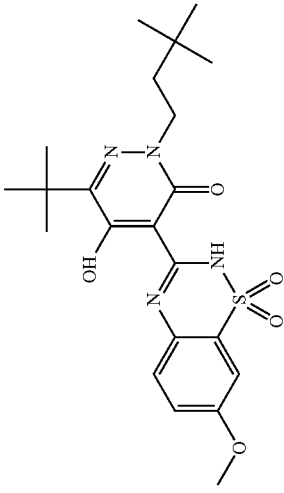 | 6-tert-Butyl-2-(3,3-dimethyl-butyl)-5-hydroxy-4-(7-methoxy-1,1-dioxo-1,2-dihydro-1λ⁶-benzo[1,2,4]thiadiazin-3-yl)-2H-pyridazin-3-one | + |

| | Structure | Name | NS5B Polymerase IC50 |
|---|---|---|---|
| 67 | 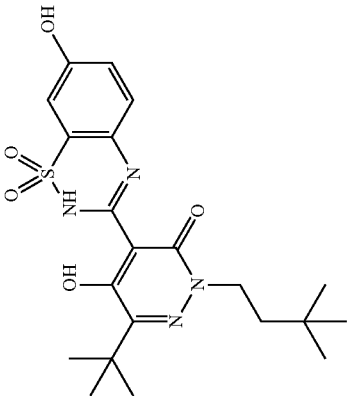 | 6-tert-Butyl-2-(3,3-dimethyl-butyl)-5-hydroxy-4-(7-hydroxy-1,1-dioxo-1,2-dihydro-1λ⁶-benzo[1,2,4]thiadiazin-3-yl)-2H-pyridazin-3-one | ++ |
| 68 | 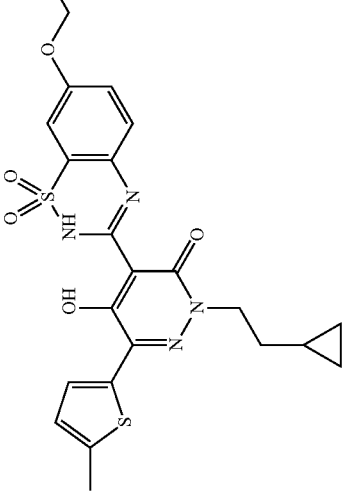 | 2-{3-[2-(2-Cyclopropyl-ethyl)-5-hydroxy-6-(5-methyl-thiophen-2-yl)-3-oxo-2,3-dihydro-pyridazin-4-yl]-1,1-dioxo-1,2-dihydro-1λ⁶-benzo[1,2,4]thiadiazin-7-yloxy}-acetamide | ++ |
| 69 | 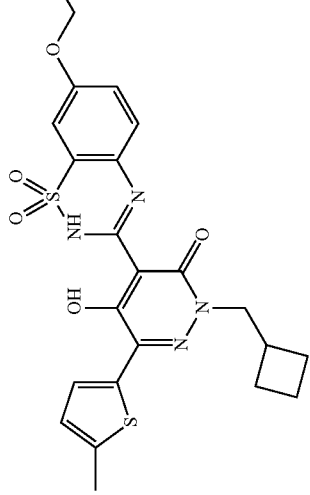 | 2-{3-[2-Cyclobutylmethyl-5-hydroxy-6-(5-methyl-thiophen-2-yl)-3-oxo-2,3-dihydro-pyridazin-4-yl]-1,1-dioxo-1,2-dihydro-1λ⁶-benzo[1,2,4]thiadiazin-7-yloxy}-acetamide | + |

| | Structure | Name | NS5B Polymerase IC50 |
|---|---|---|---|
| 70 | 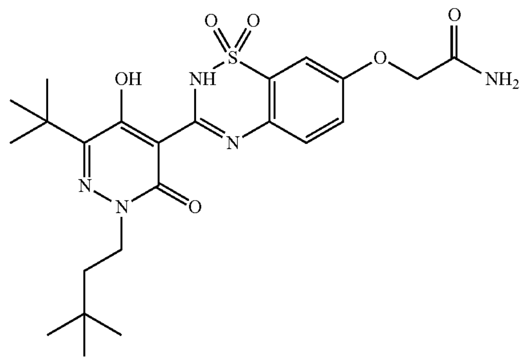 | 2-{3-[6-tert-Butyl-2-(3,3-dimethyl-butyl)-5-hydroxy-3-oxo-2,3-dihydro-pyridazin-4-yl]-1,1-dioxo-1,2-dihydro-1$\lambda^6$-benzo[1,2,4]thiadiazin-7-yloxy}-acetamide | ++ |

What is claimed is:

1. A compound according to Formula I

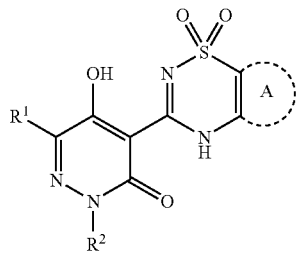

wherein
R¹ and R² are independently H, alkyl, cycloalkyl, aryl, or heterocyclyl, and
Ring A is 5- or 6-membered aryl or heterocyclyl,
wherein the above alkyl, aryl, cycloalkyl, or heterocyclyl moieties are optionally substituted by 1-3 substituents selected from
alkanoyl,
alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
—N=N—NH2,
—C(O)$_2$—($C_1$-$C_6$ alkyl), —C(O)$_2$-(aryl), —C(O)$_2$-(cycloalkyl), —C(O)$_2$-(heterocyclyl), —O—($C_1$-$C_6$ haloalkyl), —O—($C_1$-$C_6$ alkyl)aryl, —O—($C_1$-$C_6$ alkyl)cycloalkyl, —O—($C_1$-$C_6$ alkyl)heterocyclyl, —O—($C_1$-$C_6$ alkyl)amino, —O—($C_1$-$C_6$ alkyl)alkylamino, —O—($C_1$-$C_6$ alkyl)dialkylamino, —O—($C_1$-$C_6$ alkyl)-C(O)OH, —O—($C_1$-$C_6$ alkyl)-C(O)O—($C_1$-$C_6$ alkyl), —O—($C_1$-$C_6$ alkyl)-C(O)NH$_2$, —O—($C_1$-$C_6$ alkyl)-C(O)NH—($C_1$-$C_6$ alkyl), —O—($C_1$-$C_6$ alkyl)-C(O)N—($C_1$-$C_6$ alkyl)dialkyl, —O—($C_1$-$C_6$ alkyl)-C(O)-heterocyclyl, —O-aryl, —O-heterocyclyl, —NHC(O)-($C_1$-$C_6$ alkyl), —NHC(O)—($C_1$-$C_6$ alkylene), —NHC(O)-(aryl), —NHC(O)-cycloalkyl, —NHC(O)-(heterocyclyl), —NHC(O)—$C_1$-$C_6$ alkyl)aryl, —NHC(O)—($C_1$-$C_6$ alkyl)cycloalkyl, —NHC(O)—($C_1$-$C_6$ alkyl)heterocyclyl, —NHC(O)—($C_1$-$C_6$ alkyl)amino, —NHC(O)—($C_1$-$C_6$ alkyl)alkylamine, —NHC(O)—($C_1$-$C_6$ alkyl)dialkylamine, —NHC(O)—($C_1$-$C_6$ alkyl)C(O)amino, —NHC(O)—($C_1$-$C_6$ alkyl)C(O)alkylamine, —NHC(O)—($C_1$-$C_6$alkyl)C(O)dialkylamine, —NHC(O)—($C_1$-$C_6$ alkyl)N(H)—($C_1$-$C_6$ alkyl)C(O)$_2$—($C_1$-$C_6$ alkyl), —NHC(O)—($C_1$-$C_6$ alkyl)S(O)$_2$($C_1$-$C_6$ alkyl), —NHC(O)—($C_1$-$C_6$ alkyl)-S-(heterocyclyl), —NHS(O)$_2$—($C_1$-$C_6$ alkyl), —NHS(O)$_2$-(aryl), —NHS(O)$_2$-(cycloalkyl), —NHS(O)$_2$-(heterocyclyl), —NHS(O)($C_1$-$C_6$ alkyl), —NHS(O)(aryl), —NHS(O)(cycloalkyl), —NHS(O)(heterocyclyl), —NHS($C_1$-$C_6$ alkyl), —NHS(aryl), —NHS(cycloalkyl), —NH—S-(heterocyclyl),
wherein each of the above substituents can be further optionally substituted by 1-5 substituents selected from
amino,
$C_1$-$C_6$ alkylamine, $C_1$-$C_6$ dialkylamine,
$C_1$-$C_6$ alkyl, $C_1$-$C_6$ alkoxy, $C_1$-$C_6$ alkenyl, $C_1$-$C_6$ hydroxyl, and $C_1$-$C_6$
hydroxyalkyl, each optionally substituted by halo,
cyano, and
nitro,
or a pharmaceutically acceptable salt, hydrate, tautomer or stereoisomer thereof.

2. The compound of claim 1 wherein R¹ is selected from the group consisting of $C_1$-$C_6$ alkyl, aryl, and heterocyclyl having 1 to 3 N, O, or S atoms.

3. The compound of claim 1 wherein R¹ is selected from the group consisting of:

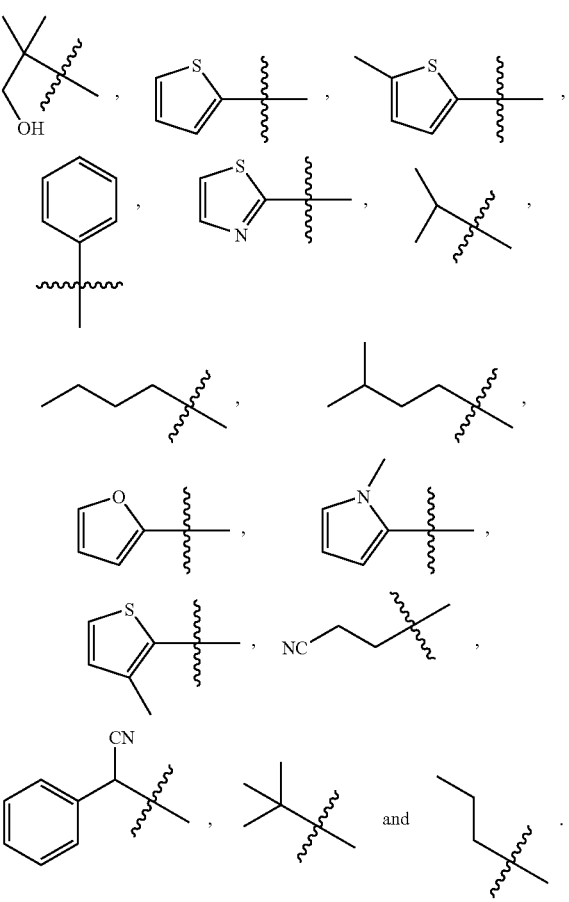

4. The compound of claim 1 wherein R² is selected from the group consisting of $C_1$-$C_6$ alkyl optionally substituted with $C_6$-$C_{10}$ aryl or $C_3$-$C_8$ cycloalkyl, heterocyclyl having 1 to 3 N, O, or S atoms, and aryl.

5. The compound of claim 1 wherein R² is selected from the group consisting of:

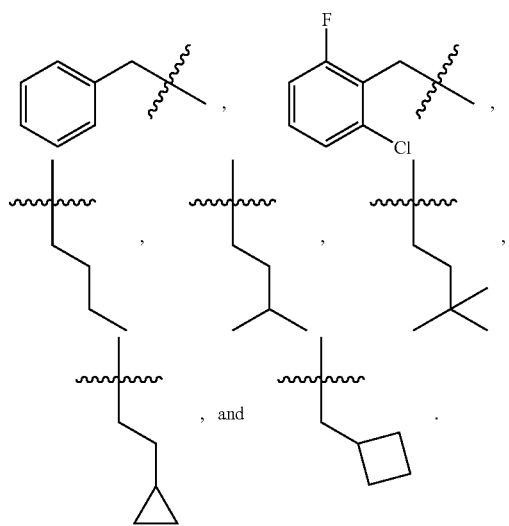

6. The compound of claim 1 wherein said Ring A is a 5- or 6-membered aryl or heterocyclyl, optionally substituted with -alkyl, -halo, —OH, —O-alkyl, —OCHR$^5$C(O)O-alkyl, —OCHR$^4$C(O)NR$^5$R$^6$, —NHR$^5$, —NR$^5$C(O)-aryl, NHSO$_2$R$^7$ or —NO$_2$, wherein R$^4$, R$^5$, R$^6$ and R$^7$ are independently —H or -alkyl, or R$^5$ and R$^6$ combine with the N atom to which they are attached to form a 5- or 6-membered heterocyclyl ring optionally substituted with —NH$_2$, and wherein alkyl is (C$_1$-C$_6$)-alkyl.

7. The compound of claim 1 wherein ring A, together with the ring to which it is fused, is selected from the group consisting of:

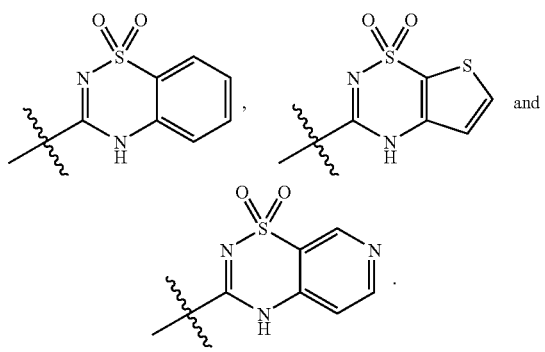

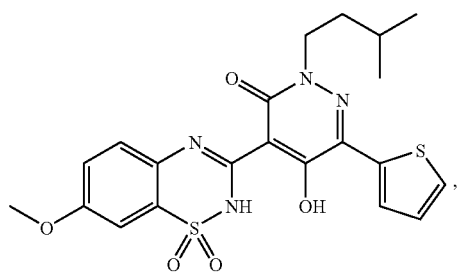

8. The compound of claim 1 wherein the compound is selected from the group consisting of:

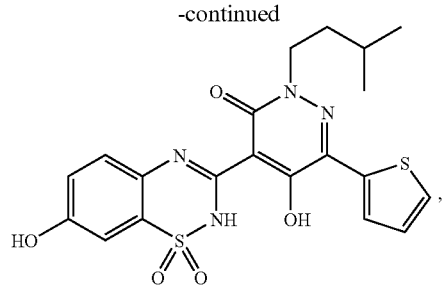

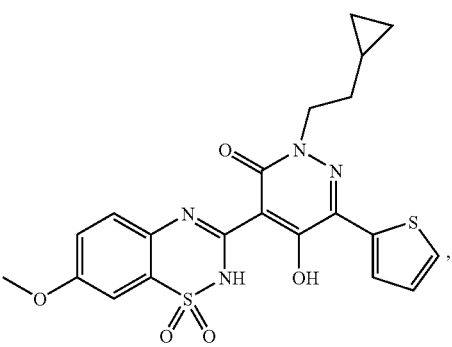

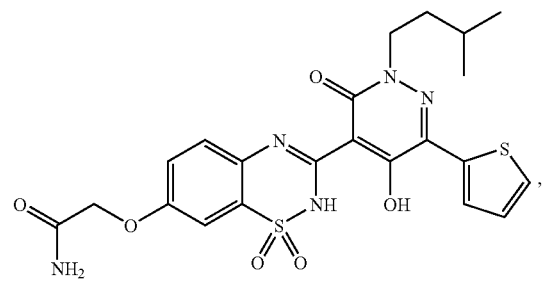

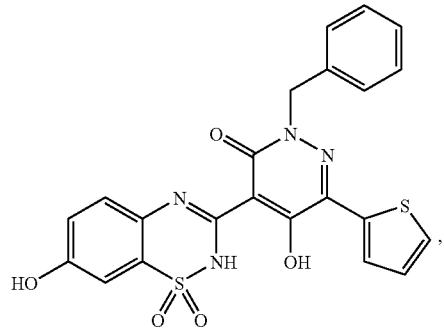

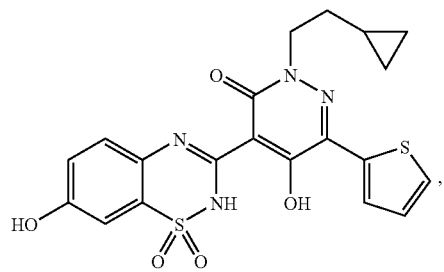

129
-continued
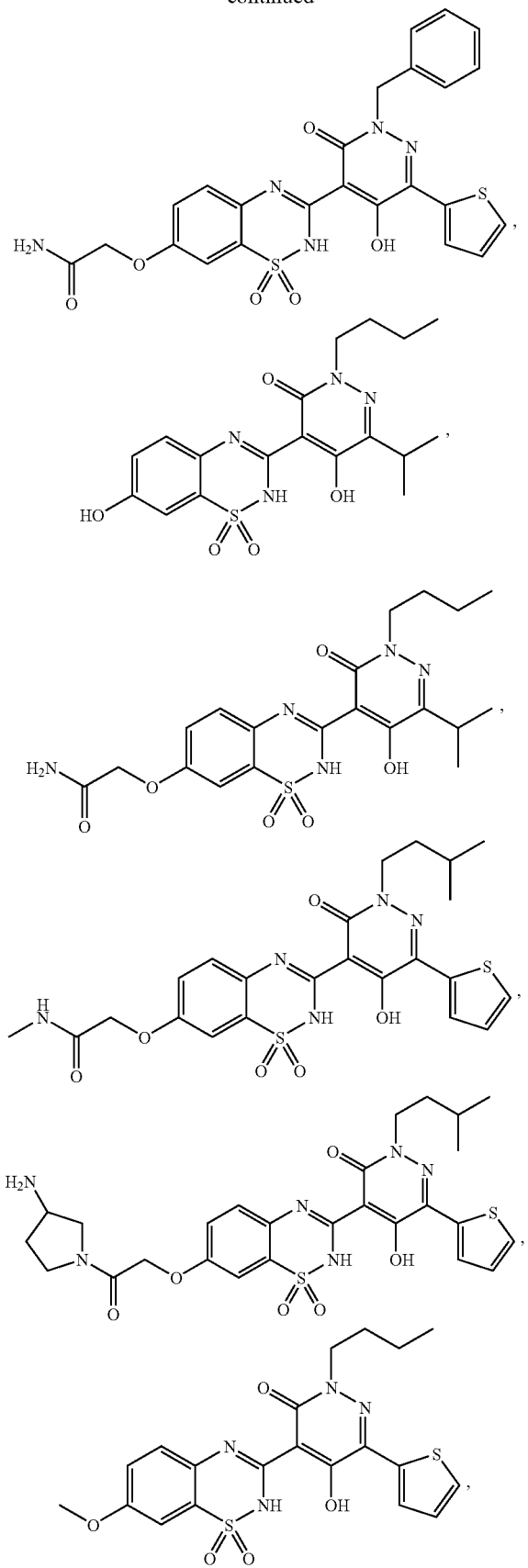
130
-continued
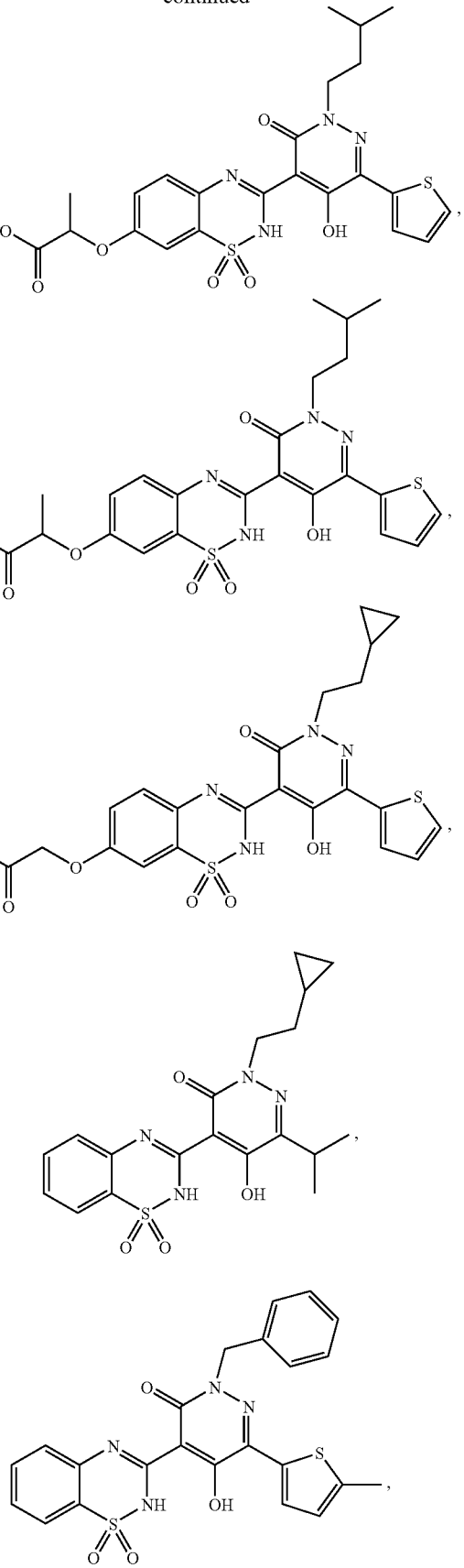

131
-continued
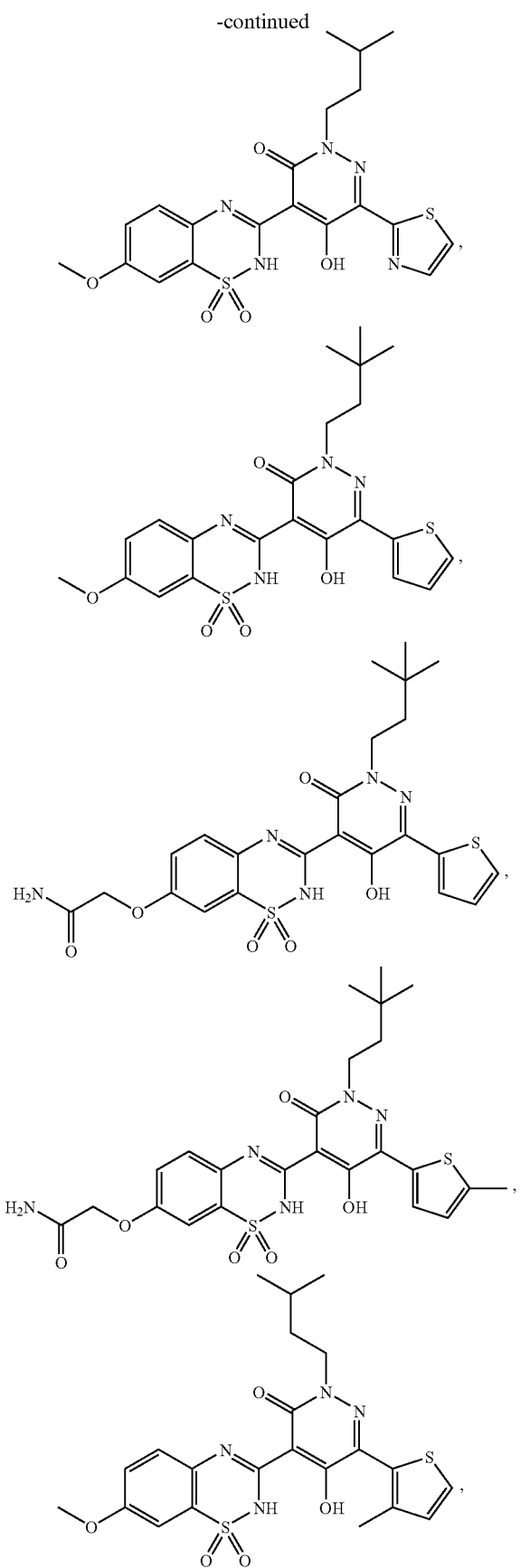
132
-continued
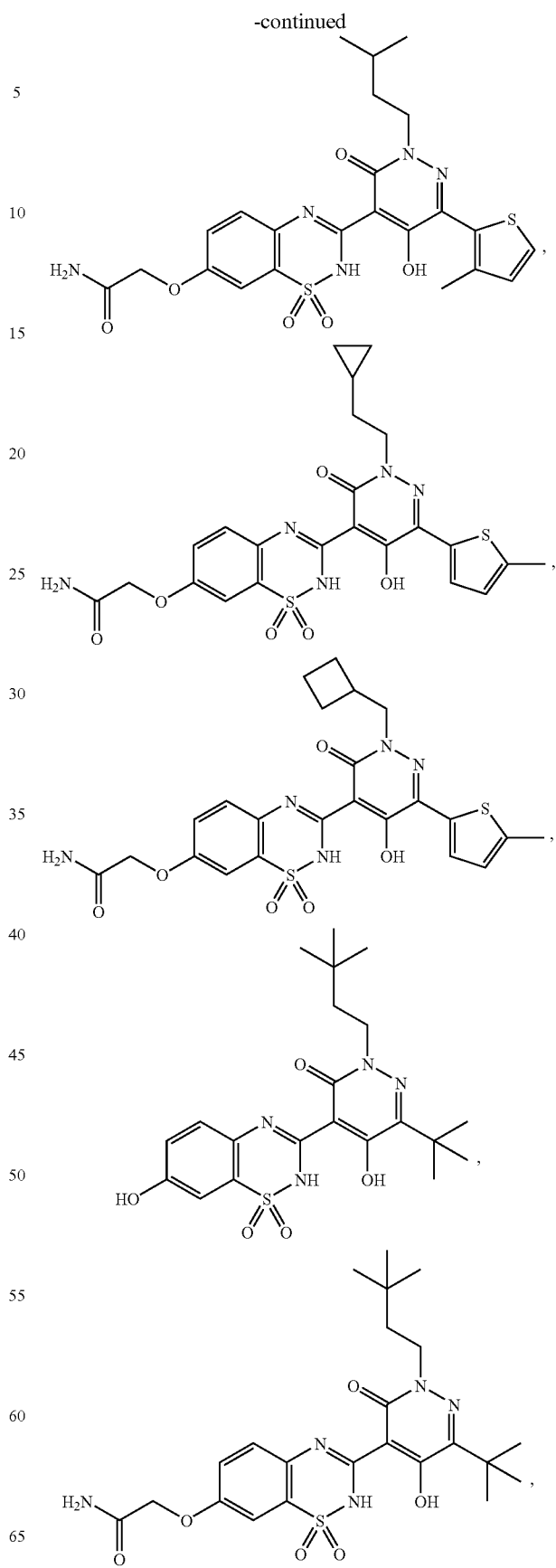

133
-continued
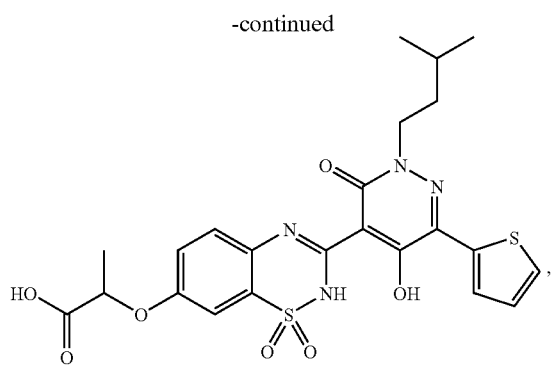
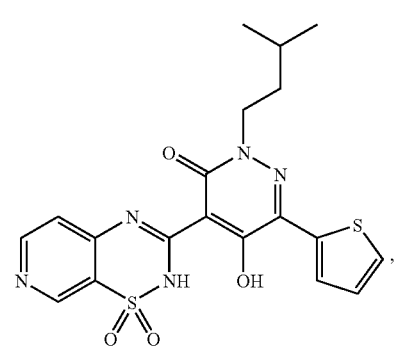
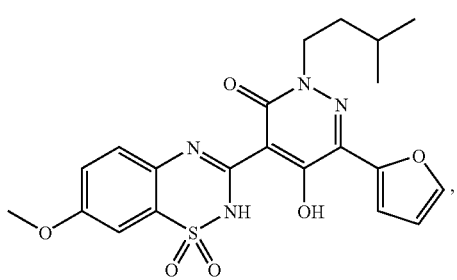
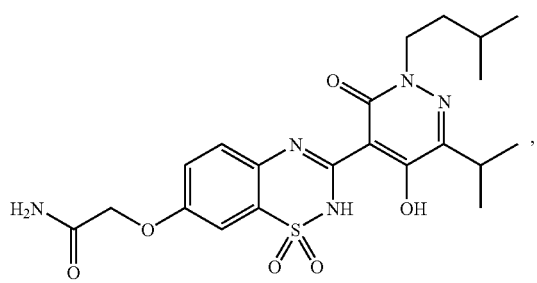
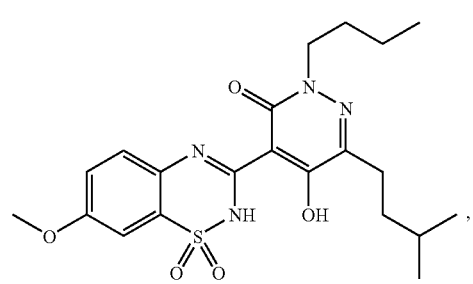
134
-continued
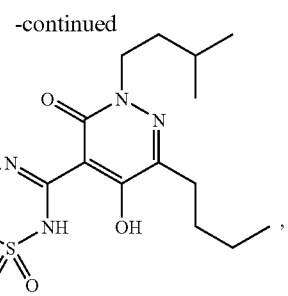
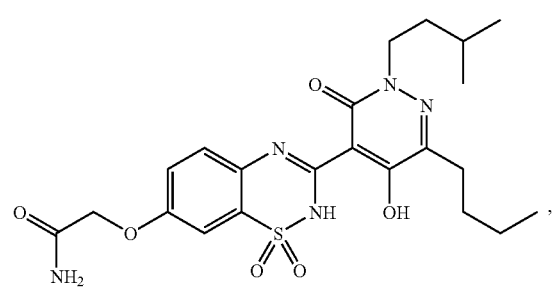
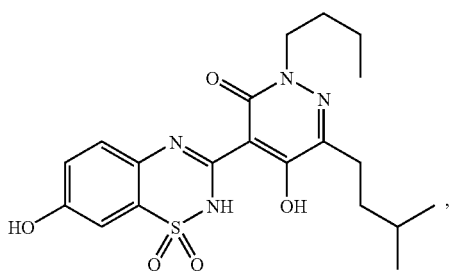
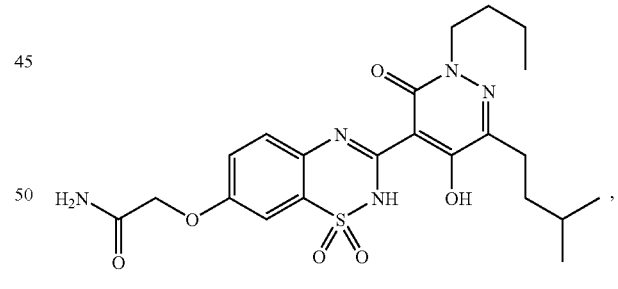
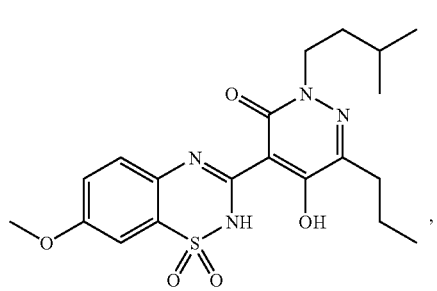

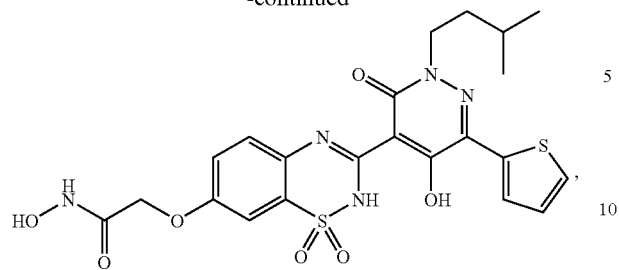

9. A pharmaceutically acceptable composition comprising a compound of claim 1 and a pharmaceutically acceptable carrier.

10. A method for treating hepatitis C virus infection in a mammal in need thereof, comprising administering to the mammal a therapeutically effective amount of a compound of claim 1.

11. The method of claim 10 wherein the mammal is a human.

12. The method of claim 10 further comprising administering an additional therapeutic agent to the mammal.

13. The method of claim 12 wherein the additional therapeutic agent is selected from the group consisting of an antibiotic, an antiemetic agent, an antidepressant, an antifungal agent, an anti-inflammatory agent, an antiviral agent, an anticancer agent, an immunomodulatory agent, an α-interferon, a β-interferon, a ribavirin, an alkylating agent, a hormone, a cytokine and a toll receptor-like modulator.

14. The method of claim 12 wherein the additional therapeutic agent is a toll receptor-like modulator.

* * * * *